(12) United States Patent
Dichterman et al.

(10) Patent No.: US 8,280,124 B2
(45) Date of Patent: Oct. 2, 2012

(54) METHODS OF VIEW SELECTION FOR RADIOACTIVE EMISSION MEASUREMENTS

(75) Inventors: Eli Dichterman, Haifa (IL); Ran Ravhon, Kiryat-Motzkin (IL); Michael Nagler, Tel-Aviv (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 1084 days.

(21) Appl. No.: 11/628,074

(22) PCT Filed: Jun. 1, 2005

(86) PCT No.: PCT/IL2005/000572
§ 371 (c)(1), (2), (4) Date: Mar. 19, 2008

(87) PCT Pub. No.: WO2005/118659
PCT Pub. Date: Dec. 15, 2005

(65) Prior Publication Data
US 2008/0260228 A1    Oct. 23, 2008

Related U.S. Application Data

(60) Provisional application No. 60/575,369, filed on Jun. 1, 2004, provisional application No. 60/625,971, filed on Nov. 9, 2004, provisional application No. 60/630,561, filed on Nov. 26, 2004, provisional application No. 60/632,236, filed on Dec. 2, 2004, provisional application No. 60/632,515, filed on Dec. 3, 2004, provisional application No. 60/635,630, filed on Dec. 14, 2004, provisional application No. 60/636,088, filed on Dec. 16, 2004, provisional application No. 60/640,215, filed on Jan. 3, 2005, provisional application No. 60/648,385, filed on Feb. 1, 2005, provisional application No. 60/648,690, filed on Feb. 2, 2005.

(51) Int. Cl.
*G06K 9/00* (2006.01)
(52) U.S. Cl. ............................................ 382/128; 378/8
(58) Field of Classification Search ................. 382/128, 382/131; 378/8
See application file for complete search history.

(56) References Cited

U.S. PATENT DOCUMENTS 2,776,377 A    1/1957    Anger
3,340,866 A    9/1967    Nöller
(Continued)

FOREIGN PATENT DOCUMENTS
DE    1516429    12/1969
(Continued)

OTHER PUBLICATIONS

Official Action Dated Dec. 8, 2010 From the US Patent and Trademark Office U.S. Appl. No. 11/980,690.

(Continued)

*Primary Examiner* — Alexander H Taningco

(57) ABSTRACT

A method is described for identifying an optimal, or preferred set of views for radioactive-emission measurements of a body structure, based on modeling the body structure, in terms of its geometry and radioactive emission distribution, obtaining different sets of views of the model, and scoring the different sets of views, with a scoring function, using information theoretic measures, for example, for uniformity, reliability and separability in reconstruction.

The preferred set of views may then be applied in imaging the in-vivo body structure, that has been modeled.

24 Claims, 43 Drawing Sheets
(35 of 43 Drawing Sheet(s) Filed in Color)

U.S. PATENT DOCUMENTS

| | | | |
|---|---|---|---|
| 3,684,887 A | 8/1972 | Hugonin | |
| 3,690,309 A | 9/1972 | Pluzhnikov et al. | |
| 3,719,183 A | 3/1973 | Schwartz | |
| 3,739,279 A | 6/1973 | Hollis | |
| 3,971,362 A | 7/1976 | Pope et al. | |
| 4,015,592 A | 4/1977 | Bradley-Moore | |
| 4,278,077 A | 7/1981 | Mizumoto | |
| 4,302,675 A * | 11/1981 | Wake et al. | 250/363.04 |
| 4,364,377 A | 12/1982 | Smith | |
| 4,521,688 A | 6/1985 | Yin | |
| H12 H | 1/1986 | Bennett et al. | |
| 4,595,014 A | 6/1986 | Barrett et al. | |
| 4,674,107 A | 6/1987 | Urban et al. | |
| 4,689,041 A | 8/1987 | Corday et al. | |
| 4,689,621 A | 8/1987 | Kleinberg | |
| 4,731,536 A | 3/1988 | Rische et al. | |
| 4,773,430 A | 9/1988 | Porath | |
| 4,828,841 A | 5/1989 | Porter et al. | |
| 4,844,067 A | 7/1989 | Ikada et al. | |
| 4,844,076 A | 7/1989 | Lesho et al. | |
| 4,893,013 A | 1/1990 | Denen et al. | |
| 4,928,250 A | 5/1990 | Greenberg et al. | |
| 4,929,832 A | 5/1990 | Ledley | |
| 4,951,653 A | 8/1990 | Fry et al. | |
| 4,959,547 A | 9/1990 | Carroll et al. | |
| 4,995,396 A | 2/1991 | Inaba et al. | |
| 5,014,708 A | 5/1991 | Hayashi et al. | |
| 5,032,729 A | 7/1991 | Charpak | |
| 5,033,998 A | 7/1991 | Corday et al. | |
| 5,070,878 A | 12/1991 | Denen | |
| 5,088,492 A | 2/1992 | Takayama et al. | |
| 5,119,818 A | 6/1992 | Carroll et al. | |
| 5,151,598 A | 9/1992 | Denen | |
| 5,170,055 A | 12/1992 | Carroll et al. | |
| 5,170,789 A | 12/1992 | Narayan et al. | |
| 5,243,988 A | 9/1993 | Sieben et al. | |
| 5,246,005 A | 9/1993 | Carroll et al. | |
| 5,249,124 A | 9/1993 | DeVito | |
| 5,279,607 A | 1/1994 | Schentag et al. | |
| 5,299,253 A | 3/1994 | Wessels | |
| 5,307,808 A | 5/1994 | Dumoulin et al. | |
| 5,349,190 A | 9/1994 | Hines et al. | |
| 5,383,456 A | 1/1995 | Arnold et al. | |
| 5,386,446 A | 1/1995 | Fujimoto et al. | |
| 5,395,366 A | 3/1995 | D'Andrea et al. | |
| 5,399,868 A | 3/1995 | Jones et al. | |
| 5,415,181 A | 5/1995 | Hogrefe et al. | |
| 5,441,050 A | 8/1995 | Thurston et al. | |
| 5,448,073 A | 9/1995 | Jeanguillaume | |
| 5,475,219 A | 12/1995 | Olson | |
| 5,484,384 A | 1/1996 | Fearnot | |
| 5,489,782 A | 2/1996 | Wernikoff | |
| 5,493,595 A | 2/1996 | Schoolman | |
| 5,519,221 A | 5/1996 | Weinberg | |
| 5,572,999 A | 11/1996 | Funda et al. | |
| 5,579,766 A | 12/1996 | Gray | |
| 5,604,531 A | 2/1997 | Iddan et al. | |
| 5,617,858 A | 4/1997 | Taverna et al. | |
| 5,635,717 A | 6/1997 | Popescu | |
| 5,657,759 A | 8/1997 | Essen-Moller | |
| 5,672,877 A | 9/1997 | Liebig et al. | |
| 5,682,888 A | 11/1997 | Olson et al. | |
| 5,690,691 A | 11/1997 | Chen et al. | |
| 5,694,933 A | 12/1997 | Madden et al. | |
| 5,695,500 A | 12/1997 | Taylor et al. | |
| 5,716,595 A | 2/1998 | Goldenberg | |
| 5,727,554 A | 3/1998 | Kalend et al. | |
| 5,729,129 A | 3/1998 | Acker | |
| 5,732,704 A | 3/1998 | Thurston et al. | |
| 5,744,805 A | 4/1998 | Raylman et al. | |
| 5,784,432 A | 7/1998 | Kurtz et al. | |
| 5,803,914 A | 9/1998 | Ryals et al. | |
| 5,811,814 A | 9/1998 | Leone et al. | |
| 5,821,541 A | 10/1998 | Tümer | |
| 5,833,603 A | 11/1998 | Kovacs et al. | |
| 5,838,009 A | 11/1998 | Plummer et al. | |
| 5,842,977 A | 12/1998 | Lesho et al. | |
| 5,846,513 A | 12/1998 | Carroll et al. | |
| 5,857,463 A | 1/1999 | Thurston et al. | |
| 5,871,013 A | 2/1999 | Wainer et al. | |
| 5,880,475 A | 3/1999 | Oka et al. | |
| 5,891,030 A | 4/1999 | Johnson et al. | |
| 5,900,533 A | 5/1999 | Chou | |
| 5,916,167 A | 6/1999 | Kramer et al. | |
| 5,928,150 A | 7/1999 | Call | |
| 5,932,879 A | 8/1999 | Raylman et al. | |
| 5,939,724 A | 8/1999 | Eisen et al. | |
| 5,961,457 A | 10/1999 | Raylman et al. | |
| 5,984,860 A | 11/1999 | Shan | |
| 5,987,350 A | 11/1999 | Thurston | |
| 5,993,378 A | 11/1999 | Lemelson | |
| 6,002,480 A | 12/1999 | Izatt et al. | |
| 6,072,177 A | 6/2000 | McCroskey et al. | |
| 6,076,009 A | 6/2000 | Raylman et al. | |
| 6,082,366 A | 7/2000 | Andra et al. | |
| 6,107,102 A | 8/2000 | Ferrari | |
| 6,115,635 A | 9/2000 | Bourgeois | |
| 6,129,670 A | 10/2000 | Burdette et al. | |
| 6,132,372 A | 10/2000 | Essen-Moller | |
| 6,135,955 A | 10/2000 | Madden et al. | |
| 6,147,353 A | 11/2000 | Gagnon et al. | |
| 6,160,398 A | 12/2000 | Walsh | |
| 6,173,201 B1 | 1/2001 | Front | |
| 6,205,347 B1 | 3/2001 | Morgan et al. | |
| 6,212,423 B1 | 4/2001 | Krakovitz | |
| 6,226,350 B1 * | 5/2001 | Hsieh | 378/98 |
| 6,233,304 B1 * | 5/2001 | Hu et al. | 378/8 |
| 6,236,878 B1 | 5/2001 | Taylor et al. | |
| 6,236,880 B1 | 5/2001 | Raylman et al. | |
| 6,239,438 B1 | 5/2001 | Schubert | |
| 6,240,312 B1 | 5/2001 | Alfano et al. | |
| 6,242,743 B1 | 6/2001 | DeVito et al. | |
| 6,246,901 B1 | 6/2001 | Benaron | |
| 6,252,924 B1 * | 6/2001 | Davantes et al. | 378/8 |
| 6,261,562 B1 | 7/2001 | Xu et al. | |
| 6,263,229 B1 | 7/2001 | Atalar et al. | |
| 6,271,524 B1 | 8/2001 | Wainer et al. | |
| 6,271,525 B1 | 8/2001 | Majewski et al. | |
| 6,280,704 B1 | 8/2001 | Schutt et al. | |
| 6,310,968 B1 | 10/2001 | Hawkins et al. | |
| 6,324,418 B1 | 11/2001 | Crowley et al. | |
| 6,339,652 B1 | 1/2002 | Hawkins et al. | |
| 6,346,706 B1 | 2/2002 | Rogers et al. | |
| 6,368,331 B1 | 4/2002 | Front et al. | |
| 6,381,349 B1 | 4/2002 | Zeng et al. | |
| 6,392,235 B1 | 5/2002 | Barrett et al. | |
| 6,407,391 B1 | 6/2002 | Mastrippolito et al. | |
| 6,415,046 B1 | 7/2002 | Kerut, Sr. | |
| 6,420,711 B2 | 7/2002 | Tuemer | |
| 6,426,917 B1 | 7/2002 | Tabanou et al. | |
| 6,429,431 B1 | 8/2002 | Wilk | |
| 6,431,175 B1 | 8/2002 | Penner et al. | |
| 6,438,401 B1 | 8/2002 | Cheng et al. | |
| 6,453,199 B1 | 9/2002 | Kobozev | |
| 6,459,925 B1 | 10/2002 | Nields et al. | |
| 6,480,732 B1 | 11/2002 | Tanaka et al. | |
| 6,484,051 B1 * | 11/2002 | Daniel | 600/436 |
| 6,490,476 B1 | 12/2002 | Townsend et al. | |
| 6,504,899 B2 * | 1/2003 | Pugachev et al. | 378/65 |
| 6,510,336 B1 | 1/2003 | Daghighian et al. | |
| 6,516,213 B1 | 2/2003 | Nevo | |
| 6,525,320 B1 | 2/2003 | Juni | |
| 6,525,321 B2 | 2/2003 | Juni | |
| 6,549,646 B1 | 4/2003 | Yeh et al. | |
| 6,560,354 B1 | 5/2003 | Maurer, Jr. et al. | |
| 6,567,687 B2 | 5/2003 | Front et al. | |
| 6,584,348 B2 | 6/2003 | Glukhovsky | |
| 6,587,710 B1 | 7/2003 | Wainer | |
| 6,592,520 B1 | 7/2003 | Peszynski et al. | |
| 6,602,488 B1 | 8/2003 | Daghighian | |
| 6,607,301 B1 | 8/2003 | Glukhovsky et al. | |
| 6,611,141 B1 | 8/2003 | Schulz et al. | |
| 6,614,453 B1 | 9/2003 | Suri et al. | |
| 6,628,983 B1 | 9/2003 | Gagnon | |
| 6,628,984 B2 | 9/2003 | Weinberg | |
| 6,632,216 B2 | 10/2003 | Houzego et al. | |
| 6,633,658 B1 | 10/2003 | Dabney et al. | |

| | | | |
|---|---|---|---|
| 6,638,752 B2 | 10/2003 | Contag et al. | |
| 6,643,538 B1 | 11/2003 | Majewski et al. | |
| 6,662,036 B2 | 12/2003 | Cosman | |
| 6,674,834 B1* | 1/2004 | Acharya et al. | 378/18 |
| 6,680,750 B1 | 1/2004 | Tournier et al. | |
| 6,697,660 B1 | 2/2004 | Robinson | |
| 6,728,583 B2 | 4/2004 | Hallett | |
| 6,748,259 B1 | 6/2004 | Benaron et al. | |
| 6,766,048 B1 | 7/2004 | Launay et al. | |
| 6,771,802 B1* | 8/2004 | Patt et al. | 382/128 |
| 6,776,977 B2 | 8/2004 | Liu | |
| 6,937,750 B2 | 8/2005 | Natanzon et al. | |
| 6,943,355 B2 | 9/2005 | Shwartz et al. | |
| 6,963,770 B2 | 11/2005 | Scarantino et al. | |
| 7,043,063 B1 | 5/2006 | Noble et al. | |
| 7,103,204 B1 | 9/2006 | Celler et al. | |
| 7,127,026 B2 | 10/2006 | Amemiya et al. | |
| 7,142,634 B2 | 11/2006 | Engler et al. | |
| 7,176,466 B2 | 2/2007 | Rousso et al. | |
| 7,187,790 B2 | 3/2007 | Sabol et al. | |
| 7,327,822 B2 | 2/2008 | Sauer et al. | |
| 7,359,535 B2 | 4/2008 | Salla et al. | |
| 7,394,923 B2 | 7/2008 | Zou et al. | |
| 7,468,513 B2 | 12/2008 | Charron et al. | |
| 7,490,085 B2 | 2/2009 | Walker et al. | |
| 7,570,732 B2 | 8/2009 | Stanton et al. | |
| 7,620,444 B2 | 11/2009 | Le et al. | |
| 7,680,240 B2 | 3/2010 | Manjeshwar et al. | |
| 7,705,316 B2 | 4/2010 | Rousso et al. | |
| 7,968,851 B2 | 6/2011 | Rousso et al. | |
| 2002/0072784 A1 | 6/2002 | Sheppard, Jr. et al. | |
| 2002/0085748 A1 | 7/2002 | Baumberg | |
| 2002/0087101 A1 | 7/2002 | Barrick et al. | |
| 2002/0099295 A1 | 7/2002 | Gil et al. | |
| 2002/0103431 A1 | 8/2002 | Toker et al. | |
| 2002/0148970 A1 | 10/2002 | Wong et al. | |
| 2002/0168317 A1 | 11/2002 | Daighighian et al. | |
| 2002/0183645 A1 | 12/2002 | Nachaliel | |
| 2002/0188197 A1 | 12/2002 | Bishop et al. | |
| 2003/0001837 A1 | 1/2003 | Baumberg | |
| 2003/0013966 A1 | 1/2003 | Barnes et al. | |
| 2003/0063787 A1 | 4/2003 | Natanzon et al. | |
| 2003/0081716 A1 | 5/2003 | Tumer | |
| 2003/0191430 A1 | 10/2003 | D'Andrea et al. | |
| 2003/0202629 A1 | 10/2003 | Dunham et al. | |
| 2003/0208117 A1 | 11/2003 | Shwartz et al. | |
| 2003/0215124 A1* | 11/2003 | Li | 382/131 |
| 2003/0216631 A1 | 11/2003 | Bloch et al. | |
| 2004/0003001 A1 | 1/2004 | Shimura | |
| 2004/0010397 A1 | 1/2004 | Barbour et al. | |
| 2004/0015075 A1 | 1/2004 | Kimchy et al. | |
| 2004/0054248 A1 | 3/2004 | Kimchy et al. | |
| 2004/0054278 A1 | 3/2004 | Kimchy et al. | |
| 2004/0081623 A1 | 4/2004 | Eriksen et al. | |
| 2004/0086437 A1 | 5/2004 | Jackson et al. | |
| 2004/0101176 A1 | 5/2004 | Mendonca et al. | |
| 2004/0116807 A1 | 6/2004 | Amrami et al. | |
| 2004/0122311 A1 | 6/2004 | Cosman | |
| 2004/0138557 A1 | 7/2004 | Le et al. | |
| 2004/0153128 A1 | 8/2004 | Suresh et al. | |
| 2004/0171924 A1 | 9/2004 | Mire et al. | |
| 2004/0184644 A1* | 9/2004 | Leichter et al. | 382/128 |
| 2004/0195512 A1 | 10/2004 | Crosetto | |
| 2004/0204646 A1 | 10/2004 | Nagler et al. | |
| 2004/0251419 A1 | 12/2004 | Nelson et al. | |
| 2005/0020915 A1 | 1/2005 | Bellardinelli et al. | |
| 2005/0033157 A1 | 2/2005 | Klein et al. | |
| 2005/0055174 A1 | 3/2005 | David et al. | |
| 2005/0145797 A1 | 7/2005 | Oaknin et al. | |
| 2005/0205792 A1 | 9/2005 | Rousso et al. | |
| 2005/0211909 A1 | 9/2005 | Smith | |
| 2005/0215889 A1 | 9/2005 | Patterson, II | |
| 2005/0253073 A1 | 11/2005 | Joram et al. | |
| 2005/0266074 A1 | 12/2005 | Zilberstein et al. | |
| 2006/0074290 A1 | 4/2006 | Chen et al. | |
| 2006/0160157 A1 | 7/2006 | Zuckerman | |
| 2006/0237652 A1 | 10/2006 | Kimchy et al. | |
| 2006/0257012 A1* | 11/2006 | Kaufman et al. | 382/131 |
| 2007/0156047 A1* | 7/2007 | Nagler et al. | 600/436 |
| 2007/0166227 A1 | 7/2007 | Liu et al. | |
| 2007/0194241 A1 | 8/2007 | Rousso et al. | |
| 2007/0265230 A1 | 11/2007 | Rousso et al. | |
| 2008/0033291 A1 | 2/2008 | Rousso et al. | |
| 2008/0042067 A1 | 2/2008 | Rousso et al. | |
| 2008/0128626 A1 | 6/2008 | Rousso et al. | |
| 2008/0230705 A1 | 9/2008 | Rousso et al. | |
| 2008/0237482 A1 | 10/2008 | Shahar et al. | |
| 2008/0260228 A1 | 10/2008 | Dichterman et al. | |
| 2008/0260637 A1 | 10/2008 | Dickman | |
| 2008/0277591 A1 | 11/2008 | Shahar et al. | |
| 2009/0078875 A1 | 3/2009 | Rousso et al. | |
| 2009/0112086 A1 | 4/2009 | Melman | |
| 2009/0152471 A1 | 6/2009 | Rousso et al. | |
| 2009/0190807 A1 | 7/2009 | Rousso et al. | |
| 2009/0201291 A1 | 8/2009 | Ziv et al. | |
| 2010/0021378 A1 | 1/2010 | Rousso et al. | |
| 2010/0245354 A1 | 9/2010 | Rousso et al. | |

FOREIGN PATENT DOCUMENTS

| | | |
|---|---|---|
| DE | 19814199 | 10/1999 |
| DE | 19815362 | 10/1999 |
| EP | 0543626 | 5/1993 |
| EP | 0697193 | 2/1996 |
| EP | 0887661 | 12/1998 |
| GB | 2031142 | 4/1980 |
| JP | 6-109848 | 4/1994 |
| JP | 06-109848 | 4/1994 |
| WO | WO 92/00402 | 9/1992 |
| WO | 99/03003 | 1/1999 |
| WO | WO 99/30610 | 6/1999 |
| WO | WO 99/39650 | 8/1999 |
| WO | WO 00/10034 | 2/2000 |
| WO | WO 00/31522 | 2/2000 |
| WO | WO 00/22975 | 4/2000 |
| WO | WO 00/18294 | 6/2000 |
| WO | WO 01/89384 | 11/2001 |
| WO | WO 02/58531 | 1/2002 |
| WO | WO 02/16965 | 2/2002 |
| WO | WO 2004/042546 | 5/2004 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054281 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Official Action Dated Nov. 10, 2010 From the US Patent and Trademark Office U.S. Appl. No. 10/616,307.

Official Action Dated Nov. 10, 2010 From the US Patent and Trademark Office U.S. Appl. No. 10/836,223.

Official Action Dated Nov. 23, 2010 From the US Patent and Trademark Office U.S. Appl. No. 11/656,548.

Response Dated Nov. 18, 2010 to Official Action of Jul. 19, 2010 From the US Patent and Trademark Office U.S. Appl. No. 11/607,075.

Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.

Hassan et al. "A Radiotelemetry Pill for the Measurement of Ionising Radiation Using a Mercuric Iodide Detector", Phys. Med. Biol., 23(2): 302-308, 1978.

Hoffman et al. "Intraoperative Probes and Imaging Probes", European Journal of Nuclear Medicine, 26(8): 913-935, 1999.

Zhang et al. "An Innovative High Efficiency and High Resolution Probe for Prostate Imaging", The Journal of Nuclear Medicine, 68: 18, 2000. Abstract.
Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Sep. 2, 2009 From the US Patent and Trademark Office Re.: U.S. Appl. No. 10/343,792.
Official Action Dated Aug. 11, 2009 From the US Patent and Trademark Office Re.: U.S. Appl. No. 09/641,973.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Sep. 16, 2009 From the US Patent and Trademark Office Re.: U.S. Appl. No. 09/727,464.
Official Action Dated Sep. 21, 2009 From the US Patent and Trademark Office Re.: U.S. Appl. No. 11/798,017.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Oct. 14, 2009 to Official Action of May 14, 2009 From the US Patent and Trademark Office Re.: U.S. Appl. No. 11/656,548.
Response Dated Nov. 16, 2009 to Official Action of Jul. 15, 2009 From the US Patent and Trademark Office Re.: U.S. Appl. No. 10/616,301.
Supplementary Partial European Search Report and the European Search Opinion Dated Oct. 16, 2009 From the European Patent Office Re.: Application No. 06756259.5.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and noise Properties of MAP Reconstruction for Fully 3-D PET", IEEE Transactions on Medical Imaging, XP002549082, 19(5): 493-506, May 2000. p. 493, col. 2, Lines 10-21, p. 495, Col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Official Action Dated Dec. 28, 2010 From the US Patent and Trademark Office Re.: U.S. Appl. No. 11/607,075.
Response Dated Dec. 15, 2010 to Official Action of Jul. 19, 2010 From the US Patent and Trademark Office Re.: U.S. Appl. No. 11/656,548.
Communication Pursuant to Article 96(2) EPC Dated Jun. 19, 2006 From the European Patent Office Re.: Application No. 03810570.6.
Communication pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperation Treaty Re.: Application No. PCT/IL05/00575.
International Search Report Dated Nov. 1, 2007 From the International Searching Authority of the Patent Cooperation Treaty Re.: Application No. PCT/IL06/00840.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated Mar. 26, 2007 From the International Searching Authority of the Patent Cooperation Treaty Re.: Application No. PCT/IL05/00394.
Official Action Dated Jun. 1, 2006 From the United States Patent and Trademark Office Re.: U.S. Appl. No. 10/686,536.
Official Action Dated Dec. 2, 2007 From the Israeli Patent Office Re.: Application No. 158442.
Official Action Dated May 3, 2007 From the United States Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Aug. 10, 2007 From the United States Patent and Trademark Office Re.: U.S. Appl. No. 10/836,223.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.
Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jan. 17, 2006 From the United States Patent and Trademark Office Re.: U.S. Appl. No. 11/034,007.

Official Action Dated Jul. 17, 2007 From the Israeli Patent Office Re.: Application No. 154323.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Oct. 10, 2006 From the International Searching Authority of the Patent Cooperation Treaty Re.: Application No. PCT/IL06/00059.
Written Opinion Dated Jul. 2, 2007 From the International Searching Authority of the Patent Cooperation Treaty Re.: Application No. PCT/IL2006/001291.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gugnin et al "Radiocapsule for Recording the Ionizing Radiation in The Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2—p. 585, § 1.
Official Action Dated Jan. 31, 2011 From the US Patent and Trademark Office Re. U.S. Appl. No. 11/667,793.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Communication Pursuant to Article 94(3) EPC Dated Mar. 2, 2011 From the European Patent Office Re.: Application No. 06756259.5.
Notice of Allowance Dated Nov. 15, 2010 From the US Patent and Trademark Office Re. U.S. Appl. No. 10/616,301.
Notice of Non-Compliant Amendment Dated Feb. 14, 2011 From the US Patent and Trademark Office Re.: U.S. Appl. No. 10/616,307.
Response Dated Feb. 10, 2011 to Notice of Allowance of Nov. 15, 2010 From the US Patent and Trademark Office Re. U.S. Appl. No. 10/616,301.

Mettler et al. "Legal Requirements and Radiation Safety", Essentials of Nuclear Medicine Imaging, 2nd Ed., Chap.13: 323-331, 1985.
Response Dated Mar. 8, 2011 to Official Action of Dec. 8, 2010 From the US Patent and Trademark Office Re.: U.S. Appl. No. 11/980,690.
Lavall?e et al. "Building A Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Technical Brief, JPL New Technology Report, NPO-20652, 25(2), 2000.
Notice of Allowance Dated Feb. 23, 2011 From the US Patent and Trademark Office Re.: U.S. Appl. No. 11/980,690.
Official Action Dated Mar. 15, 2011 From the US Patent and Trademark Office Re.: U.S. Appl. No. 10/343,792.
Response Dated Mar. 24, 2011 to Official Action of Dec. 8, 2010 From the US Patent and Trademark Office Re.: U.S. Appl. No. 09/641,973.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.
Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Response Dated Mar. 3, 2011 to Notice of Non-Compliant Amendment of Feb. 14, 2011 From the US Patent and Trademark Office Re.: U.S. Appl. No. 10/616,307.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Jan. 2, 2006 From the Israeli Patent Office Re.: Application No. 154323.
Office Action Dated Sep. 4, 2007 From the Israeli Patent Office Re.: Application No. 157007.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.

Official Action Dated Mar. 11, 2010 From the US Patent and Trademark Office Re.: U.S. Appl. No. 11/607,075.
Official Action Dated Mar. 19, 2010 From the US Patent and Trademark Office Re.: U.S. Appl. No. 10/240,239.
Official Action Dated Feb. 23, 2010 From the US Patent and Trademark Office Re.: U.S. Appl. No. 09/641,973.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas et al. "Static Versus Dynamic Teboroxime Myocardial Perfusion SPECT in Canines", IEEE Transcations on Nuclear Science, 47(3): 1112-1117, Jun. 2000.
Li et al. "A HOTLink/Networked PC Data Acquisition and Image Reconstruction System for A High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Official Action Dated Apr. 9, 2010 From the US Patent and Trademark Office Re.: U.S. Appl. No. 11/798,017.
Official Action Dated Jan. 7, 2009 From the US Patent and Trademark Office Re.: U.S. Appl. No. 10/616,307.
Summons to Attend Oral Proceedings Pursuant to Rule 115(1) EPC Dated Jan. 16, 2009 From the European Patent Office Re.: Application No. 03810570.6.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Kinahan et al. "Attenuation Correction for A Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Notice of Allowance Dated May 5, 2011 From the US Patent and Trademark Office Re.: U.S. Appl. No. 10/240,239.
Communication Pursuant to Article 93(3) EPC Dated Mar. 8, 2010 From the European Patent Office Re.: Application No. 06832278.3.
International Search Report Dated Oct. 10, 2006 From the International Searching Authority of the Patent Cooperation Treaty Re.: Application No. PCT/IL06/00059.
Written Opinion Dated Aug. 3, 2006 From the International Searching Authority of the Patent Cooperation Treaty Re.: Application No. PCT/IL05/001173.
Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated Apr. 27, 2011 From the US Patent and Trademark Office Re.: U.S. Appl. No. 10/836,223.
Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re. Application No. 01951883.6.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Response Dated Jul. 8, 2010 to Communication Pursuant to Article 94(3) EPC of Mar. 8, 2010 From the European Patent Office Re.: Application No. 06832278.3.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Official Action of Apr. 9, 2010 From the US Patent and Trademark Office Re.: U.S. Appl. No. 11/798,017.
Response Dated Jun. 23, 2010 to Official Action of Feb. 23, 2010 From the US Patent and Trademark Office e.: U.S. Appl. No. 09/641,973.
Official Action Dated Jul. 27, 2010 From the US Patent and Trademark Office Re.: U.S. Appl. No. 10/616,307.
Response Dated Jul. 26, 2010 to Official Action of Apr. 28, 2010 From the US Patent and Trademark Office Re.: U.S. Appl. No. 10/616,301.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Notice of Allowance Dated Jul. 22, 2010 From the US Patent and Trademark Office Re.: U.S. Appl. No. 11/794,799.

Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Response Dated Aug. 25, 2010 to Official Action of Jul. 27, 2010 From the US Patent and Trademark Office Re.: U.S. Appl. No. 10/616,307.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re. U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Communication Pursuant to Article 94(3) EPC Dated Jul. 22, 2009 From the European Patent Office Re.: Application No. 06809851.6.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Sep. 12, 2002 From the International Searching Authority of the Patent Cooperation Treaty Re: Application No. PCT/IL02/00057.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Jul. 15, 2009 From the US Patent and Trademark Office Re.: U.S. Appl. No. 10/616,301.
Official Action Dated Dec. 16, 2008 From the US Patent and Trademark Office Re.: U.S. Appl. No. 10/343,792.
Official Action Dated Jul. 20, 2009 From the US Patent and Trademark Office Re.: U.S. Appl. No. 11/980,617.
Official Action Dated Dec. 23, 2008 From the US Patent and Trademark Office Re.: U.S. Appl. No. 09/727,464.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Apr. 7, 2009 to Official Action of Oct. 7, 2008 From the US Patent and Trademark Office Re.: U.S. Appl. No. 10/616,301.
Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.
Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Nov. 25, 2005 to Office Action of May 13, 2005 From the Patent Office of the People's Republic of China Re.: Application No. 1817689.5.
Response Dated Oct. 31, 2007 to Official Action of Jul. 12, 2007 From the US Patent and Trademark Office Re.: U.S. Appl. No. 10/616,301.
Response to the International Search Report and the Written Opinion of Oct. 10, 2006 From the International Searching Authority Re.: Appliction No. PCT/IL06/00059.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Response dated Sep. 1, 2010 to Official Action of Aug. 3, 2010 From the US Patent and Trademark Office Re.: U.S. Appl. No. 11/980,690.
Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using An Anatomical Model: Preliminary Results", IEEE Transactions on Medical Imaging, 16(6): 828-839, Dec. 1997.
Del Guerra et al. "An Integrated PET-SPECT Small Animal Imager: Preliminary Results", Nuclear Science Symposium, IEEE Records, 1: 541-544, 1999.
International Preliminary Report on Patentability Dated Apr. 16, 2009 From the International Bureau of WIPO Re.: Applicaiton No. PCT/IL2007/000918.
International Search Report Dated May 24, 2007 From the international Searching Authority of the Patent Cooperation Treaty Re.: Application No. PCT/IL05/00575.

Office Action Dated Dec. 2, 2007 From the Israeli Patent Office Re.: Application No. 158442.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated May 3, 2007 From the US Patent and Trademark Office Re.: U.S. Appl. No. 10/240,239.
Official Action Dated Sep. 5, 2002 From the US Patent and Trademark Office Re.: U.S. Appl. No. 12/084,559.
Official Action Dated Oct. 7, 2008 From the US Patent and Trademark Office Re.: U.S. Appl. No. 10/616,301.
Official Action Dated Aug. 10, 2007 From the US Patent and Trademark Office Re.: U.S. Appl. No. 10/836,223.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/765,316.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, Col.2, § 2.
Hassan et al. "A Radiotelemetry Pill for the Measurement of Ionising Radiation Using A Mercuric Iodide Detector", Physics in Medicine and Biology, 23(2): 302-308, 1978.
Lavallée et al. "Building A Hybrid Patient's Model for Augmented Reality in Surgery: A Registration Problem", Computing in Biological Medicine, 25(2): 149-164, 1995.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Reutter et al. "Direct Least Squares Estimation of Spatiotemporal Distributions From Dynamic SPECT Projections Using A Spatial Segmentation and Temporal B-Splines", IEEE Transactions on Medical Imaging, 19(5): 434-450, 2000.
Huesman et al. "Kinetic Parameter Estimation From SPECT Cone-Beam Projection Measurements", Physics in Medicine and Biology, 43(4): 973-982, 1998.
Reutter et al. "Kinetic Parameter Estimation From Attenuated SPECT Projection Measurements", IEEE Transactions on Nuclear Science, 45(6): 3007-3013, 1998.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002. Not PA in 20355; Not PA in 21303; Suppl. IDS II in 25855; Suppl. IDS in 29684/25571/27030/28541.
Jeanguillaume et al. "From the Whole-Body Counting to Imaging: The Computer Aided Collimation Gamma Camera Project (CACAO)", Radiation Projection Dosimetry 89(3-4): 349-352, 2000.
Quartuccia et al. "Computer Assisted Collimation Gama Camera: A New Approach to Imaging Contaminated Tissues", Radiation Projection Dosimetry, 89(3-4): 343-348, 2000.
Piperno et al. "Breast Cancer Screening by Impedance Measurements", Frontiers Med. Biol. Engng., 2(2): 11-17, 1990.
Rajshekhar "Continuous Impedance Monitoring During CT-Guided Stereotactic Surgery: Relative Value in Cystic and Solid Lesions", British Journal of Neurosurgery, 6: 439-444, 1992.
Jessup "Tumor Markers—Prognostic and Therapeutic Implications for Colorectal Carcinoma", Surgical Oncology, 7: 139-151, 1998.
Corstens et al. "Nuclear Medicine's Role in Infection and Inflammation", The Lancet, 354: 765-770, 1999.
Mori et al. "Overexpression of Matrix Metalloproteinase-7mRNA in Human Colon Carcinomas", Cancer, 75: 1516-1519, 1995.
Erbil et al. "Use and Limitations of Serum Total and Lipid-Bound Sialic Acid Concentrations as Markers for Colorectal Cancer", Cancer, 55: 404-409, 1985.

Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Day et al. "Localization of Radioiodinated Rat Fibrogen in Transplanted Rat Tumors", Journal of the National Cancer Institute, 23(4): 799-812, 1959.
Bromiley et al. "Attenuation Correction in PET Using Consistency Conditions and A Three-Dimensional Template", IEEE Transactions on Nuclear Science, 48(4): 1371-1377, 2001. p. 1376, Col. 2, § 2.
Hayakawa et al. "A PET-MRI Registration Technique for PET Studies of the Rat Brain", Nuclear Medicine & Biology, 27: 121-125, 2000. p. 121, col. 1.
Lavallée et al. "Building A Hybrid Patient's Model for Augmented Reality in Surgery: A Registration Problem", Computing in Biological Medicine, 25(2): 149-164, 1995. p. 149-150.
Kojima et al. "Quantitative Planar Imaging Method for Measurement of Renal Activity by Using A Conjugate-Emission Image and Transmission Data", Medical Physics, 27(3): 608-615, 2000. p. 608.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.
Communication Pursuant to Article 94(3) EPC Dated Sep. 22, 2011 From the European Patent Office Re. Application No. 06756258.7.
Notice of Allowance Dated Sep. 16, 2011 From the US Patent and Trademark Office Re.: U.S. Appl. No. 11/607,075.
Official Action Dated Sep. 12, 2011 From the US Patent and Trademark Office Re. U.S. Appl. No. 11/980,653.
Official Action Dated Sep. 12, 2011 From the US Patent and Trademark Office Re. U.S. Appl. No. 12/087,150.
Official Action Dated Sep. 13, 2011 From the US Patent and Trademark Office Re. U.S. Appl. No. 11/976,852.
Response Dated Sep. 12, 2011 to Official Action of Jul. 11, 2011 From the Its Patent and Trademark Office Re.: U.S. Appl. No. 11/980,683.
Response Dated Sep. 20, 2011 to Official Action of Apr. 20, 2011 From the US Patent and Trademark Office Re.: U.S. Appl. No. 11/798,017.
Ellestad "Stress Testing: Principles and Practice", XP008143015, 5th Edition, p. 432, Jan. 1, 2003.
Gilland et al. "Long Focal Length, Asymmetric Fan Beam Collimation for Transmission Acquisition With A Triple Camera SPECT System", IEEE Transactions on Nuclear Science, XP011087666, 44(3): 1191-1196, Jun. 1, 1997.
Meyers et al. "Age, Perfusion Test Results and Dipyridamole Reaction", Radiologic Technology, XP008142909, 73(5): 409-414, May 1, 2002.
Zhang et al. "Potential of A Compton Camera for High Performance Scintimammography", Physics in Medicine and Biology, XP020024019, 49(4): 617-638, Feb. 21, 2004.
Official Action Dated Jul. 12, 2011 From the US Patent and Trademark Office Re.: U.S. Appl. No. 09/641,973.
Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Supplemental Notice of Allowability Dated Oct. 24, 2011 From the US Patent and Trademark Office Re.: U.S. Appl. No. 11/607,075.
Notice of Allowance Dated Oct. 11, 2011 From the US Patent and Trademark Office Re. U.S. Appl. No. 11/988,926.
Response Dated Oct. 14, 2011 to Communication Pursuant to Rules 70(2) and 70a(2) EPC of Apr. 4, 2011 From the European Patent Office Re. Application No. 05803689.8.

Restriction Official Action Dated Nov. 8, 2011 From the US Patent and Trademark Office Re. U.S. Appl. No. 12/309,479.
Response Dated Nov. 14, 2011 to Official Action of Sep. 12, 2011 From the US Patent and Trademark Office Re. U.S. Appl. No. 12/087,150.
Response Dated Oct. 24, 2011 to Official Action of May 23, 2011 From the US Patent and Trademark Office Re. U.S. Appl. No. 11/667,793.
Restriction Official Action Dated Nov. 15, 2011 From the US Patent and Trademark Office Re. U.S. Appl. No. 11/980,683.
Communication Pursuant to Article 94(3) EPC Dated Nov. 18, 2011 From the European Patent Office Re. Application No. 05803689.8.
Response Dated Nov. 14, 2011 to Official Action of Jul. 12, 2011 From the US Patent and Trademark Office Re.: U.S. Appl. No. 09/641,973.
Response Dated Nov. 23, 2011 to Official Action of May 23, 2011 From the US Patent and Trademark Office Re.: U.S. Appl. No. 10/616,307.
Response Dated Nov. 23, 2011 to Official Action of May 23, 2011 From the US Patent and Trademark Office Re.: U.S. Appl. No. 11/980,690.
Response Dated Dec. 8, 2011 to Restriction Official Action of Nov. 8, 2011 From the US Patent and Trademark Office Re. U.S. Appl. No. 12/309,479.
Official Action Dated May 23, 2011 From the US Patent and Trademark Office Re. U.S. Appl. No. 11/667,793.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Chengazi et al. "Imaging Prostate Cancer With Technetium-99m-7E11-C5.3 (CYT-351)", Journal of Nuclear Medicine, 38: 675-682, 1997.
McJilton et al. "Protein Kinase C$\epsilon$ Interacts With Bax and Promotes Survival of Human Prostate Cancer Cells", Oncogene, 22; 7958-7968, 2003.
Nu et al. "Quantitative Expression Profile of Androgen-Regulated Genes in Prostate Cancer Cells and Identification of Prostate-Specific Genes", International Journal of Cancer, 92: 322-328, 2001.
Interview Summary Dated May 31, 2011 From the US Patent and Trademark Office Re. U.S. Appl. No. 10/616,301.
Notice of Allowance Dated Jun. 23, 2011 From the US Patent and Trademark Office Re.: U.S. Appl. No. 10/616,301.
Examination Report Dated Jun. 22, 2011 From the Government of India, Patent Office, Intellectual Property Building Re. Application No. 2963/CHENP/2006.
Official Action Dated Mar. 9, 2011 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.
Response Dated Jun. 28, 2011 to Official Action of Dec. 28, 2010 From the US Patent and Trademark Office Re.: U.S. Appl. No. 11/607,075.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Response Dated Oct. 14, 2011 to Supplementary European Search Report and the European Search Opinion of Mar. 16, 2011 From the European Patent Office Re. Application No. 05803689.8.
Official Action Dated Dec. 15, 2011 From the US Patent and Trademark Office Re.: U.S. Appl. No. 10/343,792.
Official Action Dated Dec. 20, 2011 From the US Patent and Trademark Office Re. U.S. Appl. No. 12/309,479.
Response Dated Nov. 13, 2011 to Official Action of Sep. 12, 2011 From the US Patent and Trademark Office Re. U.S. Appl. No. 11/980,653.
Response Dated Dec. 29, 2011 to Office Action of Jul. 17, 2007 From the Israeli Patent Office Re.: Application No. 154323.
Berman et al. "Dual-Isotope Myocardial Perfusion Spect With Rest Thallium-201 and Stress Tc-99m Sestamibi", Cardiology Clinics, 12(2): 261-270, May 1994.
DeGrado et al. "Topics in Integrated Systems Physiology. Tracer Kinetic Modeling in Nuclear Cardiology", Journal of Nuclear Cardiology, 7: 686-700, 2000.
Links "Advances in SPECT and PET Imaging", Annals in Nuclear Medical Science, 13(2): 107-120, Jun. 2000.
Official Action Dated Jan. 19, 2012 From the US Patent and Trademark Office Re. U.S. Appl. No. 11/667,793.
Official Action Dated Jan. 23, 2012 From the US Patent and Trademark Office Re. U.S. Appl. No. 12/087,150.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Toennies et al. "Scatter Segmentation in Dynamic SPECT Images Using Principal Component Analysis", Progress in Biomedical Optics and Imaging, 4(23): 507-516, 2003.

* cited by examiner

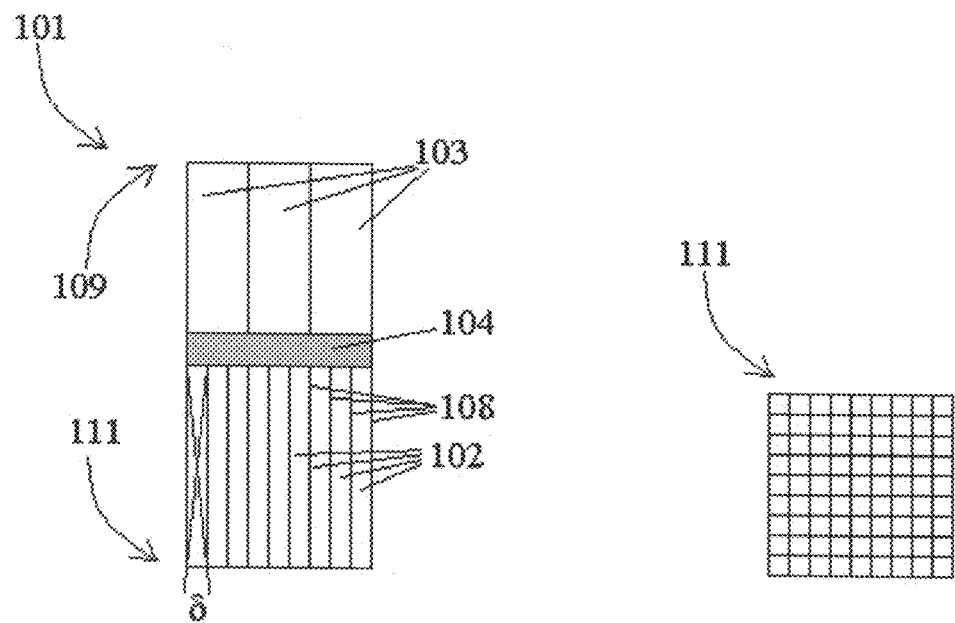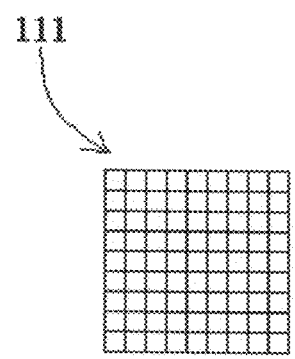
Figure 1e
Figure 1f
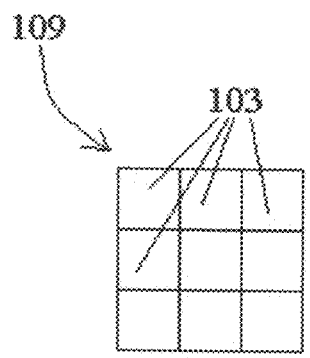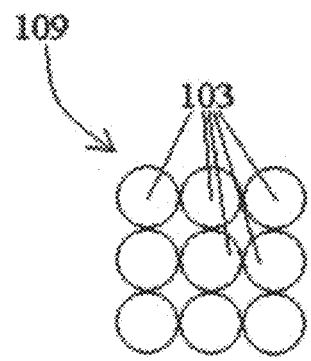
Figure 1g
Figure 1h

METHODS OF VIEW SELECTION FOR RADIOACTIVE EMISSION MEASUREMENTS

RELATED APPLICATIONS

This application is a National Phase Application of PCT Application No. PCT/IL2005/000572 having International Filing Date of Jun. 1, 2005, which claims the benefit of US Provisional Patent Application No. 60/575,369, filed on Jun. 1, 2004, US Provisional Patent Application No. 60/625,971, filed on Nov. 9, 2004, US Provisional Patent Application No. 60/630,561, filed on Nov. 26, 2004, US Provisional Patent Application No. 60/632,236, filed on Dec. 2, 2004, US Provisional Patent Application No. 60/632,515, filed on Dec. 3, 2004, US Provisional Patent Application No. 60/635,630, filed on Dec. 14, 2004, US Provisional Patent Application No. 60/636,088, filed on Dec. 16, 2004, US Provisional Patent Application No. 60/640,215, filed on Jan. 3, 2005, US Provisional Patent Application No. 60/648,385, filed on Feb. 1, 2005, US Provisional Patent Application No. 60/648,690, filed on Feb. 2, 2005. The contents of the above Applications are all incorporated herein by reference.

FIELD AND BACKGROUND OF THE INVENTION

The present invention relates to selecting optimal views for measuring radiation emitted by an object. More particularly, the present invention relates to selecting the optimal views using a scoring function based on information-theoretic measures. Of particular interest is view selection for medical imaging and/or in conjunction with medical instruments, such as guided minimally invasive surgical instruments.

Radionuclide imaging is one of the most important applications of radioactivity in medicine. Its purpose is to obtain a distribution image of a radioactively labeled substance, e.g., a radiopharmaceutical, within the body following administration thereof to a patient. Radioactive-emission imaging relies on the fact that in general, pathologies, such as malignant tumors, malfunctioning organs, and inflammations, display a level of activity different from that of healthy tissue. Thus, radiopharmaceuticals, which circulate in the blood stream, are picked up by the active pathologies to a different extent than by the surrounding healthy tissue; in consequence, the pathologies are operative as radioactive-emission sources and may be detected by radioactive-emission imaging. It will be appreciated that the pathology may appear as a concentrated source of high radiation, a hot region, as may be associated with a tumor, or as a region of low-level radiation, which is nonetheless above the background level, as may be associated with carcinoma.

A reversed situation is similarly possible. Dead tissue has practically no pick up of radiopharmaceuticals, and is thus operative as a cold region.

Thus radiopharmaceuticals may be used for identifying active pathologies as well as dead tissue.

In the discussion that follows, the term organ target is intended to include pathological features within organs. These pathological features may be expressed, by radioactive-emission imaging, as any one of the following:

i. hot regions, of a radioactive emission intensity higher than the background level;
ii. regions of low-level radioactive emission intensity, which is nonetheless above the background level; and
iii cold regions, of a radioactive emission intensity, lower than the background level.

Examples of radiopharmaceuticals include monoclonal antibodies or other agents, e.g., fibrinogen or fluorodeoxyglucose, tagged with a radioactive isotope, e.g., $^{99M}$technetium, $^{67}$gallium, $^{201}$thallium, $^{111}$indium, $^{123}$iodine, $^{125}$iodine and $^{18}$fluorine, which may be administered orally or intravenously. The radiopharmaceuticals are designed to concentrate in the area of a tumor, and the uptake of such radiopharmaceuticals in the active part of a tumor, or other pathologies such as an inflammation, is higher and more rapid than in the tissue that neighbors the tumor. Thereafter, a radiation-emission-measuring-probe, which may be configured for extracorporeal or intracorporeal use, is employed for locating the position of the active area. Another application is the detection of blood clots with radiopharmaceuticals such as ACUTECT from Nycomed Amersham for the detection of newly formed thrombosis in veins, or clots in arteries of the heart or brain, in an emergency or operating room. Yet other applications include radioimaging of myocardial infarct using agents such as radioactive anti-myosin antibodies, radioimaging specific cell types using radioactively tagged molecules (also known as molecular imaging), etc.

The usual preferred emission for such applications is that of gamma rays, which emission is in the energy range of approximately 11-511 KeV. Beta radiation and positrons may also be detected.

Radioactive-emission imaging is performed with a radioactive-emission-measuring detector, such as a room temperature, solid-state CdZnTe (CZT) detector, which is among the more promising that is currently available. It may be configured as a single-pixel or a multi-pixel detector, and may be obtained, for example, from eV Products, a division of II-VI Corporation, Saxonburg Pa., 16056, or from IMARAD IMAGING SYSTEMS LTD., of Rehovot, ISRAEL, 76124, www.imarad.com, or from another source. Alternatively, another solid-state detector such as CdTe, HgI, Si, Ge, or the like, or a combination of a scintillation detector (such as NaI(Tl), LSO, GSO, CsI, CaF, or the like) and a photomultiplier, or another detector as known, may be used.

FIGS. 1a-1i schematically illustrate detecting units 102 and detecting blocks 101 of various geometries and constructions, and radioactive-emission-measuring probes associated with them.

FIG. 1a schematically illustrates a detecting unit 102, formed as a single-pixel detector 104, for example, a room-temperature solid-state CdZnTe (CZT) detector, having a diameter D and a thickness $\tau_d$. Both the detector diameter D, or a diameter equivalent in the case of a non-circular detector, and the detector thickness $\tau_d$ affect the detecting efficiency. The detector diameter determines the surface area on which radioactive emission impinges; the greater the surface area, the greater the efficiency. The detector thickness affects the stopping power of the detector. High energy gamma rays may go through a thin detector, and the probability of their detection increases with detector thickness. By itself, a single-pixel detector cannot generate an image; rather, all counts are distributed over the surface area of the detector.

FIG. 1b schematically illustrates the detecting unit 102 with a collimator 108, formed as a single cell of a diameter D, a length L, and a septa thickness $\tau$, attached to the detector 104. The collimator 108 may be, for example, of lead, tungsten or another material which substantially blocks gamma and beta rays.

The collimator's geometry, and specifically, the ratio of D/L, provides the detecting unit 102 with a collection angle $\delta$ analogous to a viewing angle of an optical camera. The collection angle $\delta$ limits the radioactive-emission detection to substantially only that radioactive emission, which impinges on the detector 104 after passing through a "corridor" of the collimator 108 (although in practice, some high-energy gamma rays may penetrate the collimator's walls).

FIG. 1c schematically illustrates a block 101 of the detecting units 102, with the collimator 108, formed as a multi-cell collimator, of a cell diameter D. The collection angle δ is defined for each of the detecting units 102 in the block, and each of the detecting units 102 forms a pixel in the block 101.

FIG. 1d schematically illustrates a radioactive-emission-measuring probe 100 which comprises several detecting units 102, of different geometries and different collection angles δ, within a housing 107.

FIGS. 1e-1i schematically illustrate the block 101, formed as a combination of a scintillation detector (such as NaI(Tl), LSO, GSO, CsI, CaF, or the like), a collimator grid, and photomultipliers.

As seen in FIG. 1e, the block 101, having proximal and distal ends 109 and 111, respectively, vis a vis an operator (not shown), is formed of the scintillation detector 104, of a single pixel, and the collimators 108, to create the detecting units 102. A plurality of photomultipliers 103 is associated with the single pixel scintillation detector 104, and with proper algorithms, as known, their output can provide a two dimensional image of the scintillations in the single pixel scintillation detector 104. In essence, this is an Anger camera, as known.

The distal view 111 of the collimator grid is seen in FIG. 1f.

Two optional proximal views 109 of the photomultipliers 103 are seen in FIGS. 1g and 1h, as a square grid arrangement, and as an arrangement of tubes.

An Anger camera 117, of the block 101 in the housing 107 is seen in FIG. 1i.

In each of the cases of FIGS. 1a-1i, the geometry of the collimator 108 determines the collection angle δ, wherein with no collimator, the collection angle δ, is essentially a solid angle of 4π steradians. Thus, the collimator's geometry affects both the detection efficiency and the image resolution, which are defined as follows:

i. The detection efficiency is the ratio of measured radiation to emitted radiation; and ii. The image resolution is the capability of making distinguishable closely adjacent radioactive-emission organ targets, or the capability to accurately determine the size and shape of individual radioactive-emission organ targets.

Naturally, it is desired to optimize both the detection efficiency and the image resolution. Yet, they are inversely related to each other. The detection efficiency increases with increasing collimator's collection angle, and the image resolution decreases with increasing collimator's collection angle. For example, when the ratio of D/L is 1/2, the collection angle δ is substantially 2.5 steradians, so the cell views incident radiation within the confinement of about a 2.5-steradian sector. However, when the ratio of D/L is 1/12, the collection angle δ is substantially 0.31 steradians, so the cell views incident radiation within the confinement of about a 0.31-steradian sector.

Once the emission data is obtained, the data is processed to reconstruct the intensity distribution within the measured volume. The reconstruction process is generally complex, due to the large quantity of data which must be processed in order to obtain an accurate reconstruction. The following prior art statistical model may be used to perform reconstruction.

We assume an intensity distribution, I, defined over an input space U, where U comprises a set of basic elements (e.g., pixels in two dimensional spaces, voxels in three dimensional spaces), and I(u) is the intensity of a given basic element $u \in U$. A detecting unit positioned on a radiation-emission-measuring-probe takes a series of measurements $y=(y_t)_{t=1}^T$ from different positions and orientations around the volume U. The geometrical and physical properties of the detecting unit, together with its position and orientation in a given measurement t, determine the detection probability $\phi_t(u)$ of a photon emitted from location u. Thus the effective intensity of location u as viewed by the detecting unit during measurement t is $\phi_t(u)I(u)$.

The random count $X_t(u)$ of photons that are emitted from location u and detected in measurement t is modeled by a Poisson process with mean $\phi_t(u)I(u)$. The total count of photons detected in measurement t is $Y_t = \Sigma_{u \in U} X_t(u)$, and the reconstruction problem is to reconstruct the intensities $(I(u))_{u \in U}$ from the measurements $(y_t)_{t=1}^T$.

The 2-D Radon transform is a mathematical relationship which may be used to reconstruct the emission intensities of volume U when the set of measurements $(y_t)_{t=1}^T$ is unconstrained. The Radon transform is not statistical and does not take into account the Poissonian nature of the counts. In addition, it models the views as line projections. The Radon transform maps the spatial domain (x,y) to the Radon domain (p,φ). For a fixed projection angle, the Radon transform is simply a projection of the object. A technique known in the art as filtered back-projection (FBP) uses a back-projection operator and the inverse of the Radon transform to reconstruct the intensity distribution in volume U from measurements $(y_t)_{t=1}^T$.

The basic, idealized problem solved by the FBP approach is to reconstruct an image from its Radon transform. The Radon transform, when properly defined, has a well-defined inverse. However, in order to invert the transform one needs measured data spanning 180°. In many medical imaging situations, the positioning of the detecting unit relative to the emitting object is constrained, so that complete measured data is not available. Reconstruction based on filtered back-projection is therefore of limited use for medical imaging. Maximum likelihood (ML) and Maximum A Posteriori (MAP) estimation methods, which address the statistical nature of the counts, have been found to provide better image reconstructions than FBP.

Limited-angle tomography is a reconstruction technique in the related art which reconstructs an image from projections acquired over a limited range of angular directions. The success of the reconstruction process depends upon the extent of the angular range acquired compared with the angular range of the missing projections. Any reconstruction from a limited range of projections potentially results in spatial distortions (artifacts) in the image. Limited angle techniques can be applied for both the Radon transform and the statistical models, but better results are generally achieved within the statistical framework. While it is known that the severity of the artifacts increases with the increasing angular range of the missing projections, limited-angle tomography does not provide information on which projections should be used in order to most effectively reconstruct the image.

Maximum likelihood (ML) estimation is a widely used method in the related art for reconstructing an image from a constrained set of measurements. A parameterization of the generative model described above is obtained by assigning an intensity I(u) to every voxel in U. The likelihood of the observed data $y=(y_t)_t$ given the set of parameters I={I(u): $u \in U$} is:

$$L(y \mid I) = \ln P(y \mid I) = \ln \prod_t P(y_t \mid I) = \sum_t \ln P\left(\sum_u x_t(u) \mid I\right)$$

$$= \sum_t \ln \text{Poisson}\left(y_t \mid \sum_u \phi_t(u) I(u)\right)$$

$$= \sum_t \left\{ \begin{array}{l} -\sum_u \phi_t(u) I(u) + \\ y_t \ln \sum_u \phi_t(u) I(u) - \ln(y_t!) \end{array} \right\}$$

Note that the lower and upper bound of an indexing variable (such as voxels u and time index t) are omitted in the following description, when they are clear from the context.

There is currently no analytic way to solve Eqn. 1 for the maximum of the likelihood function. However, optimization methods that find local maxima of the likelihood are known. One such method is the Expectation-Maximization (EM) process.

Since the data generated by the model is only partially observable by our measurements, a basic ingredient of the Expectation-Maximization formalism is to define a set of random variables that completely define the data generated by the model. In the current case, since $Y_t = \Sigma_u X_t(u)$, the set of variables $\{Xu(t): U \in U; t=1, \ldots, T\}$ is such a set; the generated data is $x=(x_t)_t$, where $x_t=(x_t(u))_u$, and the observed data y is completely determined by x. The main tool in the EM formalism is the complete data likelihood:

$$\ln P(x \mid I) = \ln \prod_t P(x_t \mid I) \quad (2)$$

$$= \sum_t \ln \prod_u \text{Poisson}(x_t(u) \mid \phi_t(u) I(u))$$

$$= \sum_t \sum_u \{-\phi_t(u) I(u) + x_t(u) \ln(\phi_t(u) I(u)) + \ln(x_t(u)!)\}$$

Since the likelihood depends on the complete data, which is only partially observable, we take its expectation with respect to the space of the unobserved data, given the current set of hypothesized parameters (i.e. the current estimator). The result is a function Q(I|I') which assigns likelihood to sets I of model parameters, given the current set I', and given the observed data y:

$$Q(I \mid I') = E[\ln P(x \mid I) \mid y; I'] \quad (3)$$

$$= \sum_t \sum_u \{-\phi_t(u) I(u) + E[x_t(u) \mid y_t; I']$$

$$\ln(\phi_t(u) I(u)) + C\}$$

where C is a term which is independent of the intensities I. The function Q(I|I') is maximized by the following new estimates:

$$I(u) = \frac{1}{\sum_t \phi_t(u)} \sum_t E[x_t(u) \mid y_t; I']; \forall u \in U. \quad (4)$$

The expectation in Equation 4 is obtained as follows:

$$P_{X_t(u)}(x_t(u) \mid y_t; I') = \frac{P_{Y_t}(y_t \mid x_t(u); I') P_{X_t(u)}(x_t(u) \mid I')}{P_{Y_t}(y_t \mid I')} \quad (5)$$

$$= \frac{\text{Poisson}\left(y_t - x_t(u) \mid \sum_{v \neq u} \phi_t(v) I'(v)\right) \text{Poisson}(x_t(u) \mid \phi_t(u) I'(u))}{\text{Poisson}\left(y_t \mid \sum_v \phi_t(v) I'(v)\right)}$$

$$= \text{Binomial}\left(x_t(u) \mid \frac{\phi_t(u) I'(u)}{\sum_v \phi_t(v) I'(v)}; y_t\right)$$

It follows that $$E[x_t(u) \mid y_t; I'] = y_t \frac{\phi_t(u) I'(u)}{\sum_v \phi_t(v) I'(v)},$$

and hence the EM iteration is:

$$I(u) = \frac{1}{\sum_t \phi_t(u)} \sum_t y_t \frac{\phi_t(u) I'(u)}{\sum_v \phi_t(v) I'(v)} \quad (6)$$

It is provable that each EM iteration improves the likelihood. Thus, given a random starting estimator, the EM algorithm iterates the above improvement step until it converges to a local maximum of the likelihood. Several random starts increase the chance of finding a globally good estimator.

It is usually desired to maximize the expected posterior probability (given a proper prior) rather than the expected likelihood. In that case we assume a prior probability on the intensities $P(I) = \pi_u P(I(u))$. A proper conjugate prior for the Poisson distribution is the Gamma distribution:

$$P(I(u)) = \text{Gamma}(I(u) \mid \alpha_u; \beta_u) \frac{\beta_u^{\alpha_u+1}}{\Gamma(\alpha_u + 1)} I(u)^{\alpha_u} e^{-\beta_u I(u)} \quad (7)$$

Now the maximization is done on Q(I|I')=E[lnP(x|I)p(I)|y; I']. Plugging the Gamma prior into Q, and solving for I(u), we get the following EM iteration for the maximum posterior estimation:

$$I(u) = \frac{\alpha_u + \sum_t E[x_t(u) \mid y_t; I']}{\beta_u + \sum_t \phi_t(u)} \quad (8)$$

$$= \frac{1}{\beta_u + \sum_t \phi_t(u)} \left[\alpha_u + \sum_t y_t \frac{\phi_t(u) I'(u)}{\sum_v \phi_t(u) I'(v)}\right]$$

The EM update step can be formulated in matrix notation as follows. Let $\Phi$ be the matrix of the projections $[\phi_t(u)]_{t,u}$, and let I,I',y, $\alpha$ and $\beta$ be represented as column vectors. Equation 8 can be written in vector and matrix notations as:

$$I = \frac{\alpha + I' \cdot \left(\Phi^T \frac{y}{\Phi I'}\right)}{\beta + \Phi^T 1} \quad (10)$$

where the explicit multiplication and division denote element-wise operations, and where 1 is a vector (of the appropriate length) consisting solely of 1's.

Limited computational resources (i.e., when the entire projection matrix $\Phi$ cannot be kept in memory) may require breaking the update computation according to a partition of $\Phi$ into a set of sub-matrices ($\Phi_i$). In that case the intensities can be updated gradually (using only one sub-matrix at each step) according to the following computation:

$$I = \frac{\alpha + I' \cdot \sum_i \phi_i^T \frac{y_i}{\Phi_i I'}}{\beta + \sum_i \Phi_i^T 1} \quad (11)$$

where $y_i$ is the vector of observations that are obtained using the views of $\Phi_i$.

In order to achieve a reconstructed image which is adequate for medical diagnostic and treatment purposes, a high-resolution image of the tested object must be obtained. When high-resolution detecting units are used, their efficiency is relatively low, and the detecting units must remain at each position for a relatively long time in order to achieve a high probability of detection. Since during medical testing, measurements are generally performed at many locations as the detecting unit is moved relative to the observed organ, the testing procedure generally requires a long time and is physically and emotionally difficult for the patient. Additionally, reconstruction is based upon a large quantity of data, and is a lengthy and computationally complex process.

SUMMARY OF THE INVENTION

A method is described for identifying an optimal, or preferred set of views for radioactive-emission measurements of a region of interest within the body. The method is based on a model of the region of interest, and the preferred sets of views are identified for the model, preferably using information theoretic measures. The preferred sets of views may then be applied to the region of interest, in vivo.

The present invention successfully addresses the shortcomings of the presently known configurations by providing methods for identifying optimal, or preferred sets of views for radioactive-emission measurements of a region of interest within the body. The methods are based on models of the region of interest, and the preferred sets of views are identified for the models, preferably using information theoretic measures. The preferred sets of views may then be applied to the region of interest, in vivo.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-1i show detecting units and blocks of various geometries and constructions and radioactive-emission-measuring probes, associated with them.

Figure 1A:
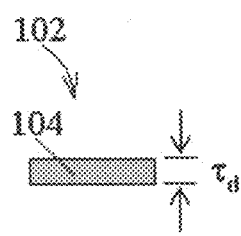
Figure 1B:
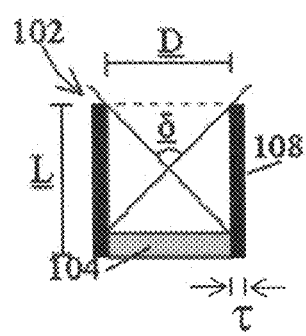
Figure 1C:
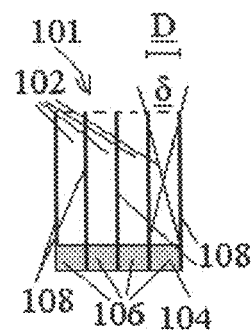
Figure 1D:
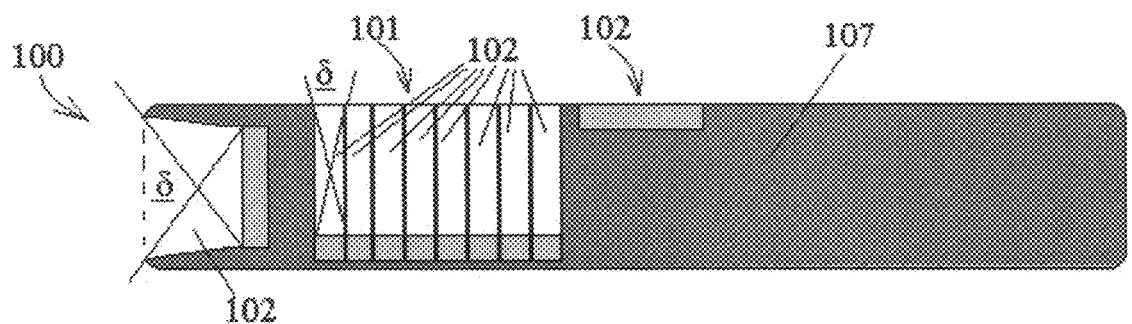
Figure 1I:
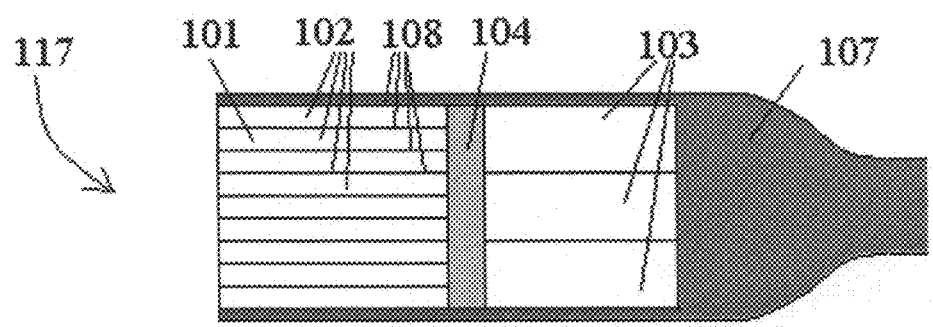
Figures 1J, 1K:
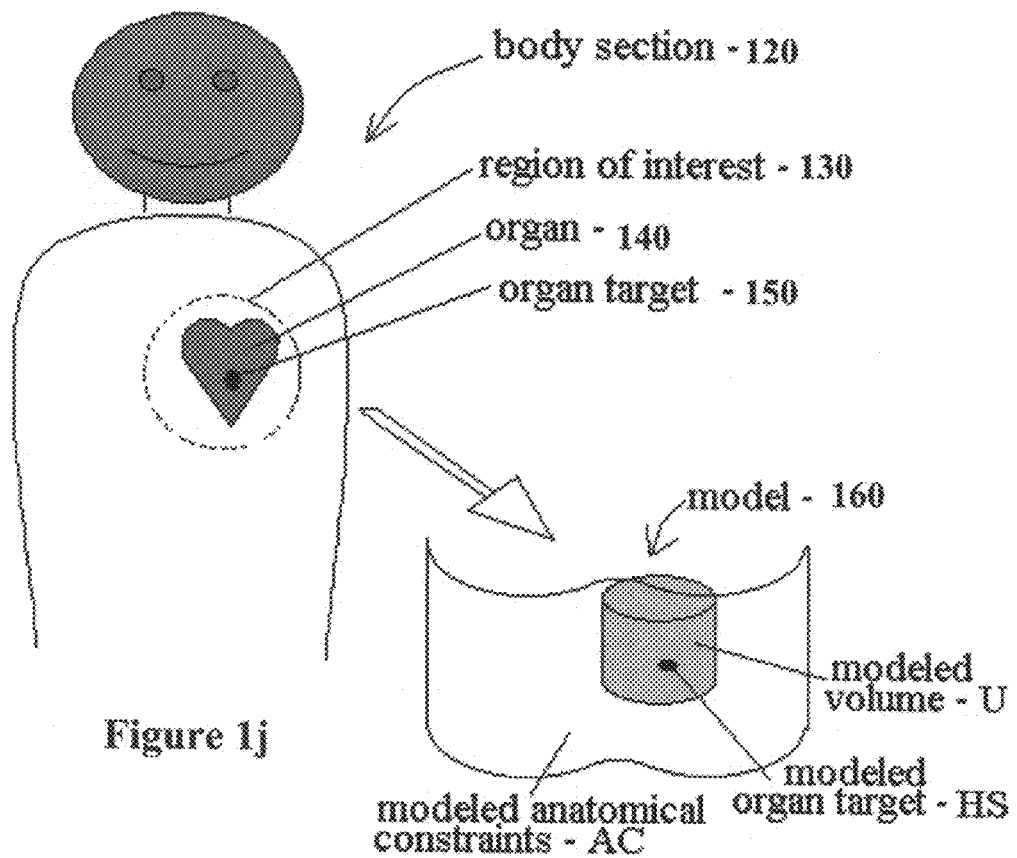
Figure 1L:
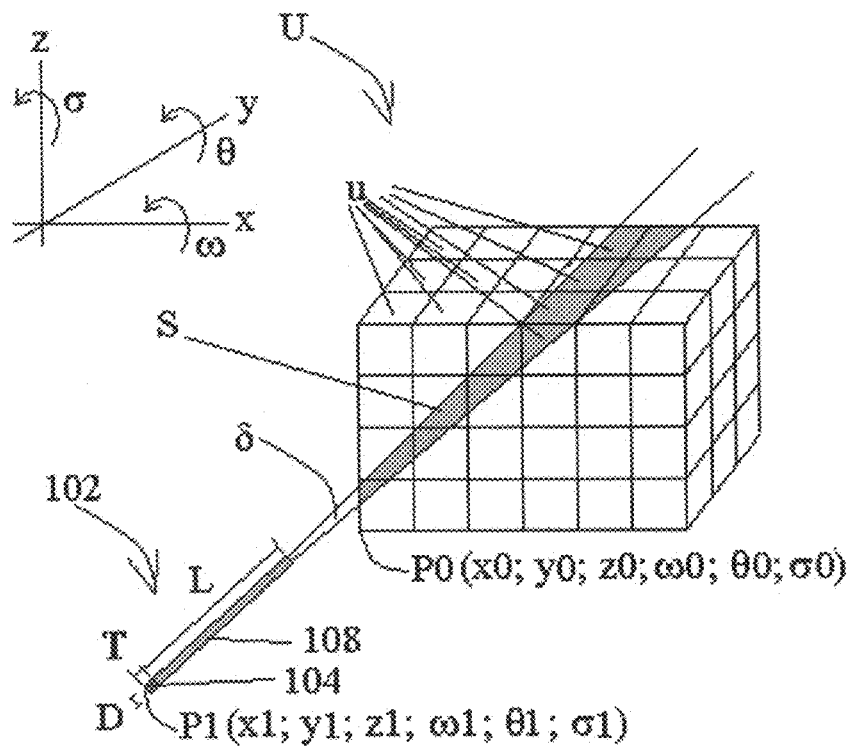
Figure 1M:
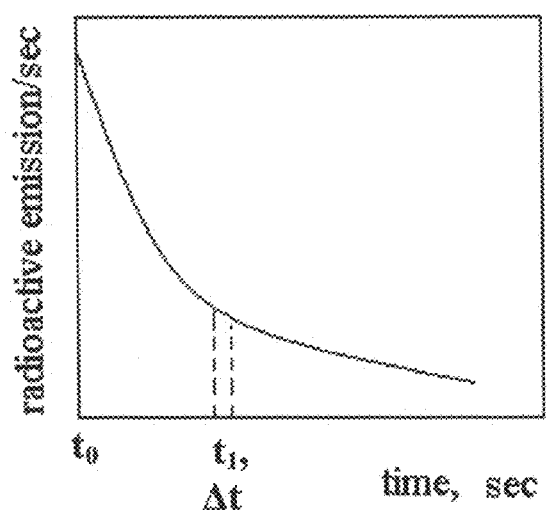

FIGS. 1j and 1k present the principles of modeling, for obtaining an optimal set of views, in accordance with the present invention;

FIGS. 1l and 1m pictorially illustrate a view and viewing parameters associated with it, in accordance with definitions of the present invention.

Figure 2:
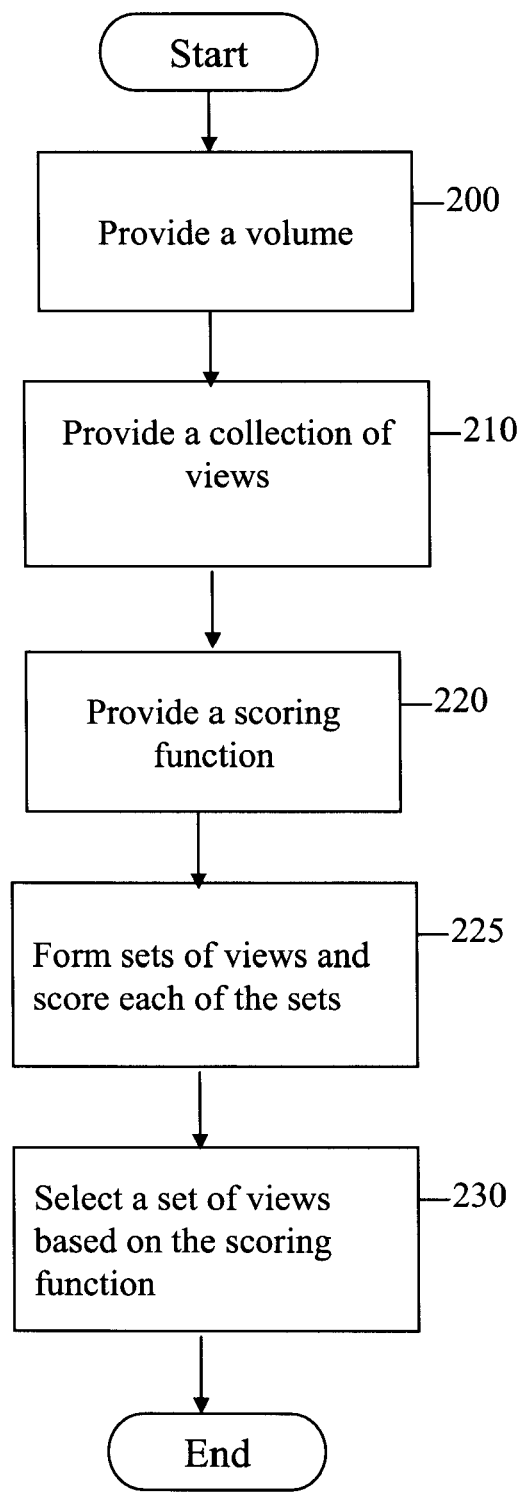

FIG. 2 is a simplified flowchart of a method for selecting a set of optimal views of a volume to be imaged, according to a first preferred embodiment of the present invention.

Figure 3:
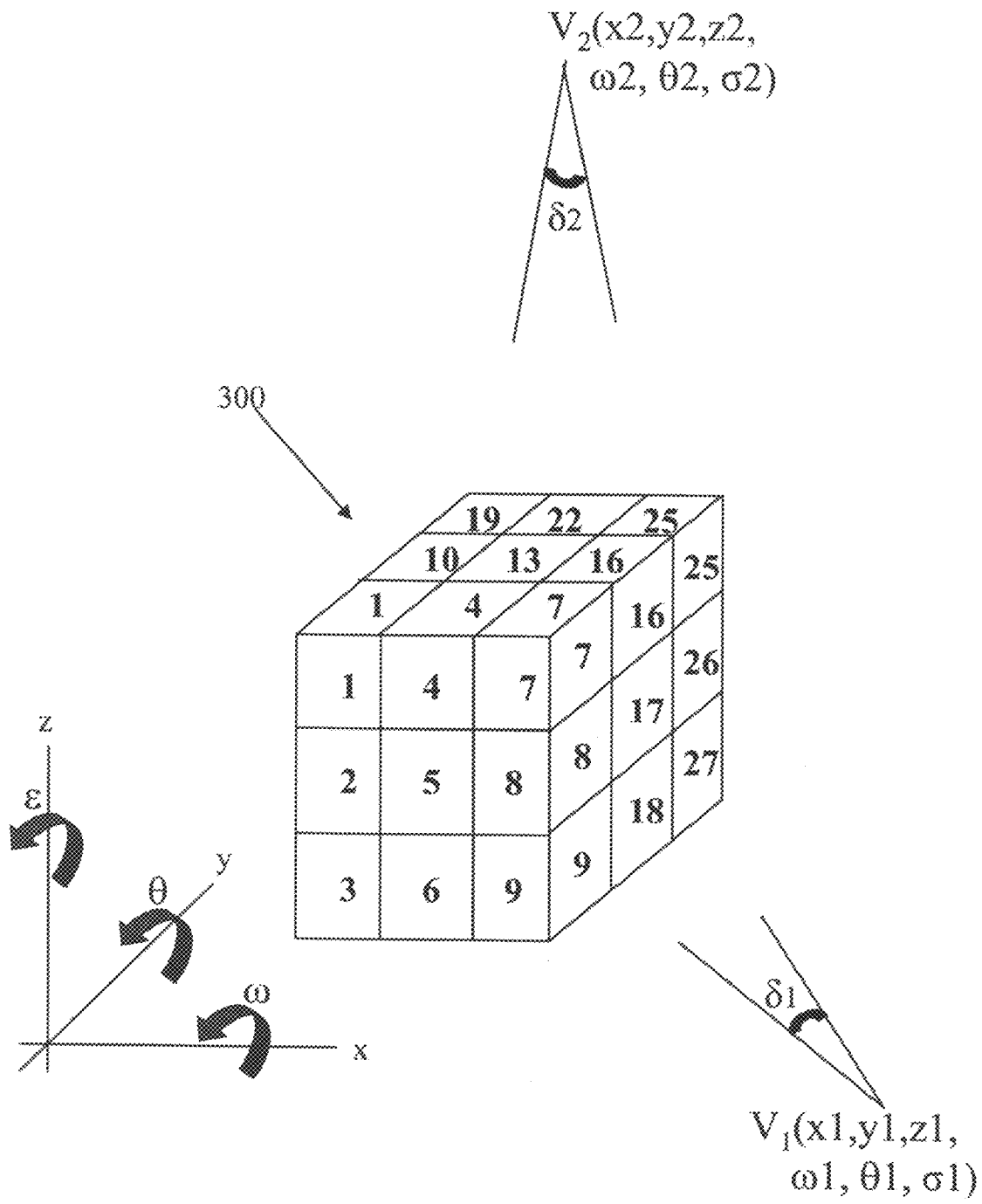

FIG. 3 shows an example of a volume with two views.

Figure 4:
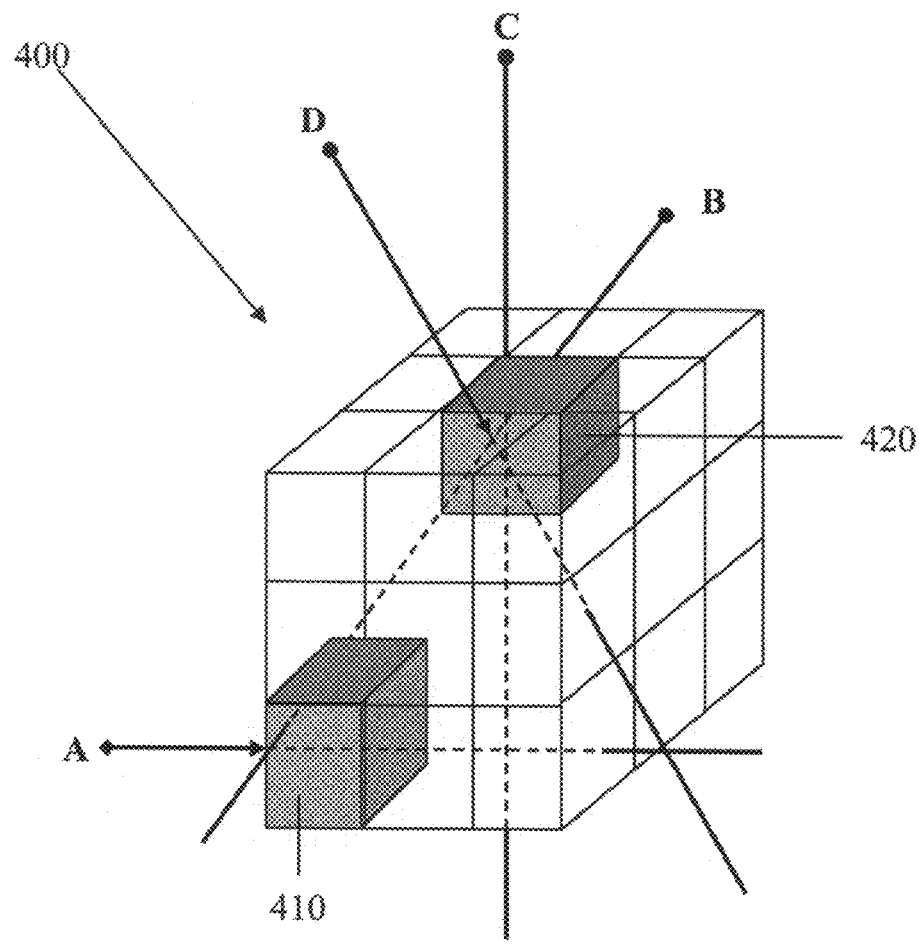

FIG. 4 illustrates the concept of uniform coverage of a volume.

Figure 5:
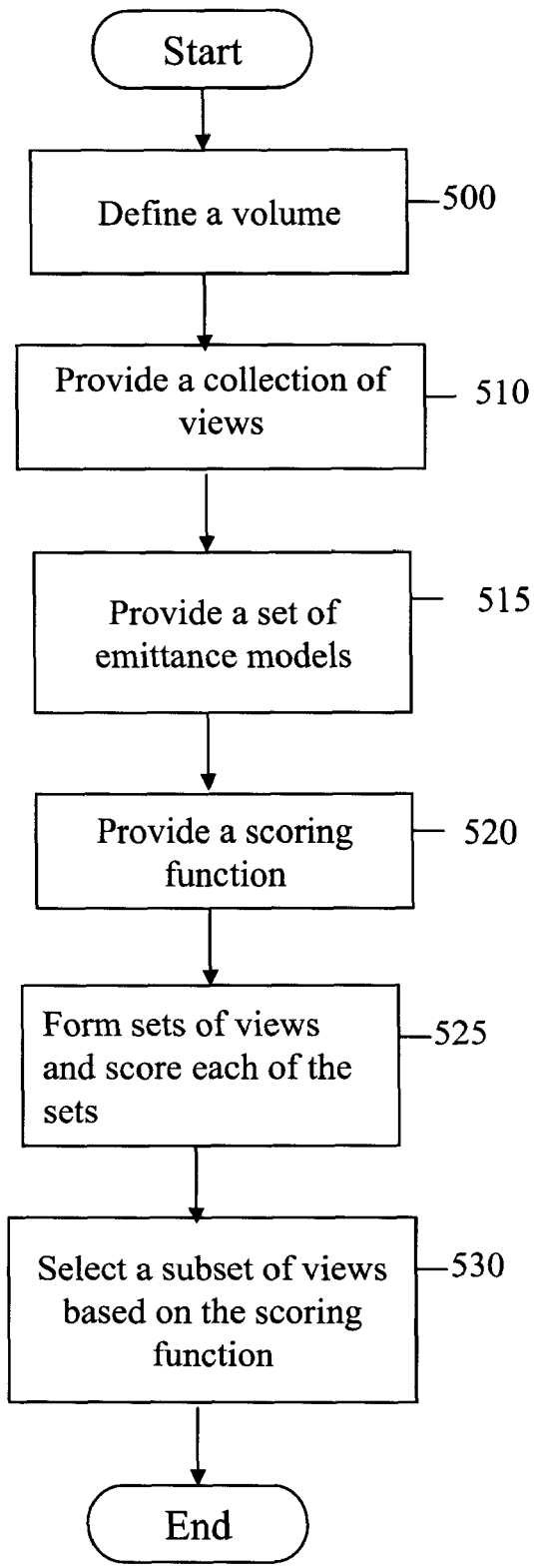

FIG. 5 is a simplified flowchart of a method for selecting a set of optimal views of a volume to be imaged, according to a second preferred embodiment of the present invention.

Figure 6:
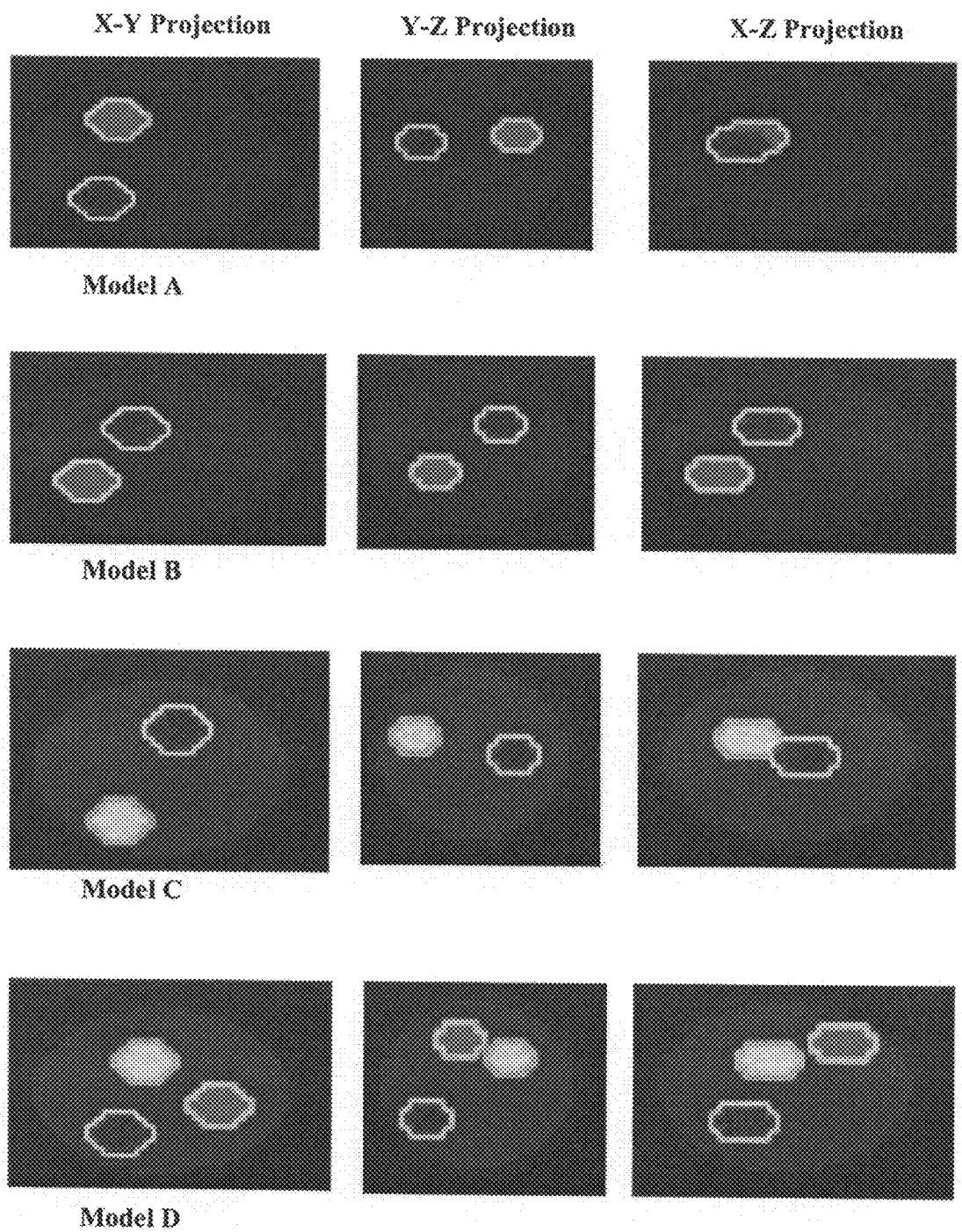

FIG. 6 shows four models of a prostate emittance model.

FIGS. 7a-7f show emittance models of a given volume to illustrate view selection using the separability criterion.

FIGS. 7g-7j show emittance models of a given volume to illustrate view selection using a weighted-combination criterion.

Figure 8:
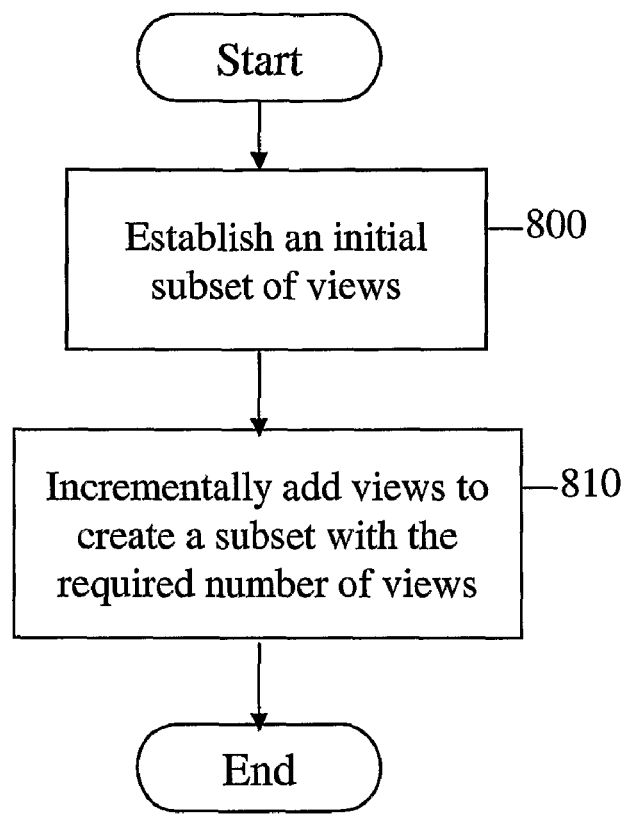

FIG. 8 is a simplified flowchart of an iterative method for selecting a set of views, according to a preferred embodiment of the present invention.

Figure 9:
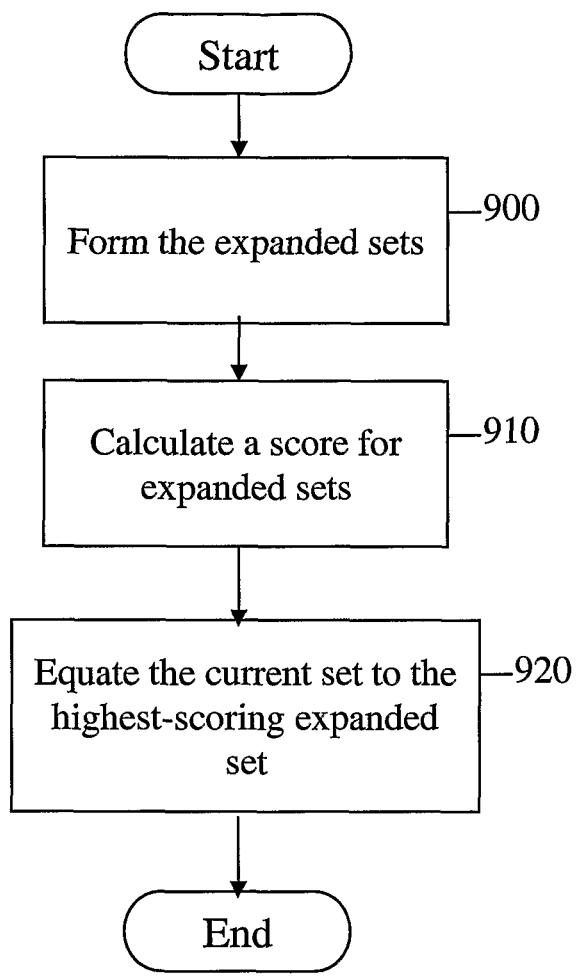

FIG. 9 is a simplified flowchart of a single iteration of a view selection method, according to a preferred embodiment of the present invention.

Figure 10:
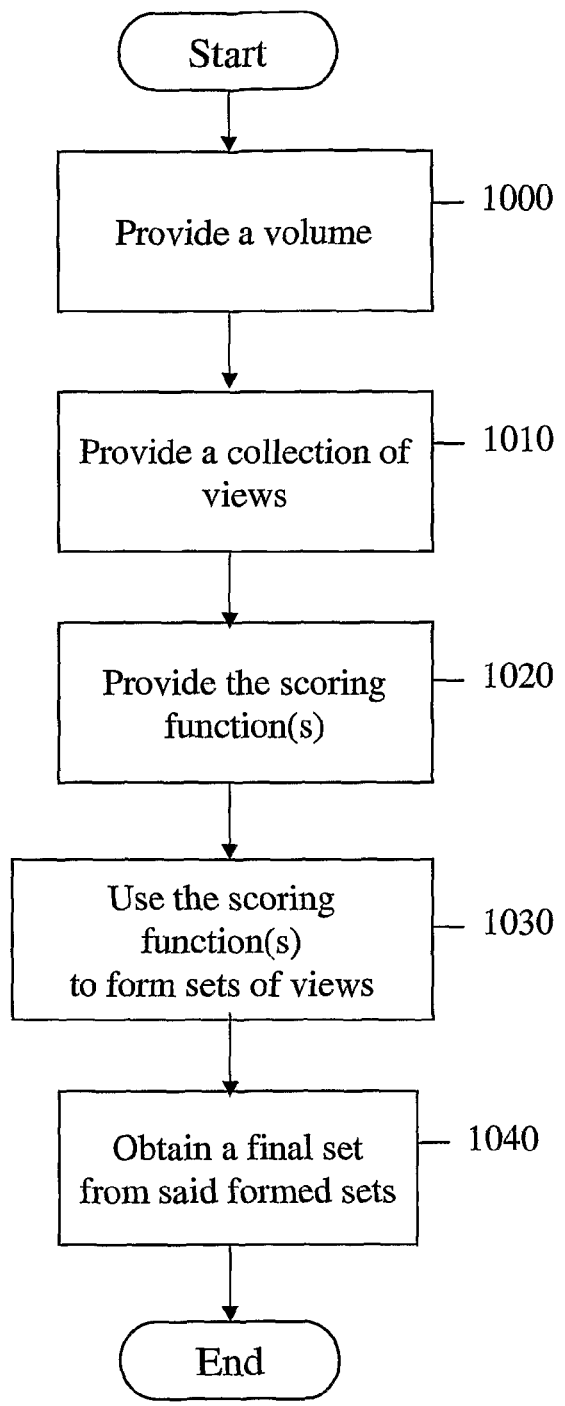

FIG. 10 is a simplified flowchart of a method for selecting a set of optimal views of a volume to be imaged, according to a third preferred embodiment of the present invention.

Figure 11:
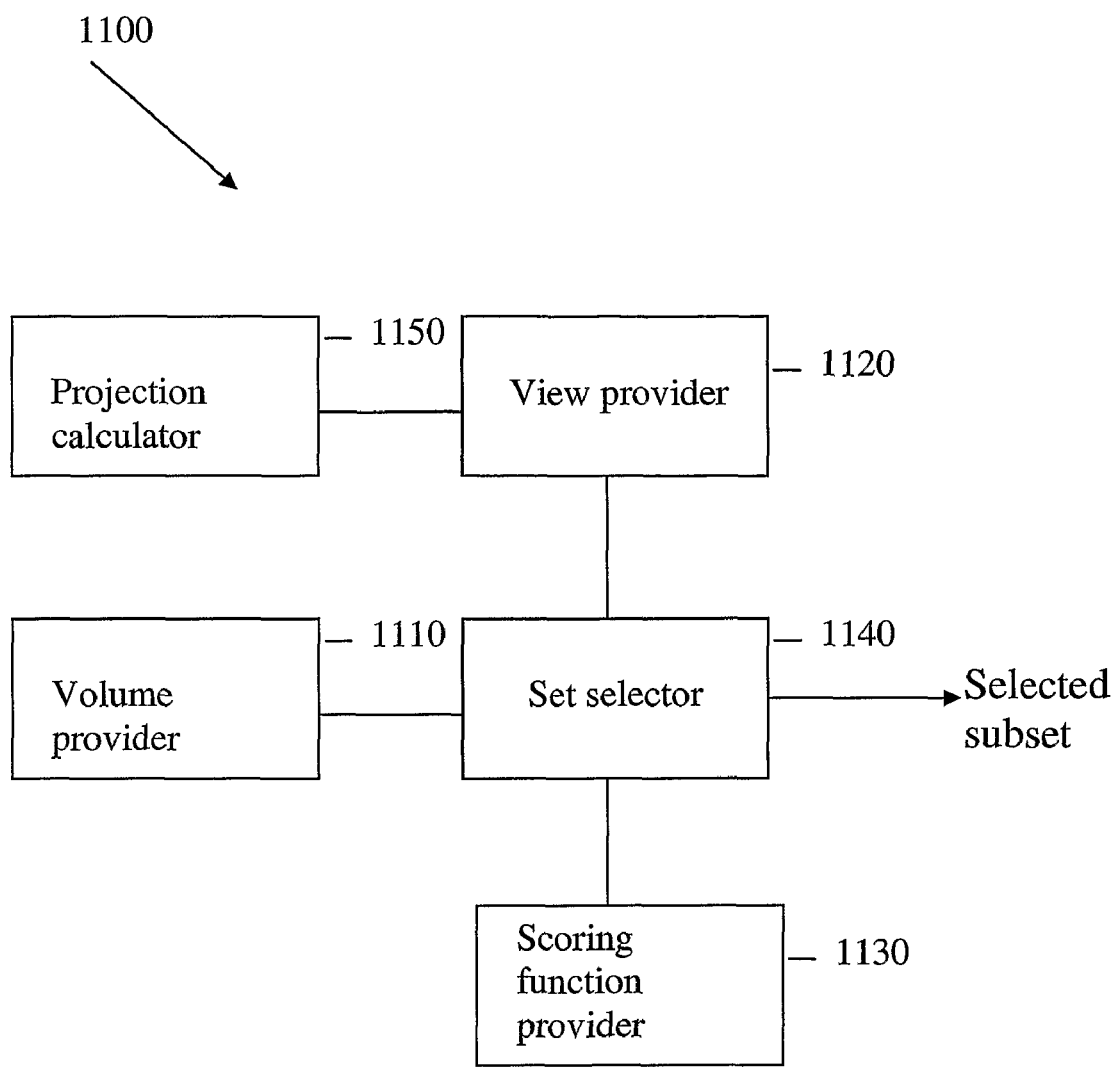

FIG. 11 is a simplified block diagram of a set selector for selecting a set of optimal views of a volume to be imaged, according to a first preferred embodiment of the present invention.

Figure 12:
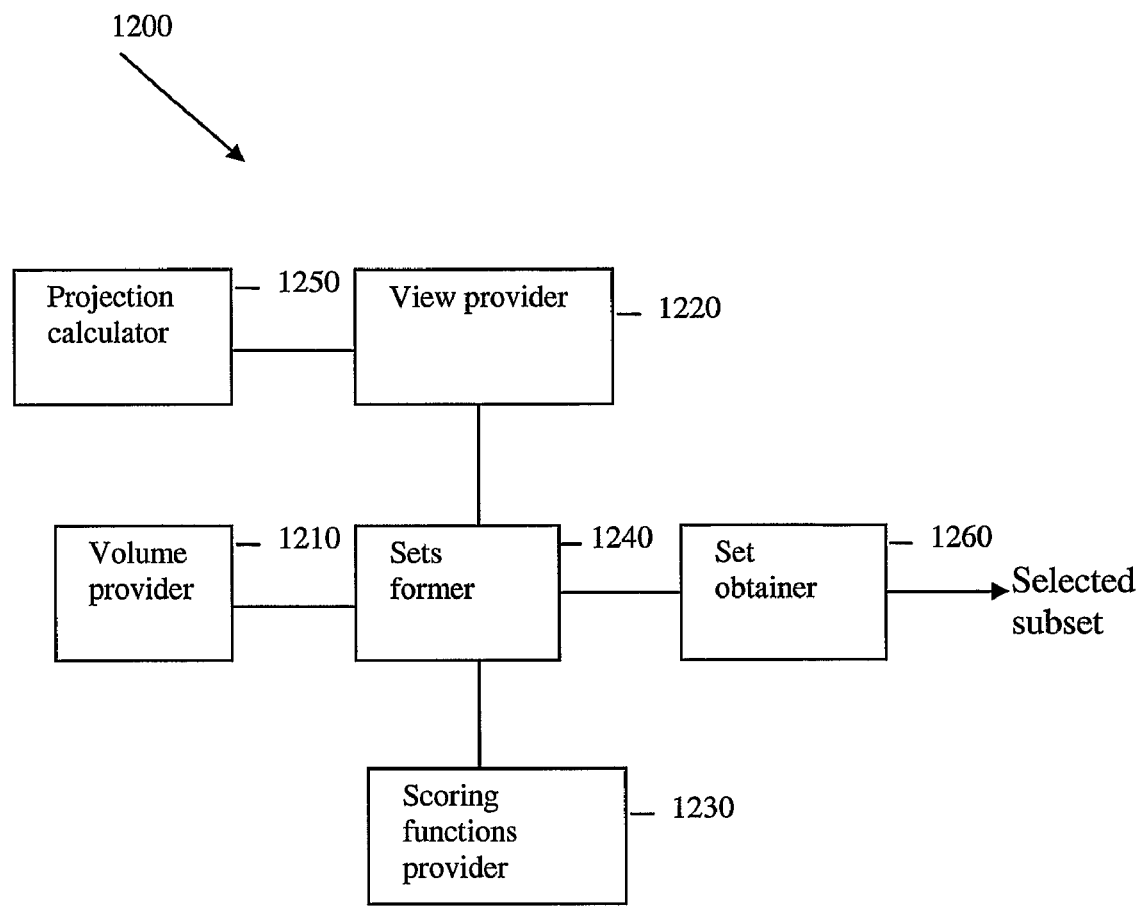

FIG. 12 is a simplified block diagram of a set selector for selecting a set of optimal views of a volume to be imaged, according to a second preferred embodiment of the present invention.

FIGS. 13-18 illustrate view set selection results for the uniformity criterion.

FIGS. 19-24 illustrate view set selection results for the separability criterion.

FIGS. 25-32 illustrate view set selection results for the reliability criterion, based on the Fisher information measure.

Figure 33:
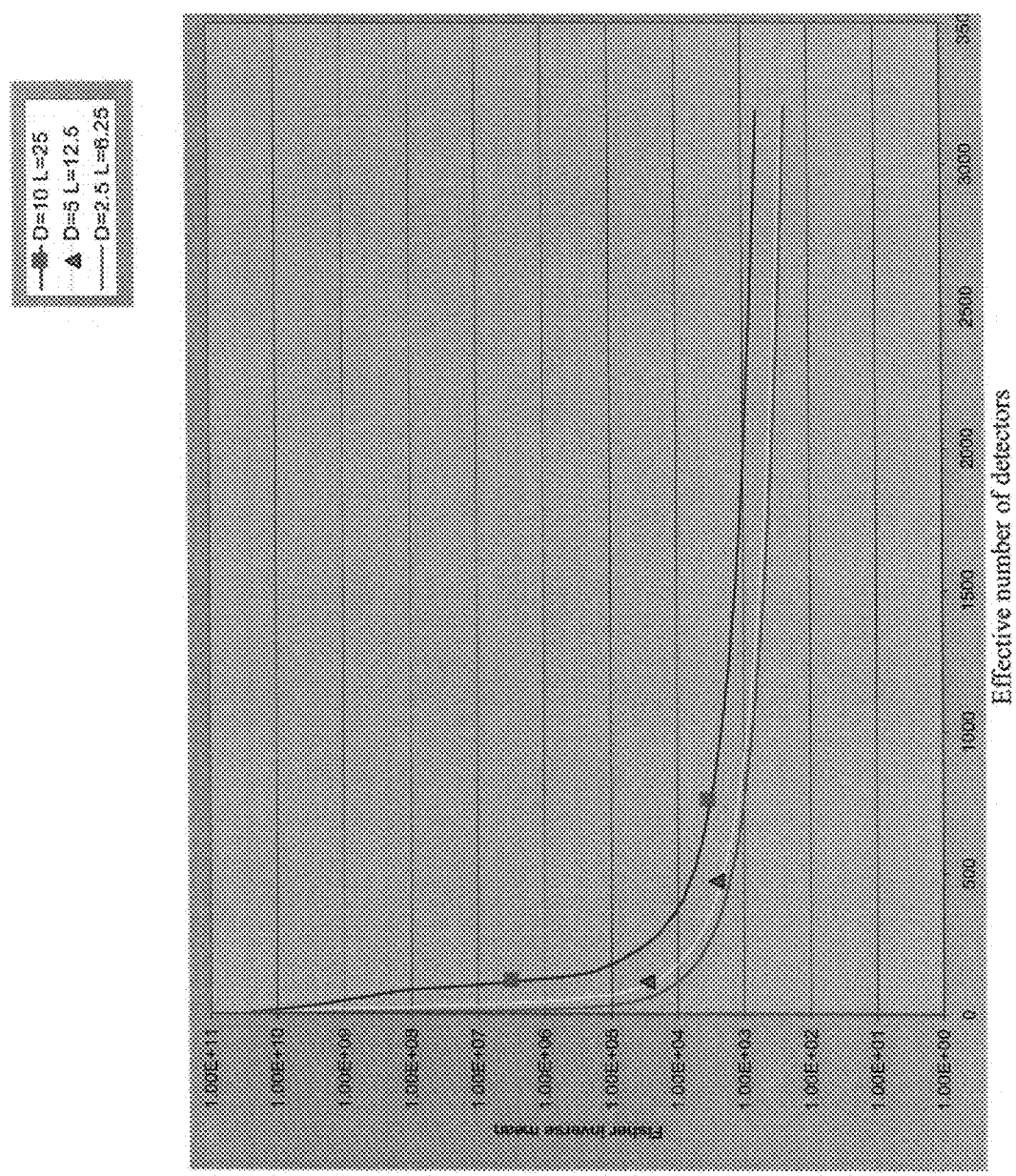

FIG. 33 illustrates view set selection results for the reliability criterion, based on minimizing the inverse mean of the Fisher information measure.

DESCRIPTION OF THE PREFERRED EMBODIMENTS

The present invention is of methods for identifying optimal, or preferred sets of views for radioactive-emission measurements of a region of interest within the body. The methods are based on models of the region of interest, and the preferred sets of views are identified for the models, preferably using information theoretic measures. The preferred sets of views may then be applied to the region of interest, in vivo. The principles and operation of the methods for optimizing radioactive-emission measurements, according to the present invention, may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1$j$ and 1$k$ present the principles of modeling, for obtaining an optimal set of views, in accordance with the present invention.

FIG. 1$j$ schematically illustrates a body section 120, having a region of interest (ROI) 130. The region of interest 130 may be associated with an organ 140, with a specific radioactive-emission-density distribution, possibly suggestive of a pathological feature 150, termed herein an organ target 150. Additionally, there may be certain physical viewing constraints, associated with the region of interest 130.

We thus consider the following problem: how can we best identify an optimal and permissible set of views for radioactive-emission measurements of the region of interest 130, for reconstructing a three-dimensional image of it?

In accordance with the present invention, our approach is delineated by the following process:
i. modeling the region of interest 130, as a model 160 of a volume U, possibly with one or several modeled organ targets HS, within anatomical constraints AC, as seen in FIG. 1$k$;
ii. obtaining an optimal and permissible set of views for the modeled volume U of FIG. 1$k$; and
iii. applying the optimal set of views to the in-vivo region of interest 130 and the organ 140 of FIG. 1$j$.

It will be appreciated that the model 160 of the region of interest 130 may be based on general medical information of the organ 140 and common pathological features associated with it. Additionally, the model may be based on information related to a specific patient, such as age, sex, weight, and body type. Furthermore, a structural image, such as by ultrasound or MRI, may be used for providing information about the size and location of the organ 140 in relation to the body section 120, for generating the model 160.

The present application concentrates on the second step of the process, namely, obtaining the optimal and permissible set of views for the volume U of the model 160.

Referring now to the drawings, FIGS. 1$l$ and 1$m$ pictorially illustrate a view and viewing parameters associated with it, in accordance with definitions of the present invention.

Seen in FIG. 1$l$ is a volume U, subdivided into voxels u. The volume U is defined in a six-degree coordinate system $(x;y;z;\omega;\theta;\sigma)$ and has a point of origin $P0(x0; y0; z0; \omega0; \theta0; \sigma1)$. A detecting unit 102 is positioned at a location and orientation $P1(x1; y1; z1; \omega1; \theta1; \sigma1)$. The detecting unit 102 has a detector 104 of a specific detector material of a thickness $\tau_d$, and a collimator 108 of a diameter D and a length L, so as to define a collection angle $\delta$. The location, orientation, and collection angle parameters determine a three-dimensional sector S, which is the portion of the volume U that is within the detector unit's field of view. The probability of detection of a given voxel outside of sector S is negligible, since a photon emitted from the given voxel outside of sector S will have a very low probability of reaching detector 104 through collimator 108.

FIG. 1$m$ schematically illustrates the emission rate of the volume U, as a function of time, given that a radioactive material of a specific half-life has been administered at a time T0.

A view may thus be defined as a group of nonzero probabilities of detecting a radioactive emission associated with all the voxels that form sector S (FIG. 1$l$).

A view is sometimes referred to as a projection, and the two terms are synonymous. Furthermore, a view defined over the sector S can be naturally extended to be defined over the group of all voxels in the volume U, by simply associating a zero probability with every voxel outside the sector S. This enables applying mathematical operations over the entire volume U.

The viewing parameters, which are the factors affecting the detection of radioactive emissions, are as follows:
i. Location and Orientation Parameters:
   a location and an orientation in a six-dimensional space, $P1(x1; y1; z1; \omega1; \theta1; \sigma1)$, with respect to the origin $P0(x0; y0; z0; \omega0; \theta0; \sigma0)$ of the volume U, in which the detecting unit 102 is positioned;
ii. Detector-unit Parameters:
   the detector unit geometry (e.g. length L, diameter D, and/or collection angle $\delta$), which together with the location and orientation parameters, $P1(x1; y1; z1; \omega1; \theta1; \sigma1)$ with respect to the origin $P0(x0; y0; z0; \omega0; \theta0; \sigma0)$ define the sector S;
   the septa thickness $\tau$, which affects the probability that a photon that enters the collimator will reach the detector as well as crosstalk effects (which occur when a photon which entered a neighboring cell penetrates the collimator and reaches the detector), hence, the detector efficiency
   the detector material, which affects the detector efficiency; and
   the detector thickness $\tau_d$, which affects the detector's stopping power, hence, its efficiency;

iii. Attenuation Parameters:
   attenuation properties of all the voxels within the sector S, as they affect the probabilities that radioactive emissions from a specific voxel within the sector S will reach the detector, wherein different voxels within the sector S may have different attenuation properties, since several types of tissue may be involved;
iv. Time Parameters:
   since the radiopharmaceutical decays with a specific half-life, the time ti since administration, and the duration of the measurement $\Delta t_1$, affect the number of emissions that occur during the radioactive-emission measurement.
v. Radiopharmaceutical Parameters:
   The half-life $t_{1/2}$, of the radiopharmaceutical, the types of radioactive emission, whether gamma or beta, and the energies of the radioactive emission affect the probability of detection.

Some of these viewing parameters are fixed for a particular situation. Specifically, the tissue attenuation parameters are given. Additionally, the time $t_1$ since administration of the radiopharmaceutical is generally governed by the blood pool radioactivity, since it is generally necessary to wait until the blood pool radioactivity dies out for low-level detection to be possible. For the remaining viewing parameters, optimization may be carried out.

To recapitulate the problem describe above, an intensity distribution I, in terms of radioactive emissions per seconds, is defined over the volume U, forming our input space. U comprises a set of basic elements u (e.g., pixels in two dimensional spaces, voxels in three dimensional spaces), and I(u) is the intensity in a given basic element $u \in U$. An inverse (or reconstruction) problem arises when one cannot sample directly from I, but can sample from a given set of views $\Phi$. A projection $\phi \in \Phi$ is defined by the set of probabilities $\{\phi(u): u \in U\}$, where $\phi(u)$ is the probability of detecting a radioactive emission from a voxel u, as defined by viewing parameters, such as the physical and geometrical properties of the detecting unit, as well as the attenuation parameters of the viewed volume U, and the time parameters. A measurement is obtained by choosing a view $\phi \in \Phi$, and then sampling according to the viewing parameters.

In the following analysis, I is the intensity of a radioactive substance, and the viewing parameters include the geometrical properties of a collimated detecting unit and the detecting unit's position and orientation with respect to volume U. The number of radioactive emissions counted by the detecting unit within a time interval is a Poisson distribution, where (p (u) is the detection probability of a photon emitted from voxel $u \in U$ and the mean of the distribution is the weighted sum $\Sigma_{u \in u} \phi(u)I(u)$.

The projection set is thus defined by a matrix $\Phi$, whose rows are the projections of the chosen views. I is a vector of densities (specified per each element in U), and $\Phi I$ is a vector of respective effective intensity levels for the views in the set. A vector of measurements y is obtained by a random sample from each view (according to the associated Poisson distribution). As discussed above, there are various known reconstruction methods that provide estimators for I given the projections $\Phi$ and the measurements y.

We consider here the following problem: Assume that there is a large pool of candidate views to choose from, but due to time restrictions or other restrictions, we are limited to a specific number of views N. Which are the best N projections in terms of the quality of the reconstruction? It is further assumed that the pool of projections may be constrained, and hence general sampling theorems (e.g., Radon Transform) cannot be applied. For instance, we consider a scenario in emission tomography where the detecting unit can be located on top of one face of a given volume but not on the others. In such cases, prior-art methods do not clearly establish what is the best scanning scheme, in order to provide the best reconstruction of the radioactive intensity distribution of the volume.

The following embodiments are of a method for selecting a set of optimal views of a volume to be imaged, and are not confined to a specific reconstruction algorithm. View selection is preferably based on information theoretic measures that quantify the quality of the data fed to the reconstruction algorithm.

Reference is now made to FIG. 2, which is a simplified flowchart of a method for selecting a set of optimal views of a volume to be imaged, according to a first preferred embodiment of the present invention. In step 200, a volume is provided, and is preferably represented as a collection of voxels. In step 210, a collection of views of the volume is provided. Each view reflects a possible data collection option, from which the goal is to select a set of views which together provide the desired image reconstruction quality. Each view is associated with one or more viewing parameters, such as the location and orientation of the detecting unit with respect to the volume.

The viewing parameters preferably further contain at least one of the following detecting unit characteristics: detector material, detector thickness, collimator length, diameter, septa thickness, and collection angle. When the viewing parameters include detecting unit characteristics, such as those discussed above, the view may be said to incorporate a model of a detecting unit.

In the preferred embodiment, the viewing parameters include a detection duration parameter, which corresponds to the duration of the measurement is performed (at the associated location, orientation, etc.). Increasing the detection duration generally improves the probability of the detection for those voxels in the detecting unit's collection angle.

Preferably, the viewing parameters include a type of radiopharmaceutical. The type of radiopharmaceutical determines the type of radioactivity being detected, and consequently the probability of detection.

Preferably, the viewing parameters include a time of detection, $t_D$, relative to an initial time $t_0$. As discussed above, in conjunction with FIG. 1m, during radionuclide imaging a radiopharmaceutical is administered to a patient, and after a suitable interval, to allow the radiopharmaceutical to disperse throughout the body, measurements are taken. Since the radiopharmaceutical decays at a specific rate after administration, depending on its half-life, the length of time between when the radiopharmaceutical is administered and the time of measurement affects the radioactive emission detection of the given view.

The view set is preferably tailored to correspond to the actual limitations and constraints likely to be encountered when collecting data for a given object. For example, in medical applications the detecting unit can generally view the body structure only from certain distances and orientations, which are determined by the patient's anatomy and the structure of the probe. The view set may therefore be designed to contain views having only those viewing parameter values consistent with attainable distances and orientations. The view set may also be designed to contain views having only those viewing parameter values suitable for a given measurement scenario, for example having identical values for the type of radiopharmaceutical and time since administration.

Preferably, the collection of views represents a quantized continuum of views. The view collection thus reflects the detection probability distribution for a detecting unit making periodic measurements while moving along a trajectory.

Reference is now made to FIG. 3, which shows a non-limiting example of a volume 300 with two views, $V_1$ and $V_2$. Volume 300 divided into twenty-seven cube-shaped voxels (labeled 1-27). Each view reflects a number of viewing parameters, in the case shown a location (in the XYZ coordinate system), orientation ($\omega$, $\theta$ and $\sigma$) and collection angle $\delta$. The viewing parameters determine which voxels in volume 300 are within a detecting unit's collection angle, and generally affect the probability of detection for each voxel. The probability of detection may be affected by additional factors, including the attenuation coefficients within the volume.

During data collection, the probability of detection for each voxel is dependent on the parameters outlined above. In the preferred embodiment, a respective projection is calculated for each view, giving the view's detection probability distribution (i.e. the detection probability for each voxel of the volume). For a given view, the associated projection will have significant detection probabilities only for those voxels within the sector defined by the detecting unit's collection angle and location and orientation, as illustrated in conjunction with FIG. 1*l*.

The detection probability distribution for each view, that is the group of probabilities for each voxel, for a given view, is calculated according to techniques known in the art for determining the detection probability of a radioactive emission from a given voxel, under the constraints specified by the viewing parameters, for example, based on computer simulations of the geometry and the other viewing parameters, delineated hereinabove.

Generally, more distant voxels will have a lower probability of detection than closer voxels along the same line of sight. The volume attenuation coefficient may be constant or may vary over the volume. Thus, different sets of views may be produced for a single sector, by defining volumes with differing attenuation coefficients. For example, bone tissue and muscle tissue have different attenuations. Anatomical knowledge of the body structure being imaged may be used to develop a model of the volume U with a non-uniform attenuation that reflects the expected attenuation of the given body structure.

Referring again to FIG. 2, in step 220 a scoring function is provided. The scoring function rates the information that is obtainable from the volume using any set of views (containing at least one view) taken from the collection of views. Several examples of scoring functions based on information-theoretic measures are discussed in detail below. Preferably, the scoring function is a function of the detection probability distribution, as given by the projections. Several preferred embodiments of the scoring function, are discussed in detail below.

In step 225, sets of views are formed from the collection of views. A score is then calculated for each of the sets.

In step 230, the scores calculated in step 225 are used to select one of the formed sets of views. A given scoring function may be used to select a set in a number of ways. In a first preferred embodiment, a required number of views is specified, and the highest scoring set with the specified number of views is selected. In a second preferred embodiment, the user may specify a minimal score which is known to provide satisfactory information quality, and select the smallest set which provides the specified score. However given a large collection of views the required number of calculations may be prohibitive. A third preferred embodiment used to reduce the computational burden is the greedy algorithm embodiment described for FIGS. 8-9 below.

Since each view is associated with known values of the viewing parameter(s), selecting a view effectively specifies known viewing parameter values. The selected set of views thus defines a set of viewing parameter values, which may be used to collect data which yields a high-quality reconstruction of the emission distribution of the volume.

As discussed above, the scoring function is a measure of the quality of information which may be gathered for the volume using the given set of views. In a first preferred embodiment, the scoring function implements a uniformity criterion, to ensure uniform coverage of the volume. It is often desired to obtain a uniform reconstruction quality among a given set of voxels $W \subset U$, where W is the set of voxels for which it is desired to obtain uniform detection. Note that by selecting the appropriate W, the uniformity criterion is applied to all or a portion of the body. The uniformity criterion ensures that the spread of the total influence of each element on the set of measurements is as uniform as possible. The uniformity criterion depends only on the collection of views $\Phi$ and requires no assumptions on the distribution I. For a set $\Phi$ of projections, the total influence of an element, u, is given by $\Sigma_{100 \in \Phi} \phi(u)$. Normalizing these values to $P_{101}(u)$, such that $$\sum_{u \in W} P_\Phi(u) = 1,$$

a probability measure is obtained for which the entropy $H(\Phi)$ can serve as a uniformity measure:

$$H(\Phi) = -\sum_{u \in W} P_\Phi \log P_\Phi(u) \quad (12)$$

The selected set $\Phi^*$ is the set (containing the required number of views) that satisfies:

$$\Phi^* = \arg max_{101} H(\Phi) \quad (13)$$

Reference is now made to FIG. 4, which illustrates the concept of uniform coverage of a volume. Volume 400 consists of twenty-seven cube-shaped voxels, including voxels 410 and 420. A, B, C and D are three views of volume 400, showing the detector position and orientation for each view. For the uniformity criterion, it is desired that the overall influence of voxels 410 and 420 be approximately equal.

Assume that the probabilities of detection are as follows:

| View | Voxel 410 | Voxel 420 |
| --- | --- | --- |
| A | 0.6 | 0 |
| B | 0.2 | 0.5 |
| C | 0 | 0.3 |
| D | 0 | 0.1 |

Consider two possible sets of views: set {A, B, C} and set {B, C, D}. For set {A, B, C}, the total contribution of voxel 410 is 0.8 (0.6+0.2+0) and of voxel 420 is 0.8 (0+0.5+0.3). Normalizing these values for set {A, B, C} gives a probability set of [0.5,0.5]. For set {B, C, D}, the total contribution of voxel 410 is 0.2 (0.2+0+0) and of voxel 420 is 0.9 (0.5+0.3+

0.1). Normalizing these values for set for set {B, C, D} gives a probability set of [0.18,0.82]. Thus:

$$H(\{A, B, C\}) = -(0.5*\log_2 0.5 + 0.5*\log_2 0.5) = -(-0.5-0.5) = 1$$

$$H(\{B, C, D\}) = -(0.18*\log_2 0.18 + 0.82*\log_2 0.82) = -(-0.44-0.07) = 0.51$$

Set {A, B, C} is thus seen to provide a more uniform coverage of volume 400 than set {B, C, D}.

In the above, the scoring function is defined independently of the emission intensity of the volume. However, scoring functions may be defined which calculate the score for a given set in relation to one or more emittance models. An emittance model is a representation of a specific radioactive-emission intensity distribution within the volume U, so as to model organ targets, such as hot regions, of a radioactive emission intensity, higher than the background level, regions of low-level radioactive emission intensity, which is nonetheless above the background level, and cold regions, of a radioactive emission intensity, lower than the background level. Given an object or class of objects, emittance models may be devised to reflect expected or typical emission patterns for the given object. The information quality given by a set of views may thus be measured in relation to expected emitted intensities from the volume.

Reference is now made to FIG. 5, which is a simplified flowchart of a method for selecting a set of optimal views of a volume to be imaged, according to a second preferred embodiment of the present invention. A volume is provided in step 500 and a collection of views is provided in step 510, essentially as described above. The current method differs from the method of FIG. 2 by the addition of step 515, in which a set of one or more emittance models is provided. An emittance model specifies the radiative intensity of each voxel in the volume. As discussed above, some of the viewing parameters affect the radiative intensity of the voxels in the volume, for example the type of radiopharmaceutical and the time since administration of the radiopharmaceutical. Therefore, the emittance models provided in step 515 preferably correspond to the relevant viewing parameters.

Once the emittance models are provided, a scoring function is provided in step 520. Sets of views are formed in step 525, and each of the formed sets is scored with the scoring function. In step 530, a set of views is selected from the collection of views based on the calculated scores.

Developing an emittance model for a particular object involves analyzing known information about the object to determine expected emission patterns of the object. In the preferred embodiment, the volume corresponds to a body structure. Preferably the body structure is one of: a prostate, a heart, a brain, a breast, a uterus, an ovary, a liver, a kidney, a stomach, a colon, a small intestine, an oral cavity, a throat, a gland, a lymph node, the skin, another body organ, a limb, a bone, another part of the body, and a whole body. In order to develop a model of a particular body structure, for example a prostate, many factors may be considered. Physical aspects, such as the size and shape of the prostate and the position of the prostate within the torso may be considered, as well as medical knowledge regarding typical emissions from healthy and diseased prostates. Additional information may concern variations between individuals, such as age, weight, percentage of body fat, and the like.

Reference is now made to FIG. 6, which shows four models of a prostate emittance model. Three views are given for each of the emittance models shown. Each of the views is a maximum intensity projection (MIP) along a different one of the three axes. For example, in an X-Y projection the intensity of a given point is taken as the maximum intensity for that point along a line parallel to the z-axis. Thus the volume in effect becomes "transparent", and the maximum intensity regions are shown clearly. Variations in emission levels are indicated by differences in shading. The emittance model is shaped as an ellipsoid, the typical shape of a prostate. Since a diseased prostate is generally characterized by one or more hot regions, each of the emittance models shown has a number of high-emittance portions (two hot regions in Models A-C and three hot regions in Model D). Each high-emittance area is an ellipsoid, with a size of approximately 1 cubic centimeter. The intensity of the modeled organ targets varies randomly from two to eight times brighter than the surrounding volume.

In the preferred embodiment, one or more of the emittance models contains at least one high-emittance portion (i.e. hot region). A prostate containing a tumor, for example, may be modeled as an ellipsoid volume with one or more high-emittance portions. A high-emittance portion is characterized by an intensity that is greater than the background intensity by a factor of at least $(1+\alpha)$, where $\alpha$ is a parameter specified by the user. In practice, a hotspot is usually detectable only if the radiation levels within the hotspot are higher than the background level by a factor of 1.5-2. $\alpha$ is therefore typically defined between 0.5-1. However, the detectability of a hotspot rises as the radioactive intensity of the body rises, raising the photon count. Thus, a lower value of $\alpha$ may be used when high-intensity emittance models are used.

In the preferred embodiment, one or more of the emittance models contains at least one low-emittance portion. A low-emittance portion is characterized by an intensity that is lower than the background intensity by a factor of at least $(1+\beta)$, where $\beta$ is a parameter specified by the user. In heart imaging, for example, the locations of interest are low-emittance portions of the structure, indicating non-functional tissues. A diseased heart may therefore be modeled as a heart-shaped volume with low-emittance portions.

Note that an emittance model need not contain high- or low-emittance portions, but may have a uniform intensity or a slowly varying intensity. Following are two more embodiments of scoring functions, both of which include considerations of the emission pattern of the volume, in light of the emittance models provided in step 515.

Following are a number of preferred embodiments of scoring functions which score view sets in relation to one or more emittance models.

In a second preferred embodiment, the scoring function implements a separability criterion. Separability is a measure of the extent to which the measurements that are obtained from each pair of models can be distinguished from one another.

Figure 7A:
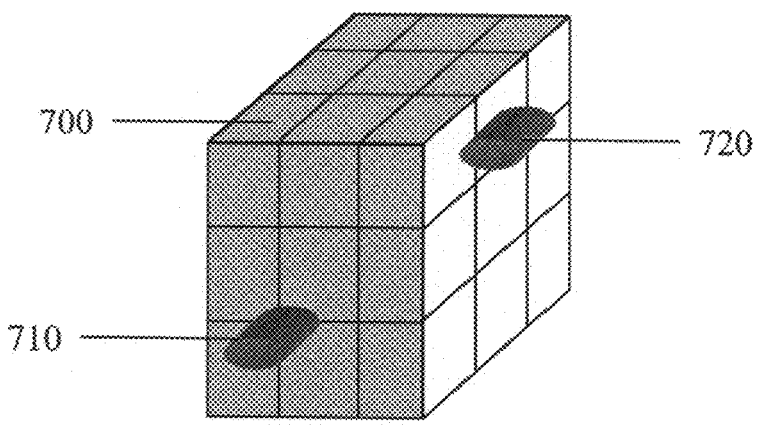
Figure 7B:
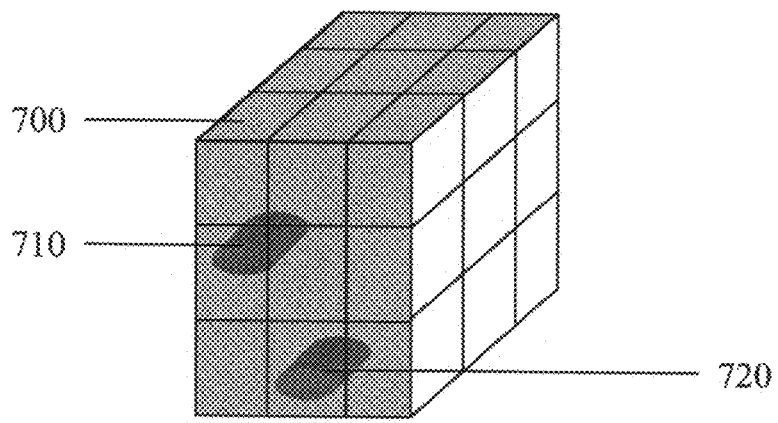
Figure 7C:
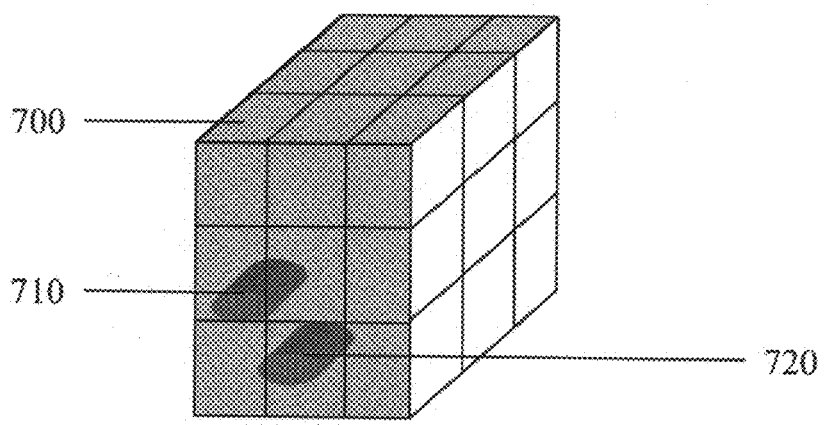

The concept of separability is illustrated in FIGS. 7a-7c, each of which shows an emittance model of a given volume 700. Each of the emittance models contains two high-emittance portions (hot regions), 710 and 720, which are located in respectively different locations in each of the models. It can be seen that the hot regions in emittance models 7b and 7c are in similar portions of the volume, as opposed to the hot regions in model 7a. It may therefore be difficult to distinguish between reconstructions of emittance models 7b and 7c. The separability criterion ensures that the selected set includes views which provide reconstructions which distinguish between emittance models 7b and 7c.

Letting I be the emittance model set, a measure for the dissimilarity of any two given densities in I is defined. Since most state-of-the-art estimating algorithm are aimed at finding ML estimators, in the current example the scoring function is based on the likelihood function. The likelihood of an estimator of I, given a set of Poissonian measurements y is:

$$\mathcal{L}(I) = \sum_t \left\{ -\sum_u \phi_t(u)I(u) + y_t \ln \sum_u \phi_t(u)I(u) - \ln(y_t!) \right\} \quad (14)$$

For separability, it is desired that this measure be different for each I∈I. Since the measure is a random variable that depends on the actual measurements, all possible pairings of emittance models should be examined to ensure that the resulting distributions are separable. A scoring function that captures this separability is given by the square of the difference between the means of the distributions normalized by the sum of their variances:

$$SEPARABILITY_\Phi(I_1, I_2) = \frac{|E\mathcal{L}(I_1) - E\mathcal{L}(I_2)|^2}{\text{Var}\mathcal{L}(I_1) + \text{Var}\mathcal{L}(I_2)} \quad (15)$$

The expectations and variances in Equation 15 are taken over random measurements y, sampled from the true intensity $I_1$ (note that the measure is not symmetric).

Since the true (unknown) intensity can be any I∈I, a projection set $\Phi^*$ that maximizes the worst-case separability is desired. That is:

$$\Phi^* = \arg\max_\Phi \min_{I_1, I_2 \in I} SEPARABILITY_{101}(I_1, I_2) \quad (16)$$

Scoring for separability is based on the minimum separability obtained with a given set of views for all of the possible pairings of emittance models from the set of emittance models, thereby enabling defining a desired resolution in more than one direction, or in more than one portion of the volume. All of the emittance models are modeled on a substantially identical volume. The emittance models preferably differ from one another in the modeled organ targets, where the modeled organ targets are separated by a difference of at least the required resolution (where the displacement which produces the required resolution is denoted delta herein). Substantially identical sets of views are formed from the collection of views, and each of the formed sets is scored with respect to each of the pairs. One of the sets of views is selected, based on the minimum or average score for the plurality of pairs.

For example, assume the set of emittance models contains the three models 7a-7c. A separability score is calculated for a given formed set of views by applying Equation 15 to all three pairs 7a/7b, 7a/7c, and 7b/7c. The lowest of the three calculated values is taken as the separability score for the formed set. Once a separability score has been calculated in such manner for each of the formed sets of views, the view set having the highest separability is selected.

The separability criterion may be used to ensure that a required resolution is obtained in all or a portion of the body. In a preferred embodiment, view set selection for separability is performed utilizing a set of emittance models consisting of one pair of emittance models having substantially identical volumes but with different modeled organ targets. The modeled organ targets are separated by a delta in a given direction so as to define a required resolution in that direction and portion of the volume U. Substantially identical sets of views are formed from the collection of views, and scored with respect to the pair of emittance models, using a scoring function based on the separability criterion, and one of the sets of views is selected based on the separability scores. The selected set is thus the set which provides the optimum resolution in the given direction and in the vicinity of the modeled organ targets.

A similar approach may be used to ensure resolution in more than one direction and/or portion of the volume U. Consider for example, a pair of models of substantially identical volumes, as follows: The model of FIG. 7d, which schematically illustrates the volume U, having the modeled organ target HS, whose center is at a location $(x;y;z)_{HS}$, and the model of FIG. 7e, which schematically illustrates the volume U, having the modeled organ target HS', whose center is at a location $(x;y;z)_{HS'}$. FIG. 7e also shows modeled organ target HS of FIG. 7d superimposed over the present emittance model to illustrate that HS' is somewhat displaced from HS, along the x-axis, and the displacement, is denoted as delta1 in the present example. The displacement delta may be measured, for example, in mm.

Figure 7D:
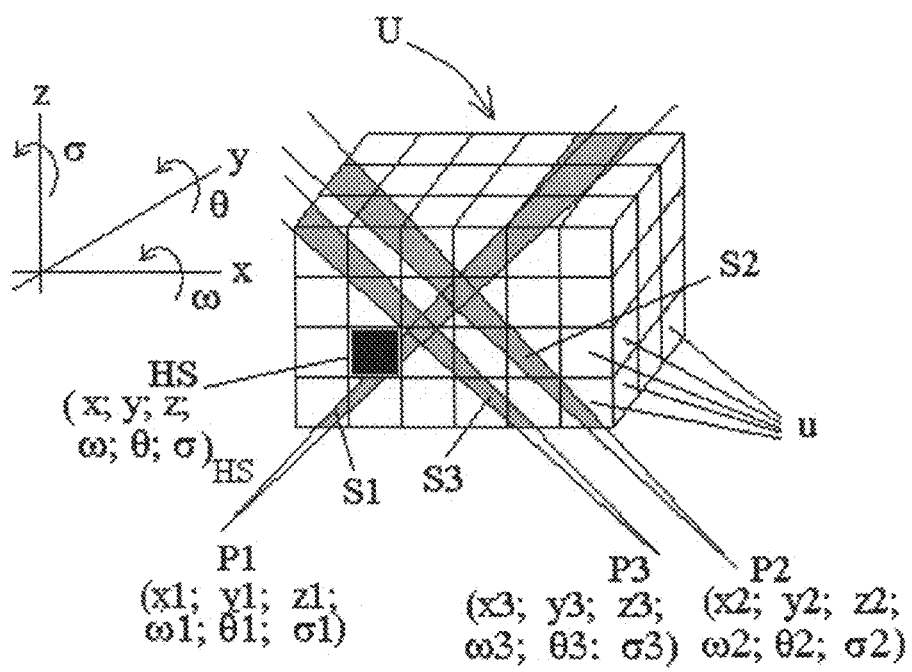
Figure 7E:
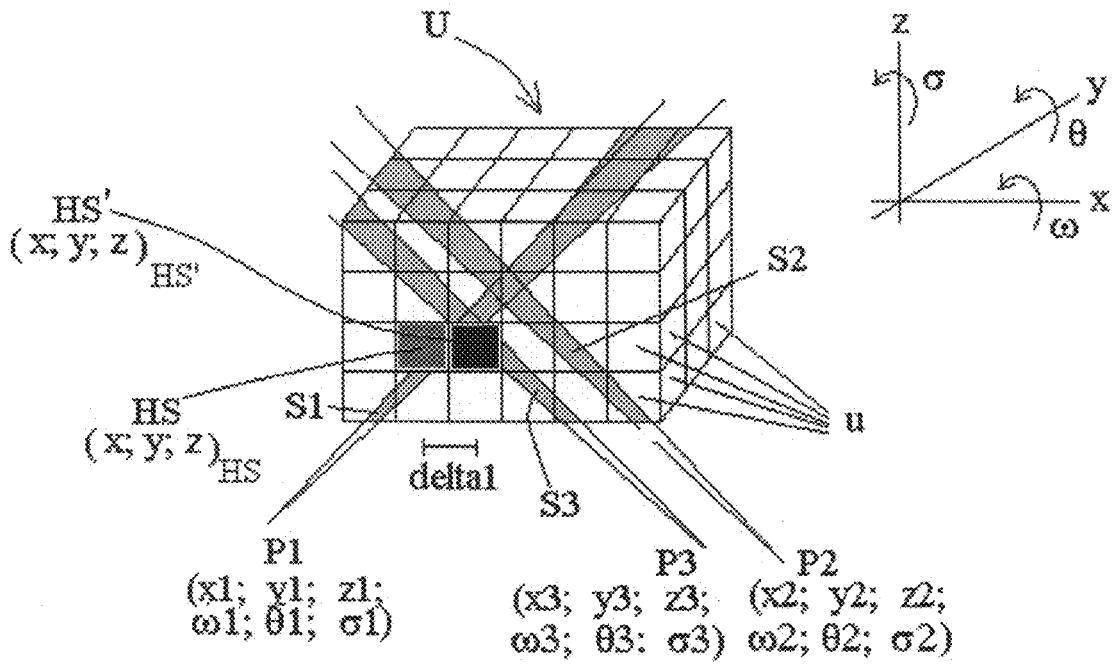

An optimal set of views, from the standpoint of separability, is that which will best distinguish between the model of FIG. 7d and that of FIG. 7e. Thus, a score, in terms of separability is given for the pair of models, and relates to a resolution as defined by the difference between the models of the pair. In the present example, the difference is delta1 along the x-axis, around the locations of HS and HS', so the score given by the information theoretic measure of separability will relate specifically to a resolution as defined by delta1 along the x-axis, around the locations of HS and HS'. Other portions of the volume U and other directions may have different resolutions.

Figure 7F:
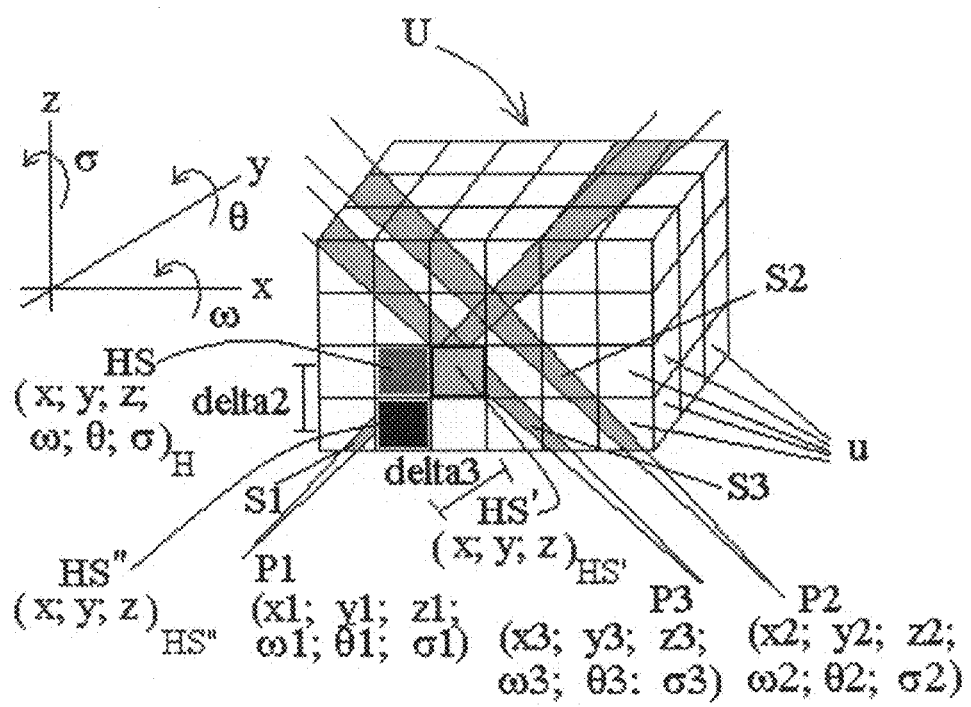

For example, consider the model of FIG. 7f, which schematically illustrates the volume U, having the modeled organ target HS", whose center is at a location $(x;y;z)_{HS''}$, and shows HS of FIG. 7d and HS' of FIG. 7e superimposed over the present emittance model. HS" is displaced from HS, along the z-axis, a displacement delta2. and additionally, HS" is displaced from HS', along the x- and z- axes, a displacement delta3.

Scores, in terms of separability, may be given to all the paring combinations, that is the models of FIGS. 7d-7e, relating to delta1; the models of FIGS. 7d-7f, relating to delta2, and the models of FIGS. 7e-7f, relating to delta3. An optimal set of views may be selected based on its minimum or average scores for all the pairing combinations; for example, the optimal set may be that whose average score for all the pairing combinations is the highest. Alternatively, a weighted average may be applied.

In an additional preferred embodiment, the scoring function implements a reliability criterion, which is a measure of how reliably the intensity distribution of a given object may be reconstructed from the sampled views. Since the input to the reconstructed algorithm is a random sample, the output estimator is also random. A desired property of this output is that it be reliable in the sense that similar estimators for different projected samples (i.e. different sets of measurements) of the same input intensity are obtained with high confidence.

The Fisher Information, $F_\Phi(I)$ is a measure, known in the art, which is used to evaluate the expected curvature of the likelihood of a model I (taken over measurements sampled from the model I). The Fisher Information is defined as:

$$F_{101}(I) = -E\nabla^2 L(I) \quad (17)$$

The derivatives are taken with respect to the parameters of the intensity I, and the expectation is taken with respect to the random counts. Intuitively, a sharper curvature means that a maximum-likelihood estimation algorithm is more likely to produce a low-variance estimator. Indeed, this property is captured by the Cramer-Rao lower bound, which states that the inverse of the Fisher Information is a lower bound for the variance of any unbiased estimator, where an estimator f of the intensity I is unbiased if Ef(y)=I.

The Fisher information provides a value, $F_\Phi(I)_{u,v}$, for each pair of voxels u and v. To provide a single measure for the reliability of the estimator, the average level, worst case, or other reasonable measure may be taken over the voxels. In the current example, the scoring function is based on the average Fisher information. Starting with a set of emittance models to be used by the estimating algorithm to provide a reliable estimator, the average of the above measure is maximized over the entire set, defining the selected set Φ* as:

$$\Phi^* = \operatorname{argmax}_\phi \sum_{I \in I} \sum_{u \in U} [F_\Phi(I)]_{u,u} \quad (18)$$

Alternately, a set may be chosen to minimize the inverse of the Fisher information, by selecting for:

$$\Phi^* = \operatorname{argmin}_\phi \sum_{I \in I} \sum_{u \in U} [F_\Phi(I)^{-1}]_{u,u} \quad (19)$$

Since inverting $F_\Phi(I)$ may be computationally expensive, the $[F_\Phi(I)^{-1}]_{u,u}$ term in Equation 19 may be replaced with $1/[F_\Phi(I)]_{u,u}$ (thus neglecting the off-diagonal elements of the Fisher Information matrix $F_\Phi(I)$). Note that Equations 18 and 19 are not mathematically equivalent, and may therefore yield different selected sets.

In the preferred embodiment, scoring is performed using the reliability criterion, and two or more emittance models are provided, having substantially identical volumes, but different modeled organ targets. Substantially identical sets of views are formed for all the emittance models, and each set is scored for reliability. One of the sets of views is then selected based on the average score for all the of the emittance models.

Figure 7G:
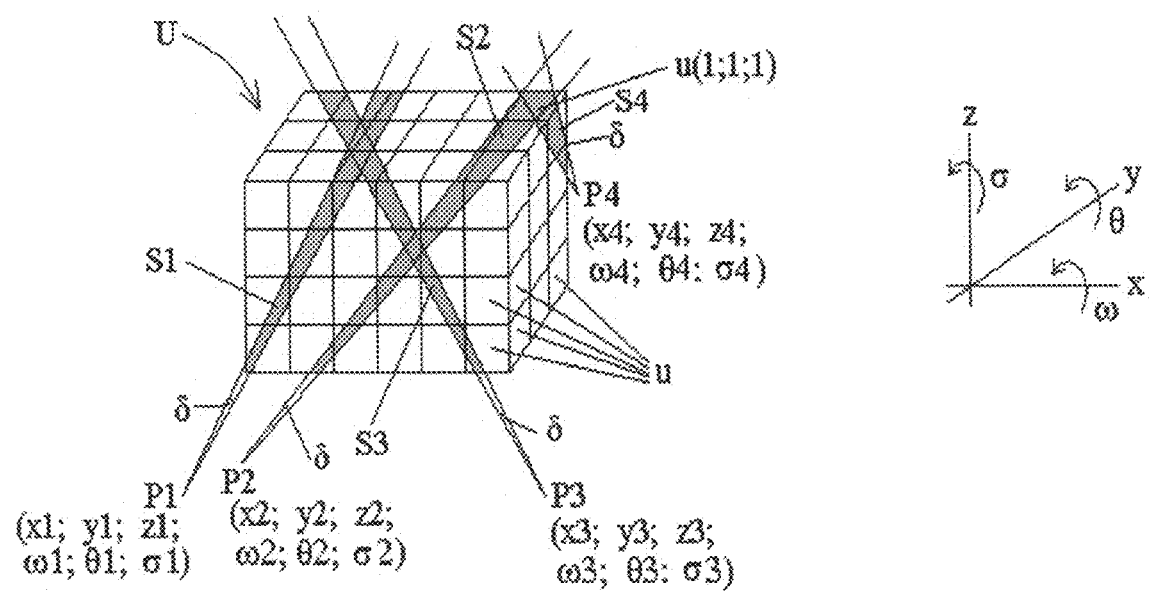
Figure 7H:
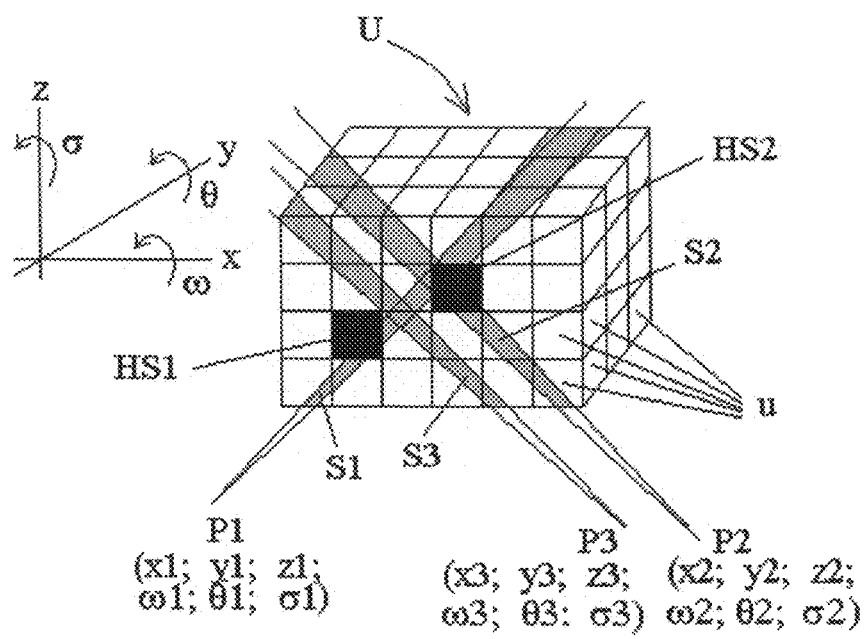
Figure 7I:
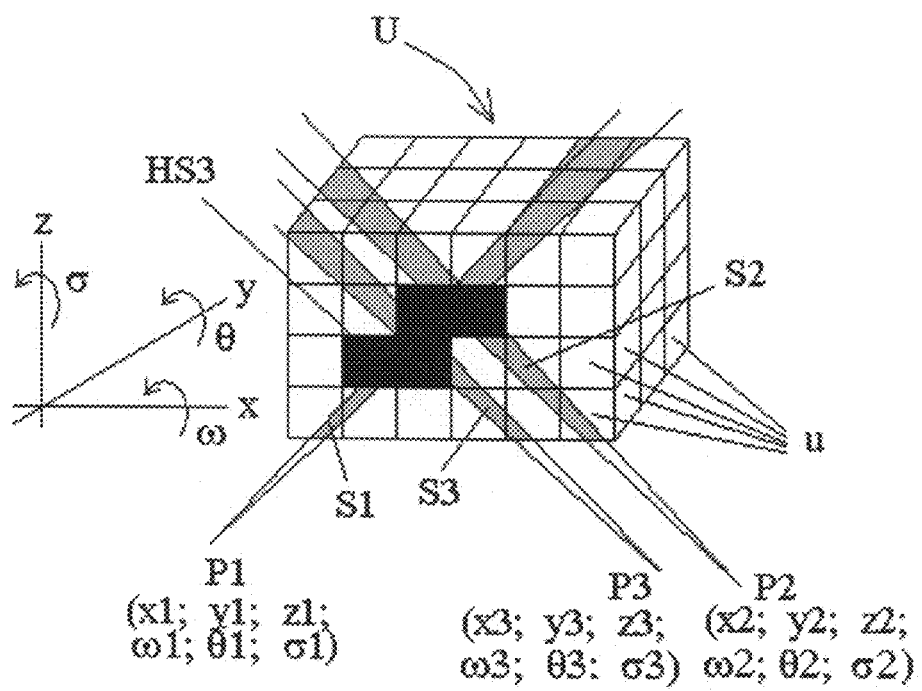
Figure 7J:
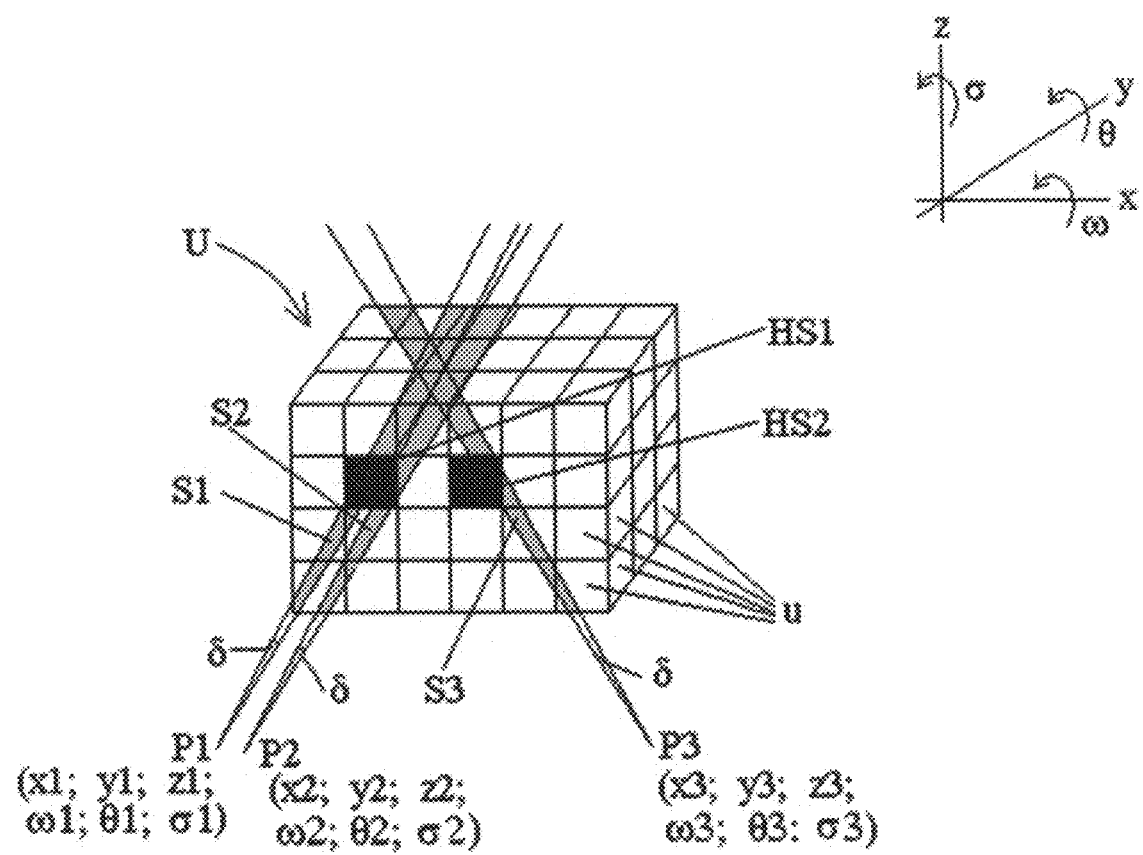

In a fourth preferred embodiment, a weighted combination of several information theoretic measures is used. For example, a plurality of models may be provided, all having substantially identical dimensions and volumes, as follows:

i. a first model, free of radioactive emission sources, as seen in FIG. 7g, for scoring sets of views in terms of uniformity;

ii. a pair of models with slightly different distributions of radioactive emission sources, as seen in FIGS. 7h and 7i, for scoring sets of views in terms of separability;

iii. a model with a given distribution of radioactive emission sources, as seen in any one of FIGS. 7h, 7i or 7j, for scoring sets of views in terms of reliability.

Identical sets of views may be applied to all the models, and each view may be scored in terms of uniformity, separability, and reliability. An optimal set of views may be selected based on a summation of the three scores, or based on a weighted average of the three scores, where the relative weight given to each criterion reflects the relative importance of each measure per the given application.

The scoring function is preferably defined in accordance with one of the following: worst case effectiveness for the given view over the volume, average effectiveness for the given view over the volume, worst case effectiveness for the given view over the set of emittance models and average effectiveness for the given view over the set of emittance models.

As discussed above, selecting the best set of size N from amongst a large set of candidate projections is computationally complex. Since the size of the collection of views and of the required set may be large, a brute force scheme might not be computationally feasible.

In an additional preferred embodiment, a so-called "greedy algorithm" is used to incrementally construct larger and larger sets, until a set containing the required number of views is obtained. The algorithm starts with an initial set, and in each iteration adds the view that yields the maximum improvement of the set score (hence the name "greedy").

In theoretical terms, assume p(*) is the quality measure we are using for the view selection, and assume without loss of generality that we are trying to maximize this measure. We gradually build a set W of projections as follows. We start with an empty set W=Ø, and at every stage choose the projection that maximizes the quality measure when added to the current set:

$$W \leftarrow \arg\,max_{W'}\{\rho(W')|W'=W\cup\{\phi\},\phi\in\Phi\} \quad (21)$$

In other words, during a given iteration, a respective score is calculated for a combination of the previous set with each of the views which is not a member of the current set. The current set is then expanded by adding the view which yielded the highest respective score, and the expanded current set serves as the input to the following iteration. Thus the number of times the scoring function is calculated per iteration drops from iteration to iteration. For a large initial collection of views, the greedy algorithm reduces the total number of computations required for set selection.

Reference is now made to FIG. 8, which is a simplified flowchart of an iterative "greedy" method for selecting a set of views, according to a preferred embodiment of the present invention. In step 800 an initial set of views is established from the collection of views. In the preferred embodiment, the initial set is an empty set. In step 810 the view set is incrementally increased by a single view during each iteration, until a set containing the required number of views has been selected.

Reference is now made to FIG. 9, which is a simplified flowchart of a single iteration of the view selection method of FIG. 8, according to a preferred embodiment of the present invention. The method of FIG. 9 expands the current set of views by a single view. The method begins with a current set of views, which is the initial set (step 800 above) for the first iteration, or the set formed at the end of the previous iteration (step 920 below) for all subsequent iterations. In step 900, a respective expanded set is formed for each view not yet in the current set of views. A given view's expanded set contains all the views of the current set as well as the given view. In step 910, a respective score is calculated for each of the expanded sets using the scoring function. Finally, in step 920, the current set is equated to the highest-scoring expanded set by adding the appropriate view to the current set. The newly formed current set serves as an input to the subsequent iteration, until the desired number of views is attained.

Following is a further preferred embodiment of a view selection method, in which multiple view sets are first formed from one or more scoring functions, and then a final selection is made of one of the resulting sets.

Reference is now made to FIG. 10, which is a simplified flowchart of a method for selecting a set of optimal views of a volume to be imaged, according to a third preferred embodiment of the present invention. In step 1000, a volume to be imaged is provided. The volume preferably corresponds to a body structure. In step 1010, a collection of views for performing radiation detection of a volume is provided. Each of the views is associated with at least one viewing parameter. Preferably the viewing parameters consist of at least one the following: detector location, detector orientation, viewing angle, material, thickness, collimator length, septa thickness, cell size, detection duration, time of detection, and a type of radiopharmaceutical.

In step 1020 at least one scoring function is provided. Each scoring functions is for scoring sets of views, essentially as described above. As discussed above, a single scoring function may be used to select several sets of views, where each set of views contains a different number of views.

In step 1030, multiple sets of views are formed from the collection of views, using the scoring function(s) provided in step 1020. In a first preferred embodiment, each of the sets is formed using a different one of the scoring functions. In an alternate preferred embodiment, one or more of the scoring functions are used to form more than one set of views, where sets formed with the same scoring function have differing numbers of views.

In step 1040, a selected set of views is obtained from the sets formed in step 1030. Knowledge about the conditions under which a particular set of measurements will be taken may be used to determine the optimal final set of views for a given data collection scenario.

In a first preferred embodiment, the final set of views is obtained by choosing one of the sets formed in step 1030 using a set selection criterion. For example, a respective set is formed in step 1030 for each of the uniformity, separability, and reliability criteria independently. A set selection criterion which calculates an overall performance rating for a given set taking all three criteria into account is defined, and the formed set with the highest overall rating is selected as the final set.

In another preferred embodiment, the selected set of views is obtained by merging the sets formed in step 1030 according to the relative importance of the respective scoring function used to form each set.

In the preferred embodiment, the method further consists of providing at least one emittance model representing the radioactive-emission density distribution of the volume, and scoring with at least one of the scoring functions of step 1020 is performed in relation to the emittance models. Preferably the emittance model(s) represent a body structure.

As discussed above, since each view is associated with one or more parameters, the selected set yields a group of optimal parameter values for performing effective detection of the intensity distribution of a volume. For example, if each view is associated with a view location parameter the selected set defines a set of locations for collecting emission data from an object, in order to provide a high-quality reconstruction of the intensity distribution of the object.

Reference is now made to FIG. 11, which is a simplified block diagram of a set selector for selecting a set of optimal views of a volume to be imaged, according to a first preferred embodiment of the present invention. Set selector 1100 consists of volume provider 1110, view provider 1120, scoring function provider 1130, and set selector 1140. Volume provider 1110 provides the volume to be imaged. View provider 1120 provides a collection of views of the volume to be imaged, where each of the views is associated with at least one viewing parameter. Scoring function provider 1130 provides a scoring function, which can score any set of view(s) from the collection with a score that rates information obtained from the volume by the set. Set selector 1140 utilizes the volume, views, and scoring functions to select a set from the collection.

Preferably, set selector 1100 further contains projection calculator 1150 which calculates a detection probability distribution for each of the views, in accordance with the respective viewing parameters and a volume attenuation coefficient.

Reference is now made to FIG. 12, which is a simplified block diagram of a set selector for selecting a set of optimal views of a volume to be imaged, according to a second preferred embodiment of the present invention. Set selector 1200 consists of volume provider 1210, view provider 1220, scoring functions provider 1230, sets former 1240, and set chooser 1260. Volume provider 1210 provides the volume to be imaged. View provider 1220 provides a collection of views of the volume to be imaged, where each of the views is associated with at least one viewing parameter. Scoring functions provider 1230 provides one or more scoring functions. Each of the scoring functions can be used to calculate a score for any set of view(s) from the collection. The calculated score rates the information obtained from the volume by the given set. Sets former 1240 uses the various scoring functions to form multiple sets of views from the collection of view, as discussed above for FIG. 10. Set obtainer 1260 obtains a final set of views from the sets of views formed by sets former 1240.

Preferably, set selector 1200 further contains projection calculator 1250 which calculates a detection probability distribution for each of the views, in accordance with the respective viewing parameters and a volume attenuation coefficient.

The above described set selection methods may each be embodied as a computer program stored on a computer-readable storage medium. In a first preferred embodiment, the computer-readable storage medium contains a set of instructions for selecting a set of optimal views of a volume to be imaged, consisting of the following routines. A volume provision routine provides the volume to be imaged. A view provision routine provides a collection of views of the volume to be imaged, each of the views being associated with at least one viewing parameter. A scoring function provision routine provides a scoring function, by which any set of at least one view from the collection is scorable with a score that rates information obtained from the volume by the set. The set formation routine forms sets of views from the collection of views, and scores them using the scoring function. The set selection routine selects a set of views from the collection of views, based on the scoring function.

In a second preferred embodiment, the computer-readable storage medium contains a set of instructions for selecting a set of optimal views of a volume to be imaged, consisting of the following routines. A volume provision routine provides the volume to be imaged. A view provision routine provides a collection of views of the volume to be imaged, each of the views being associated with at least one viewing parameter. A scoring functions provision routine provides at least one scoring function. Each of the scoring functions is usable to calculate a score for any set of at least one view taken from the collection of views. The score rates information obtained from the volume by the set of views. A sets formation routine selects multiple sets of the views using the scoring function(s), and a set obtaining routine obtains a final set of views from the sets formed by the sets formation routine.

It is expected that during the life of this patent many relevant detection probes, detector types, radiation-based detection systems and algorithms will be developed and the scope of the corresponding terms are intended to include all such new technologies a priori.

As used herein the term "about" refers to±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

FIGS. 13-18 illustrate view set selection results for the uniformity criterion. The selected views are chosen from a collection of views using an entropy-based scoring function. The specified viewing parameters are the detector location and the detector type (having a given detector size, D, and collimator length, L). Each view is defined for one of three detector types, large (D=10, L=25), medium (D=5, L=12.5) or small (D=2.5, L=6.25).

Figure 13:
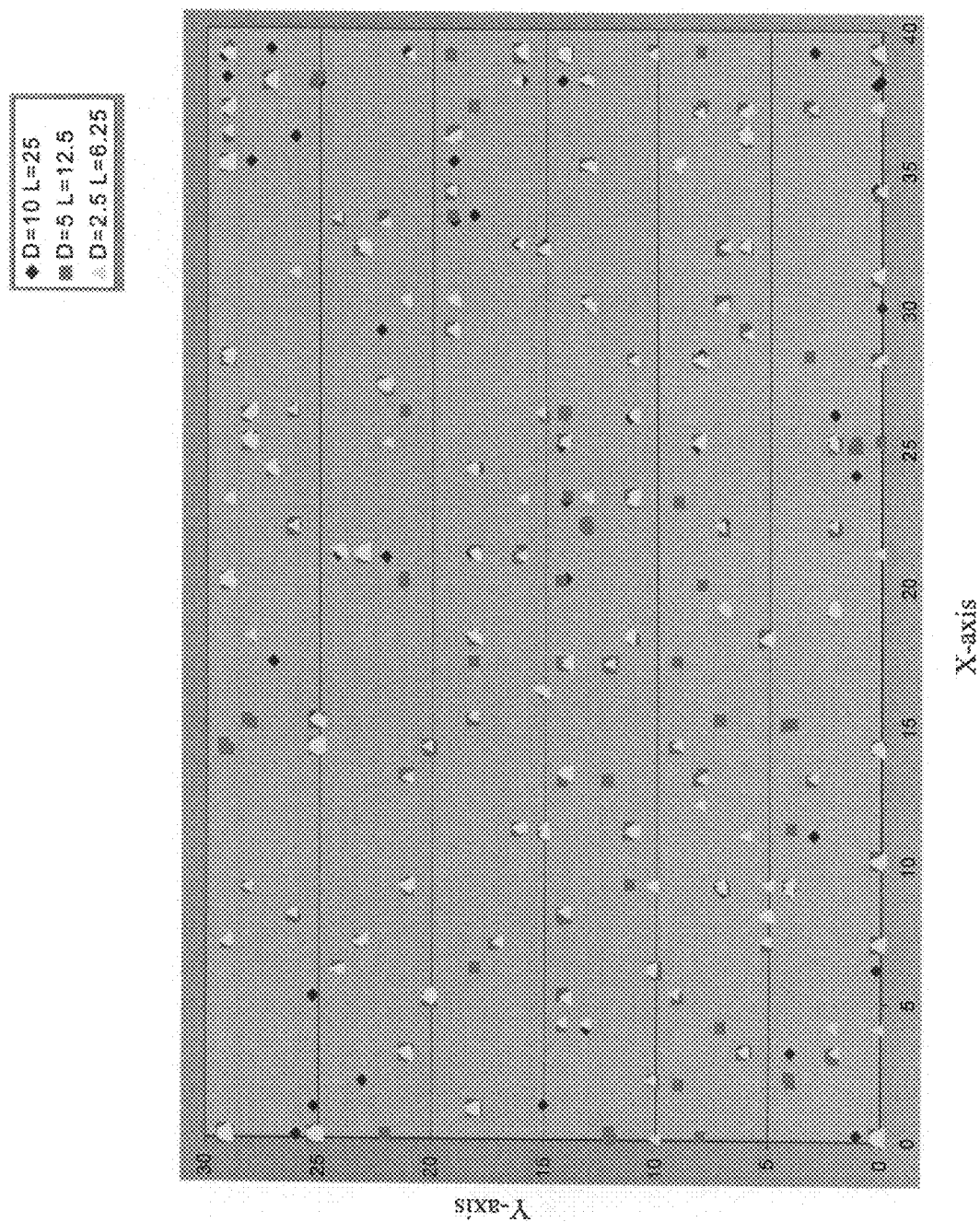

FIG. 13 shows a selected set of 500 views. The location of each view in the XY surface is shown, along with the associated detector type. As expected, the selected views are distributed relatively evenly over the XY surface and over the three detector types shown.

Figure 14A:
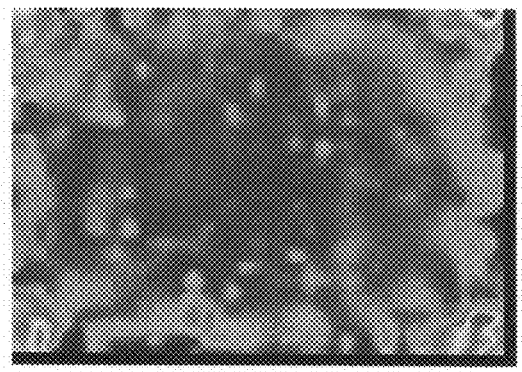
Figure 14B:
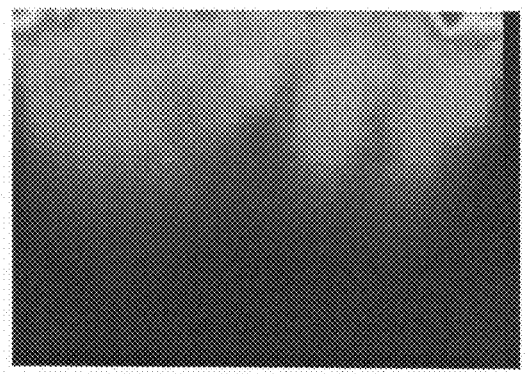
Figure 14C:
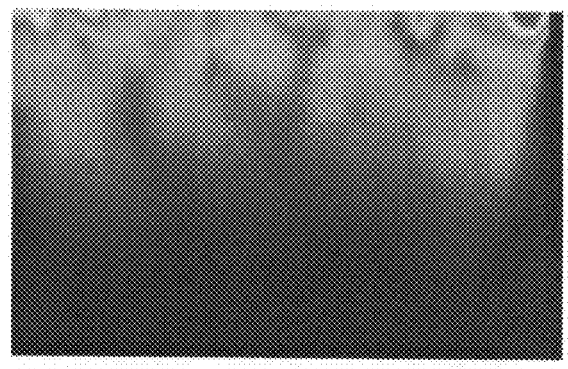

FIGS. 14a-14c show the resulting coverage provided by the selected views, from the top, side, and front aspects of the volume respectively. Even coverage is indicated by an even hue in the figure. Uniform coverage is well obtained for the side and front aspects, but is less successfully obtained for the top aspect.

Figure 15:
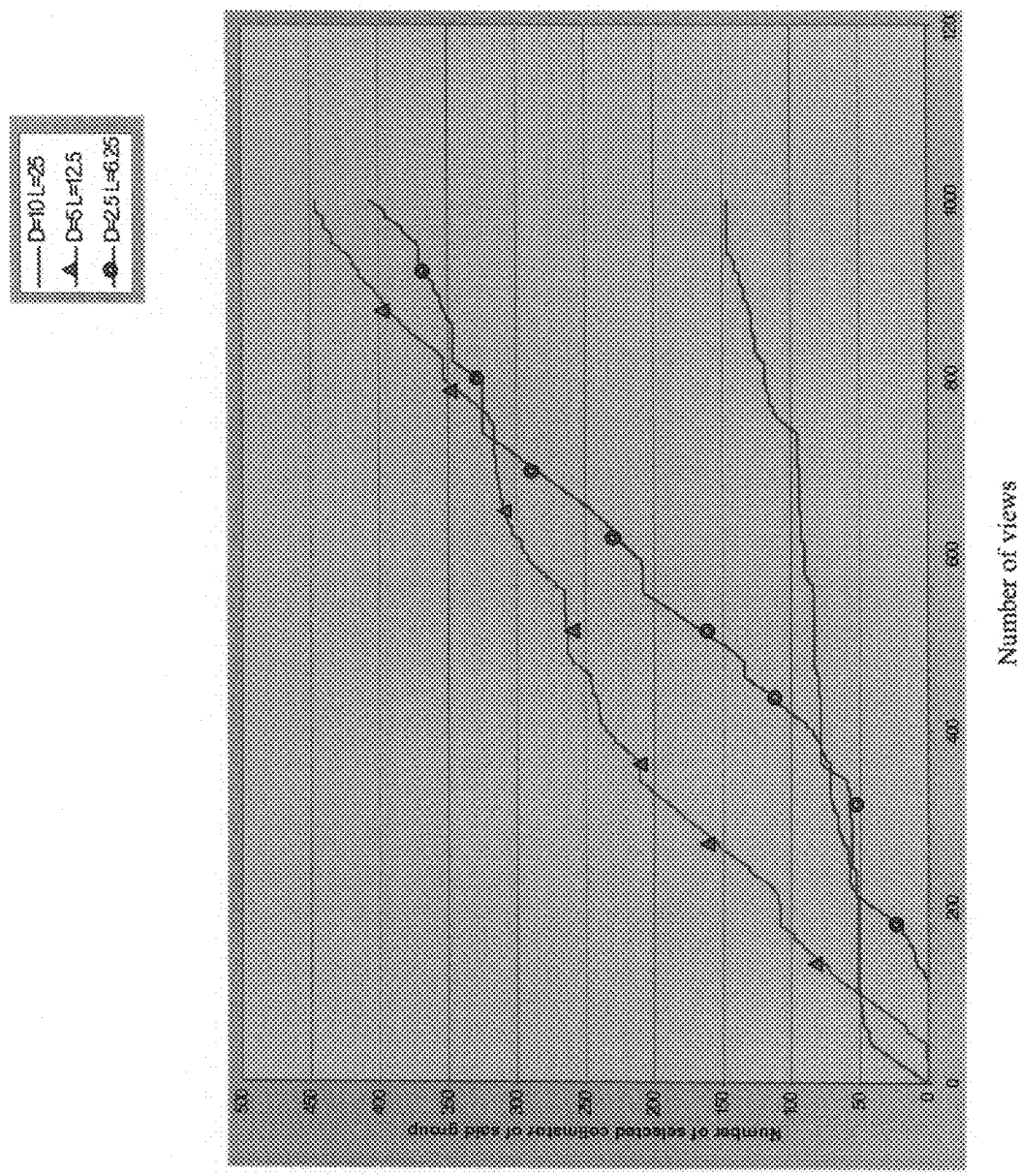

FIG. 15 illustrates the distribution of the detector types as a function of the number of views in the set. The large detectors, with their high sensitivity but low resolution, predominate only for small selected sets. As the size of the selected set increases the number of small detectors increases, improving the coverage of the collected data.

Figure 16:
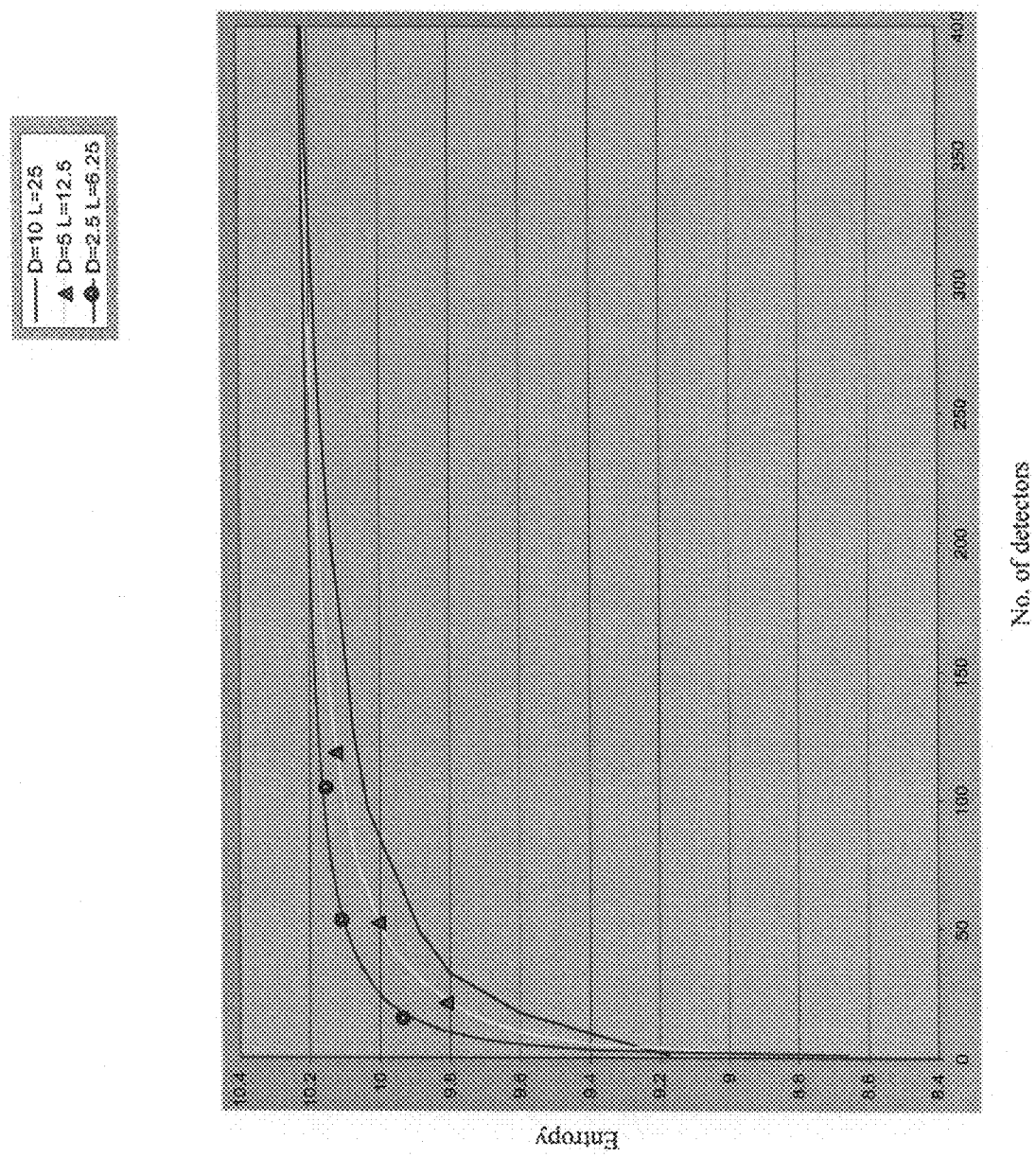
Figure 17:
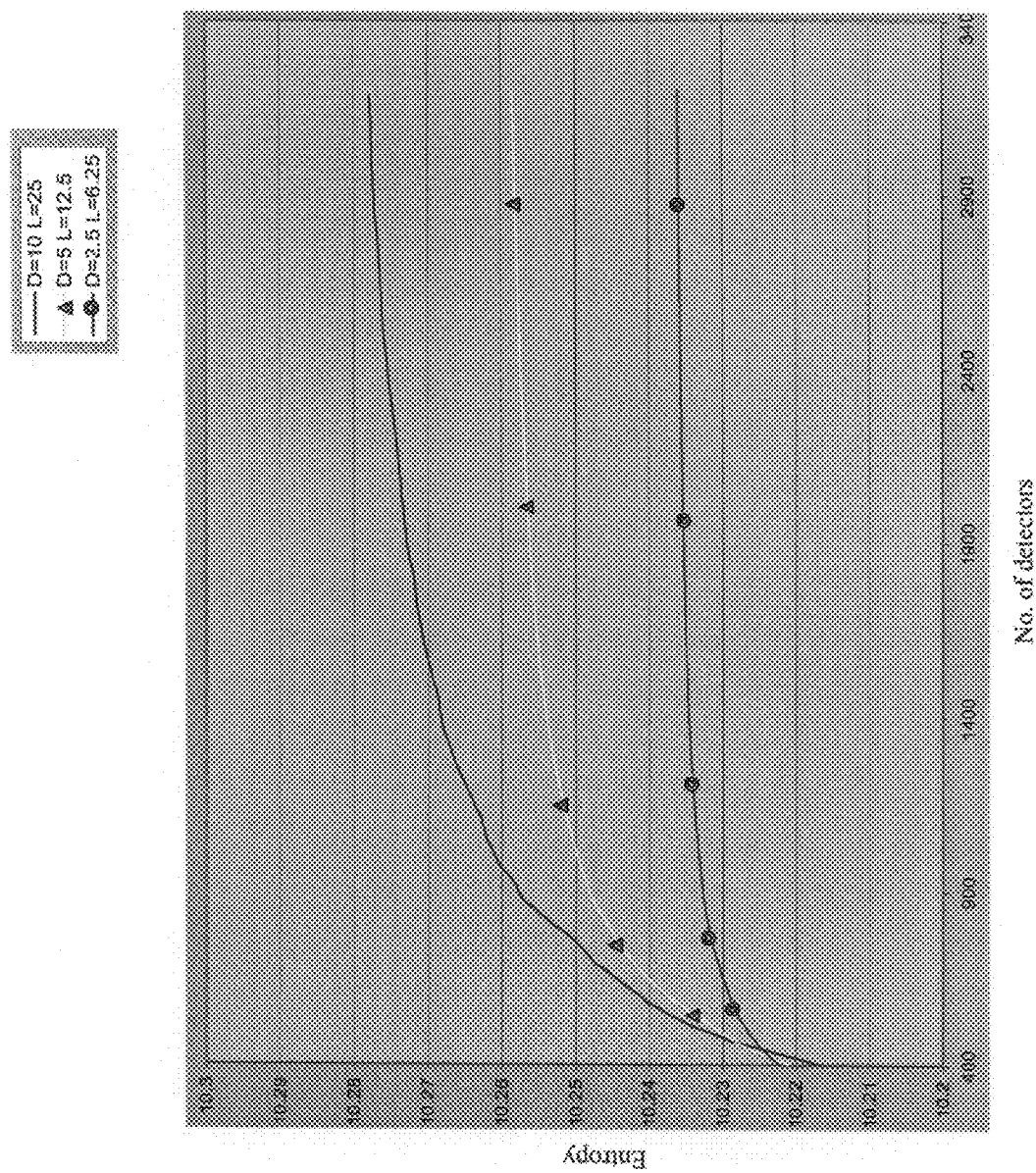
Figure 18:
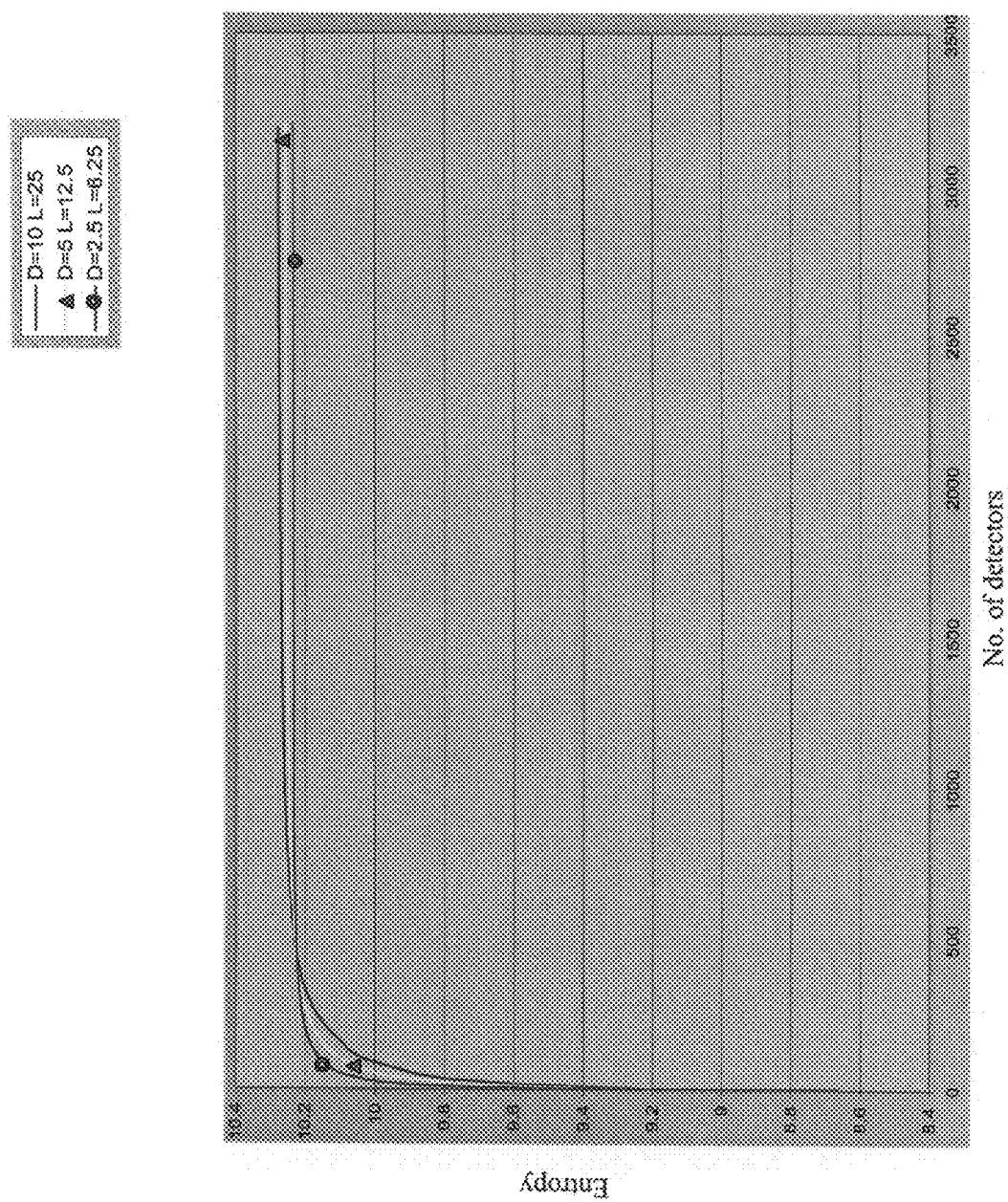

FIGS. 16-18 show the value of the entropy measure, used for the uniformity criterion, for each of the detector types, as the number of views increases. For sets including up to 400 views, the large detector gives the highest entropy level (i.e. enables the most uniform coverage). However, for selected sets containing more than 400 views the highest entropy value is obtained with the small detector. This is in accordance with FIG. 15, which shows an increasing proportion of small detector views as the size of the selected set increases.

FIGS. 19-24 illustrate view set selection results for the separability criterion. The viewing parameters include detector location, detector orientation, and one of three detector types, large (D=10, L=25), medium (D=5, L=12.5) or small (D=2.5, L=6.25).

Figure 19:
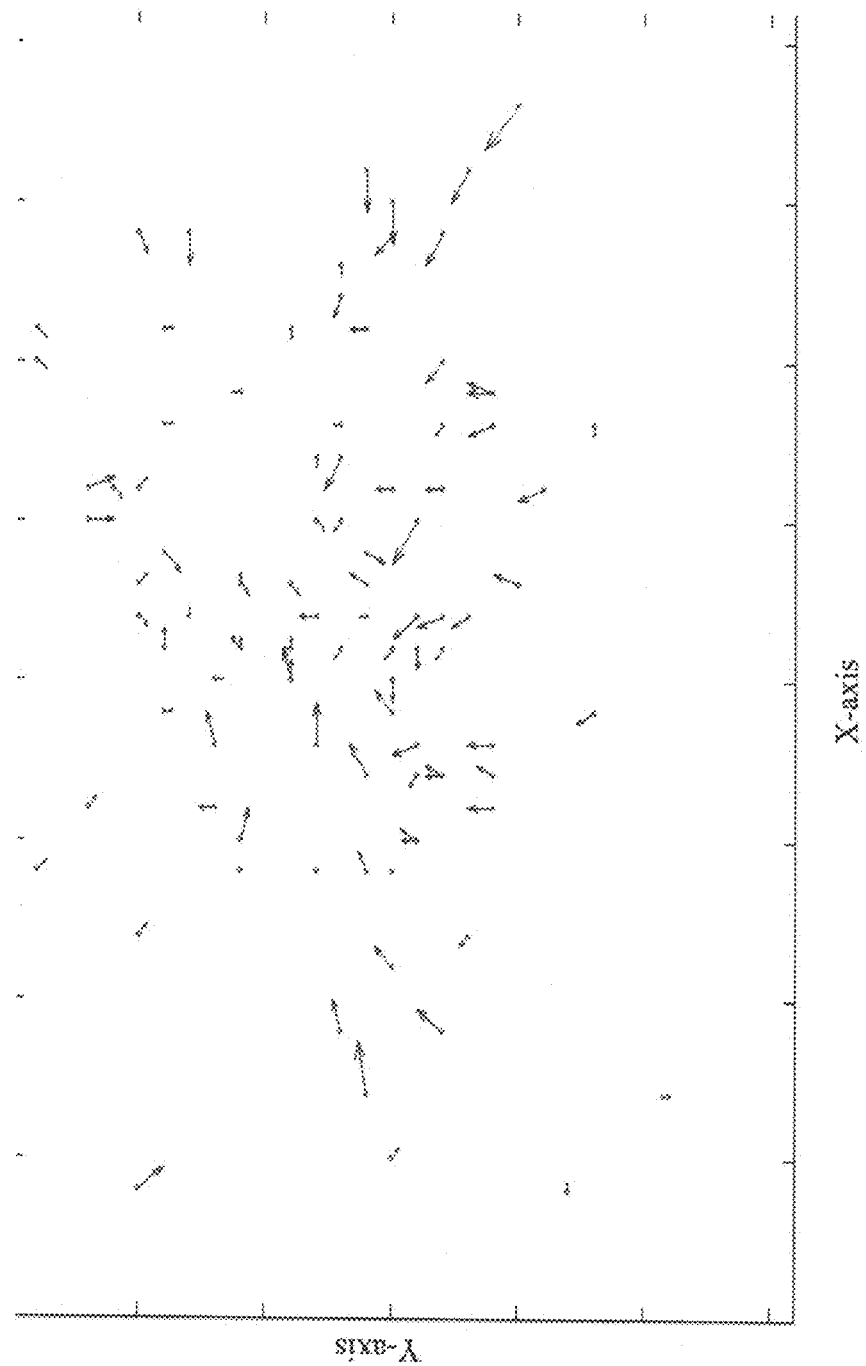
Figure 20:
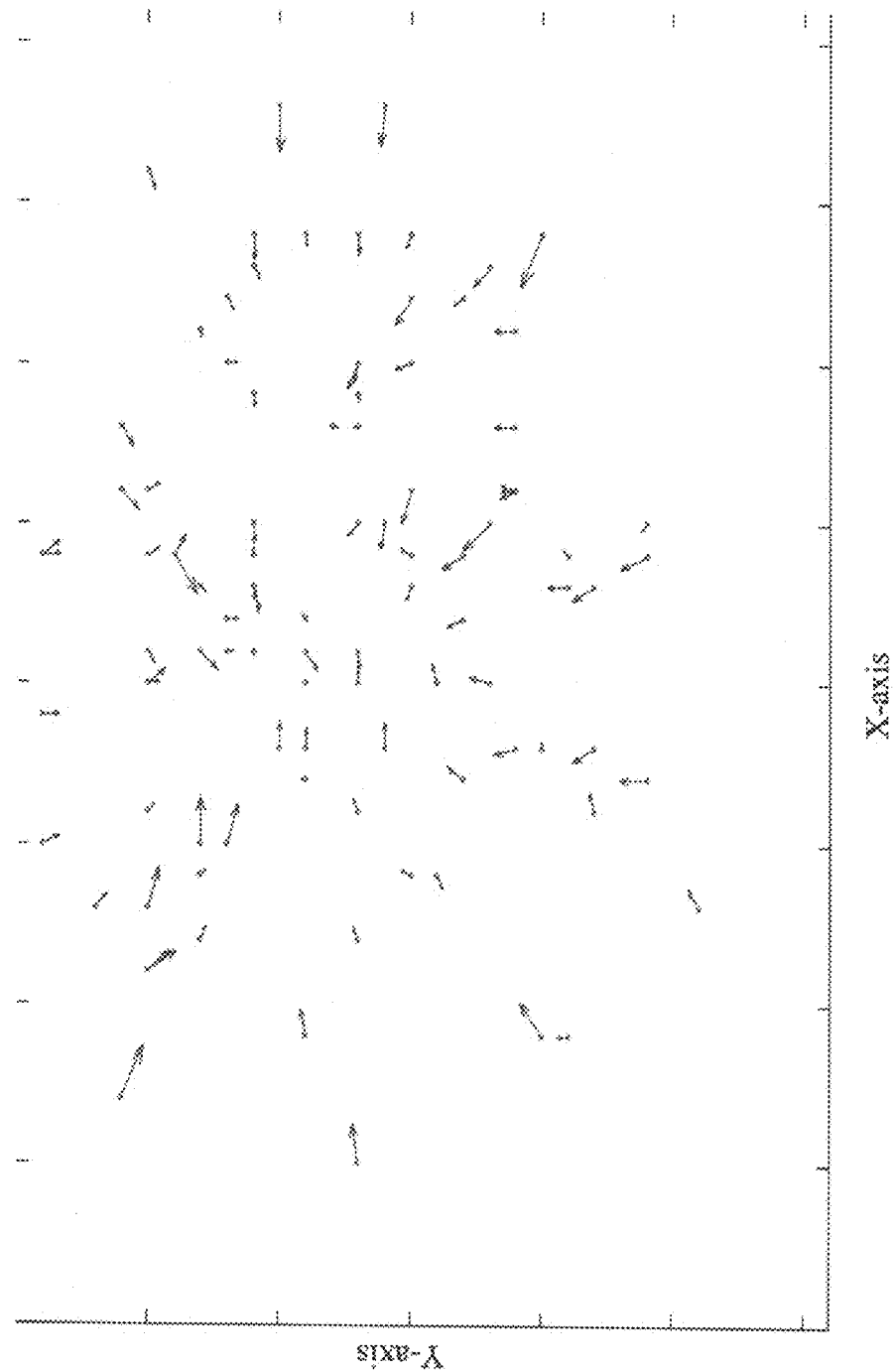
Figure 21:
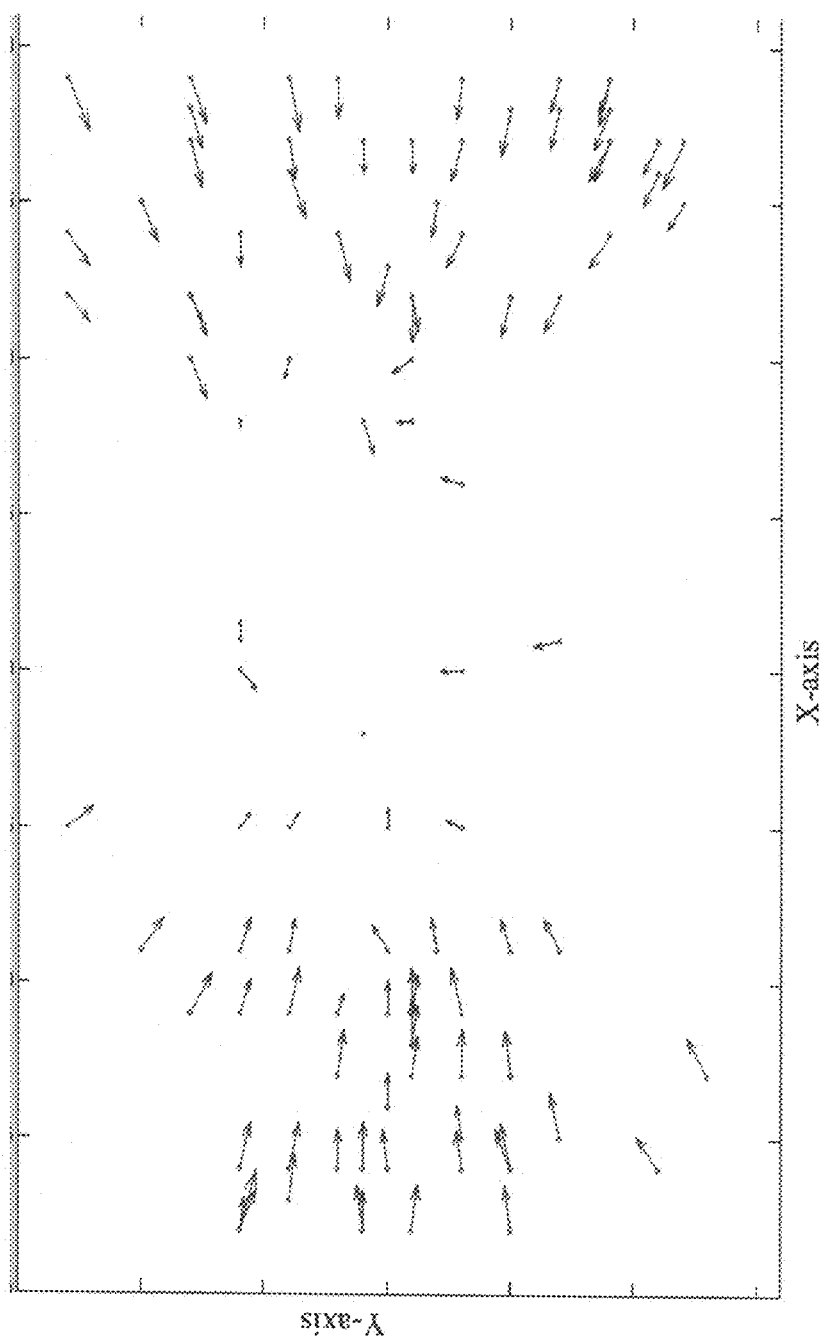

FIGS. 19-21 show selected sets containing 100 views having a single detector type, for large, medium, and small detectors respectively. Each view shows the detector location in the XY surface and the detector orientation (arrow), as seen from above where the shorter the arrow is the more downward it is pointing. The figures show that the selected set for the large detectors contains views which are mostly in the center of the XY surface and pointing directly in to the volume, whereas the selected set for the small detectors has the detectors located around the periphery of the volume and oriented at an angle towards the center of the volume.

Figure 22:
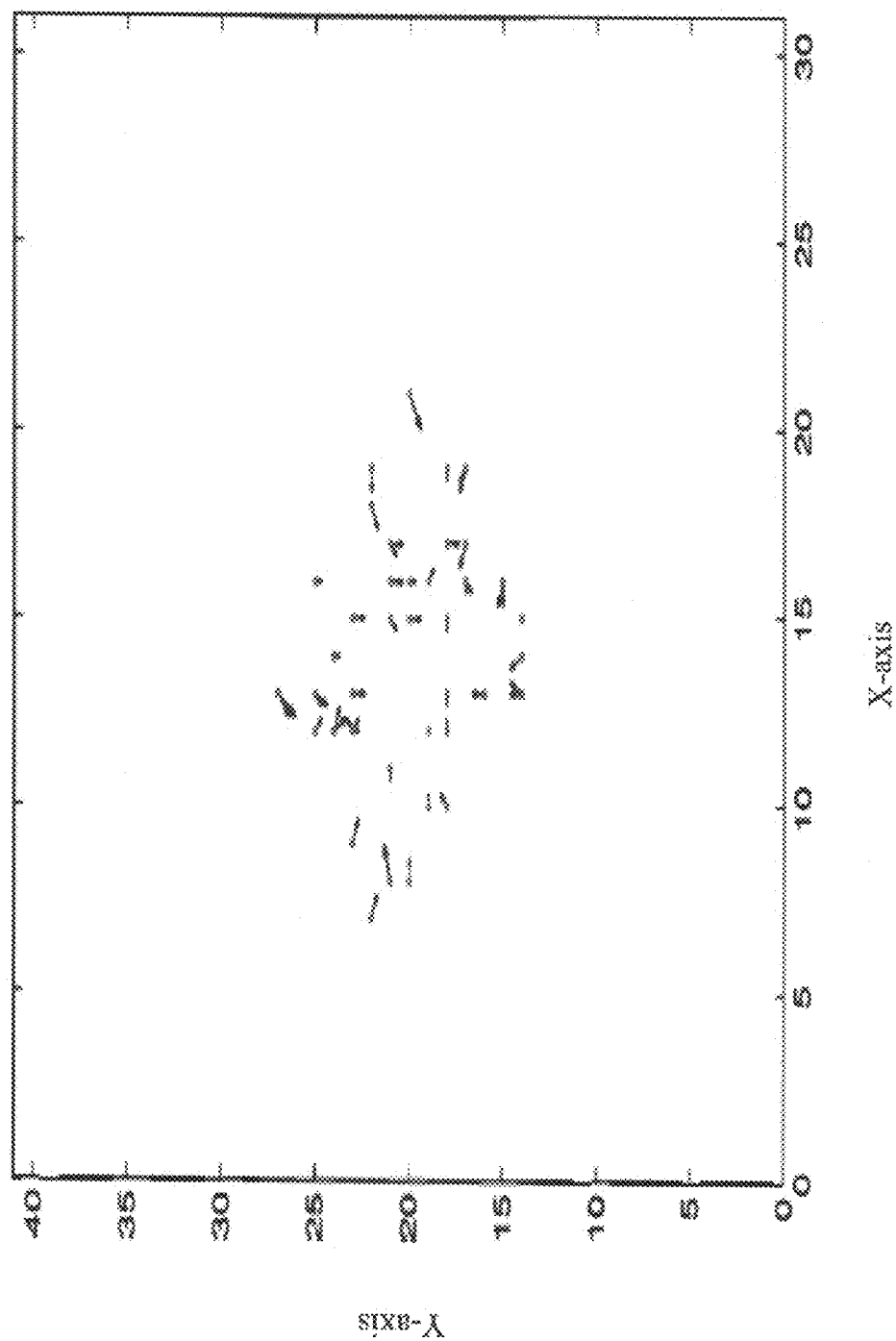
Figure 23:
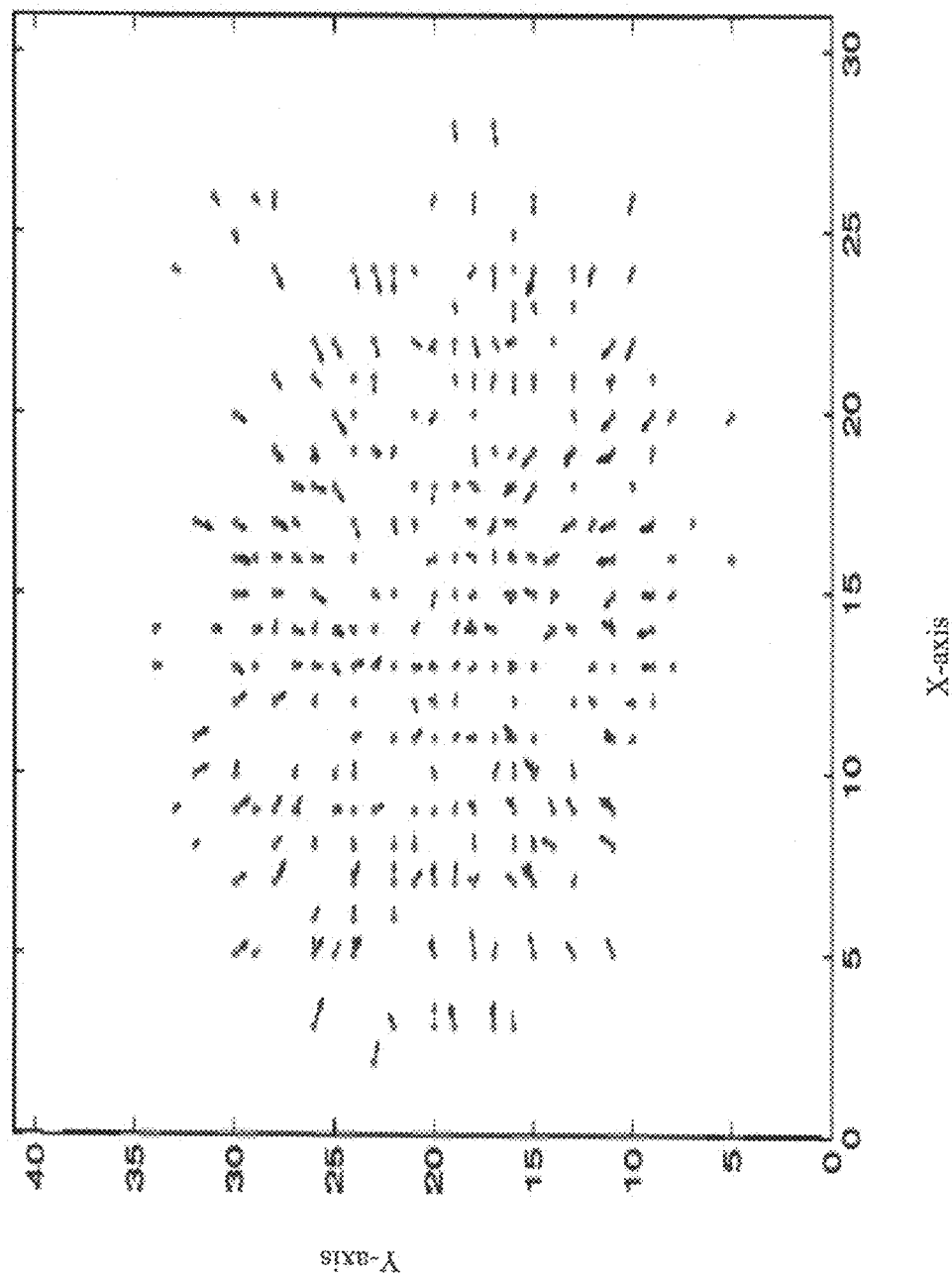
Figure 24:
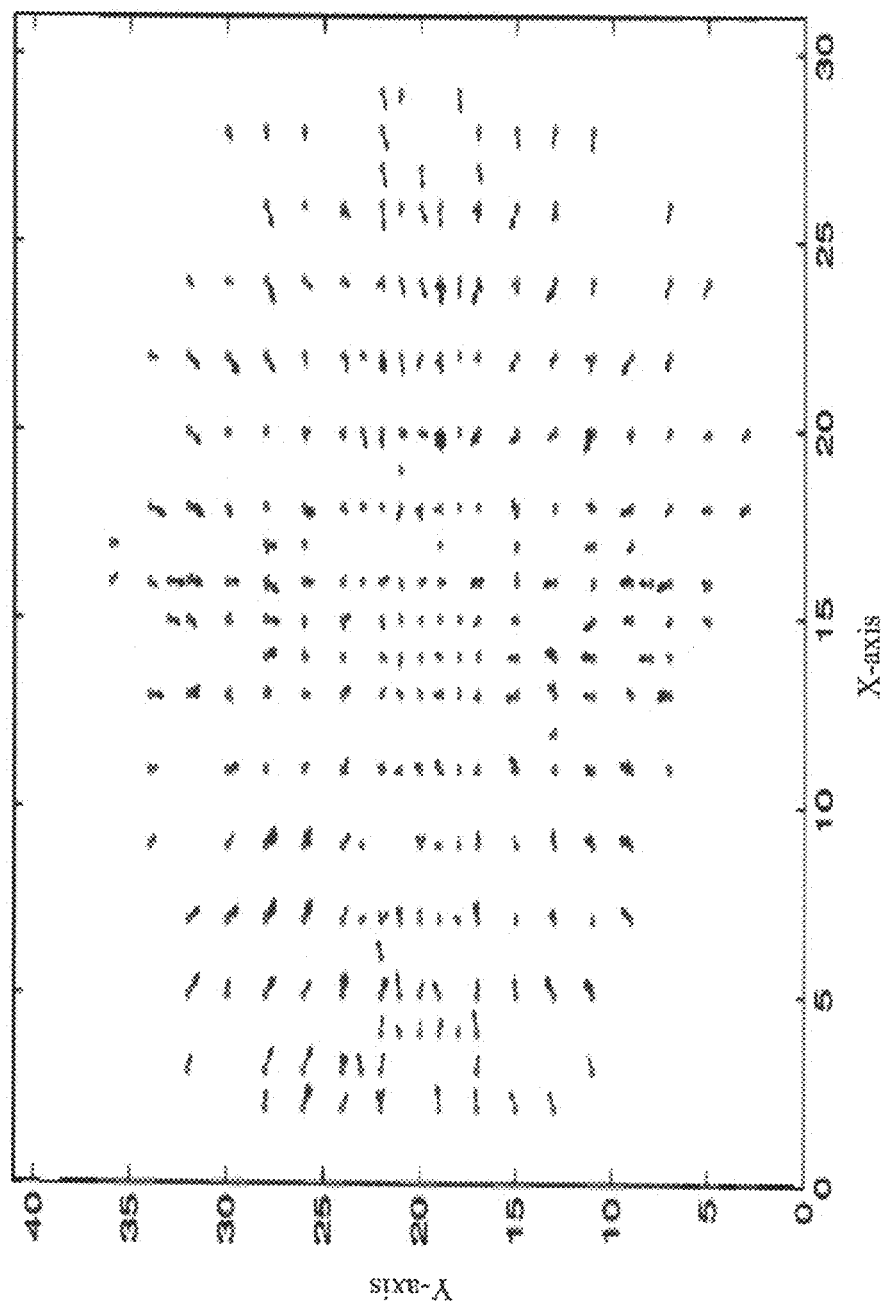
Figure 25:
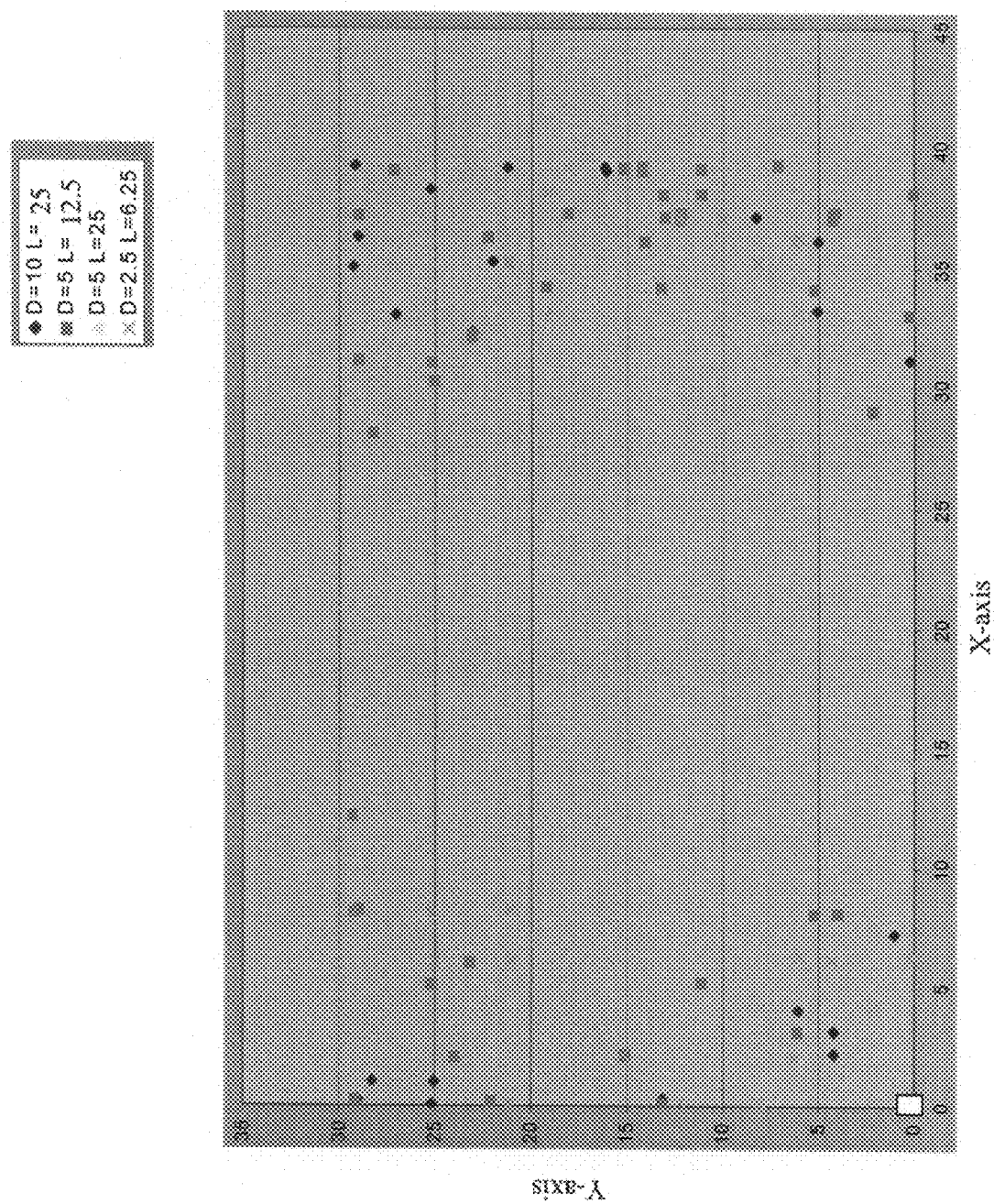
Figure 26:
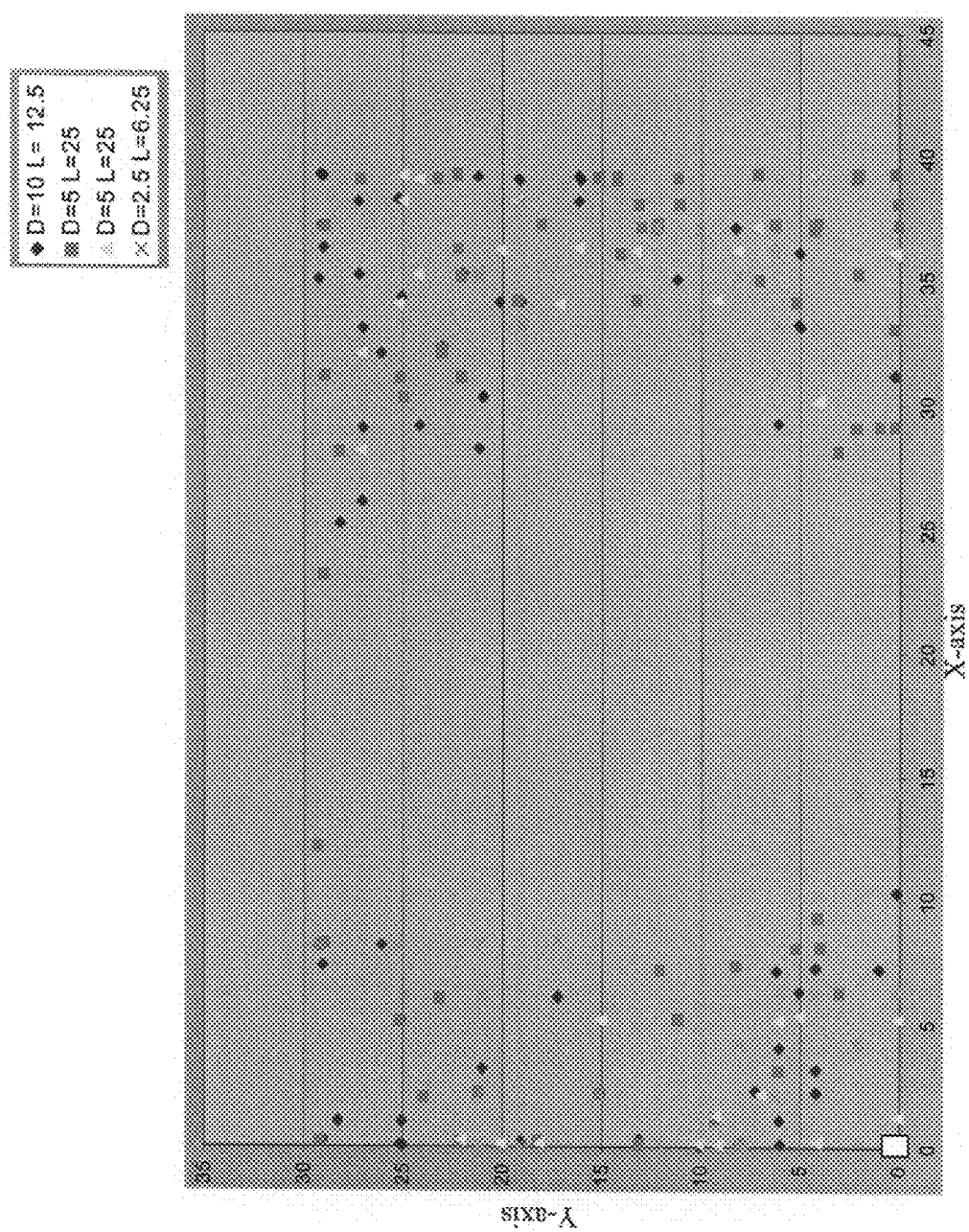
Figure 27:
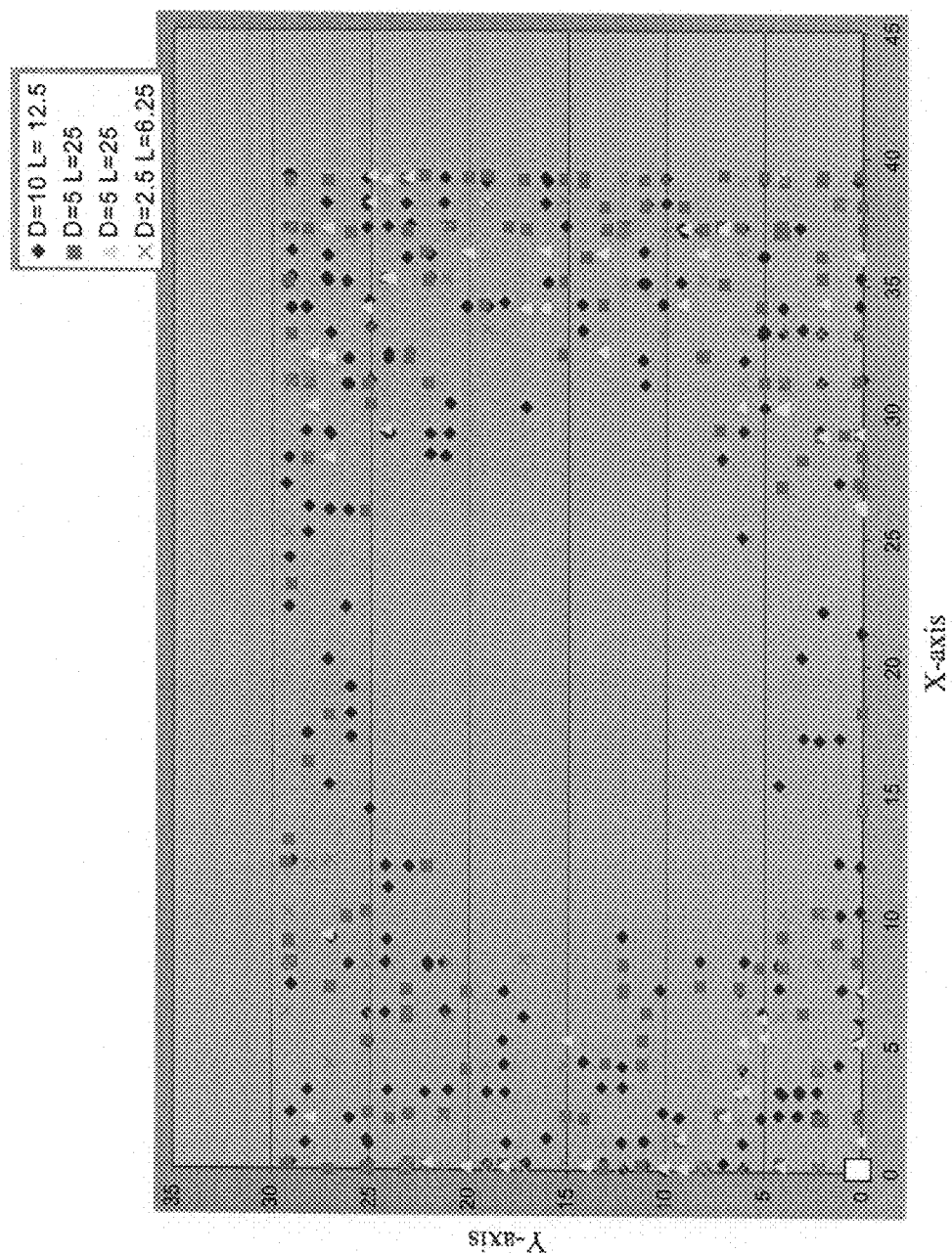
Figure 28:
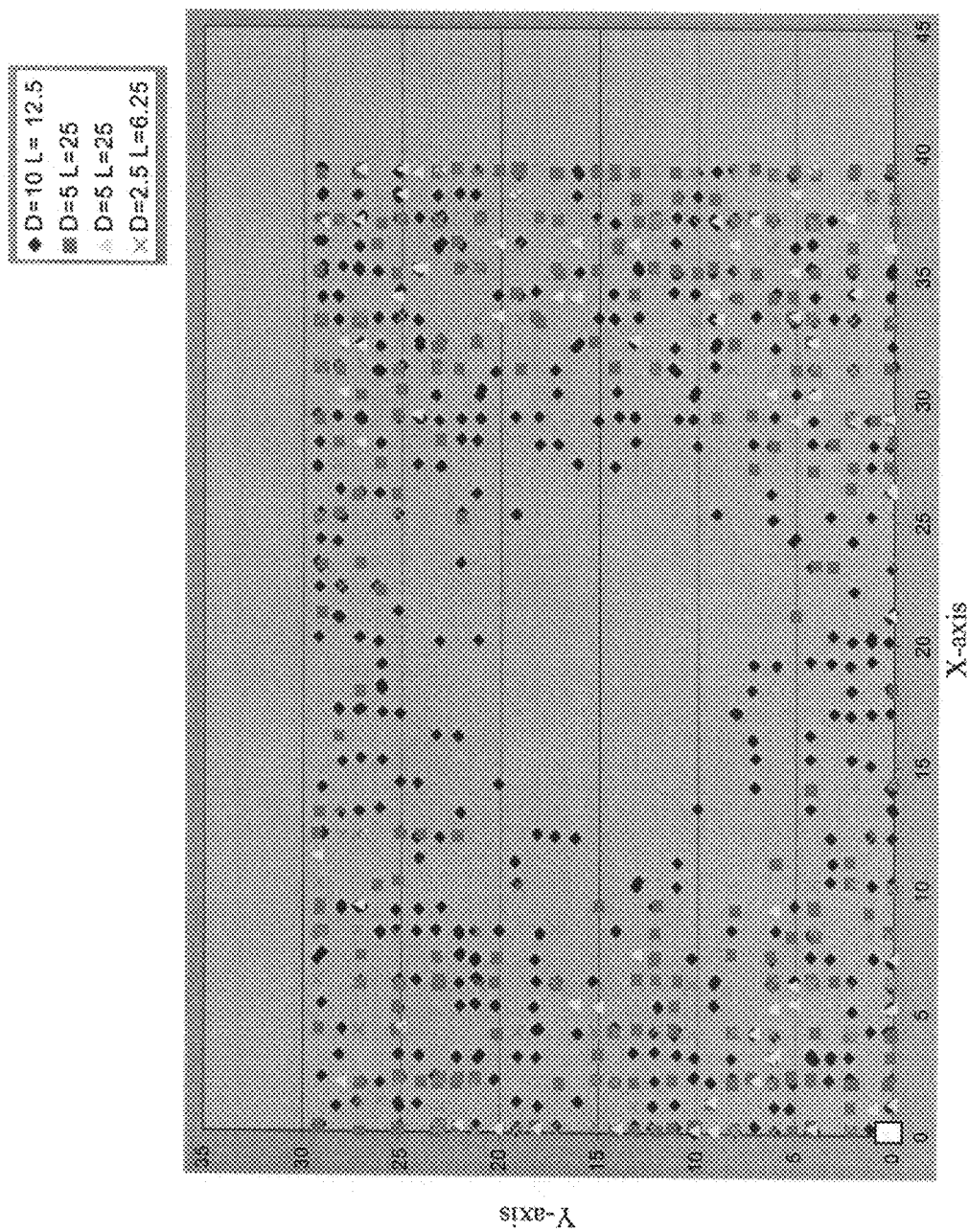

FIGS. 22-24 show a selected set containing 1000 views selected for the separability criterion. The selected set includes views of all three detector types. The selected set contains 55 large-detector views (FIG. 22), 370 medium-detector views (FIG. 23), and 575 small-detector views. Similarly to FIGS. 19-21, as the detectors decrease in size they are physically more dispersed over the XY surface.

FIGS. 25-32 illustrate view set selection results for the reliability criterion, based on the Fisher information measure. The specified viewing parameters are the location (on the XY surface) and the detector type. Each view is defined for one of four detector types, large (D=10, L=25), medium (D=5, L=12.5), small (D=2.5, L=6.25), and extra-focused (D=5, L=25).

Figure 29:
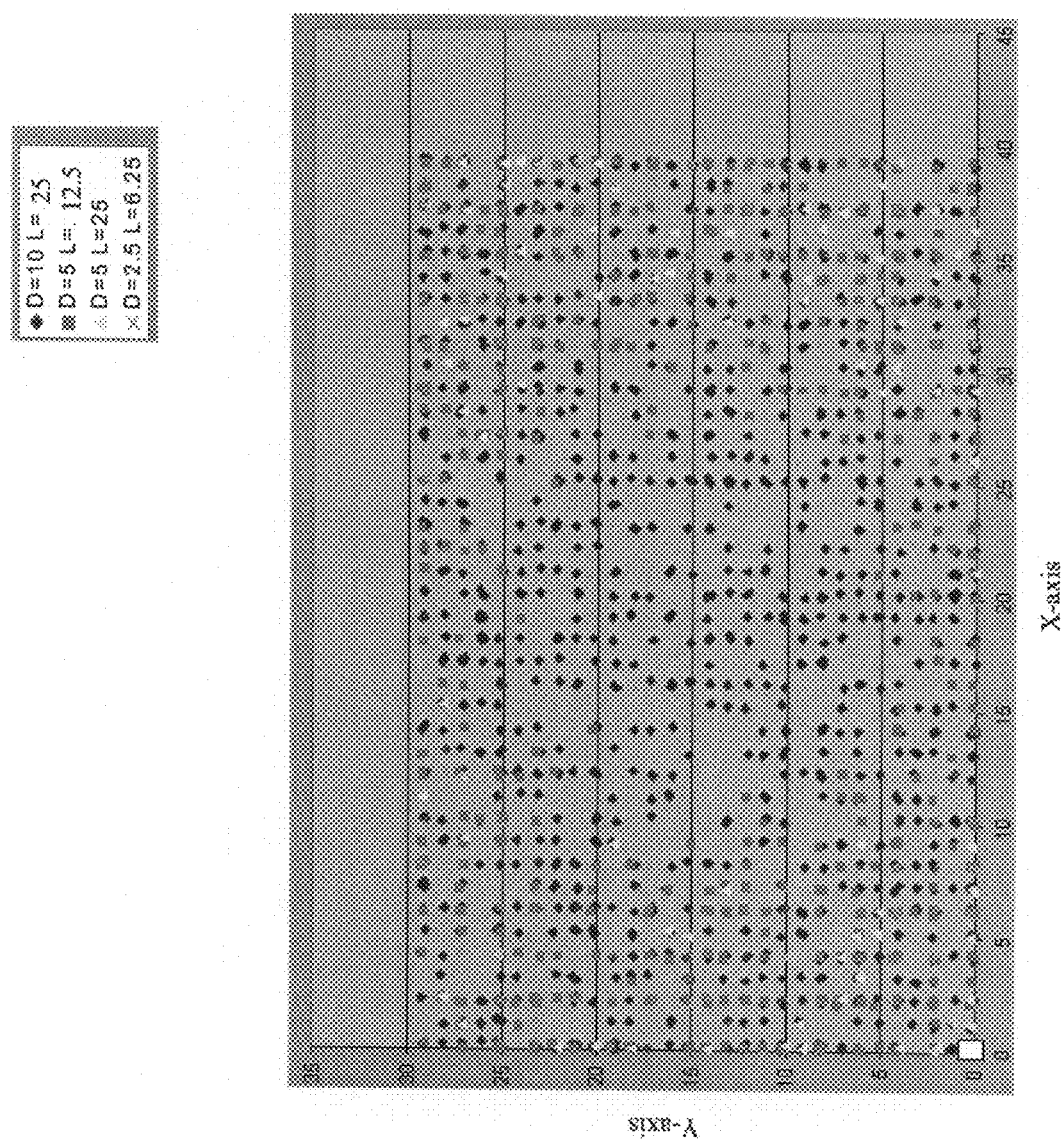

FIGS. 25-29 show selected sets based on the Fisher information measure, containing 100, 200, 500, 1000, and 2000 views respectively. As can be seen, for a small number of views the detectors are distributed around the periphery of the volume. As the number of views in the selected set increases, the detector move towards the center of the XY surface. In generally the selected sets with a greater number of views contain a higher proportion of small detector views than do the selected sets with fewer views. In particular, it is seen in FIG. 29 that the large detectors are concentrated in the center of the XY surface, while the smaller detectors are dispersed around the circumference.

Figure 30:
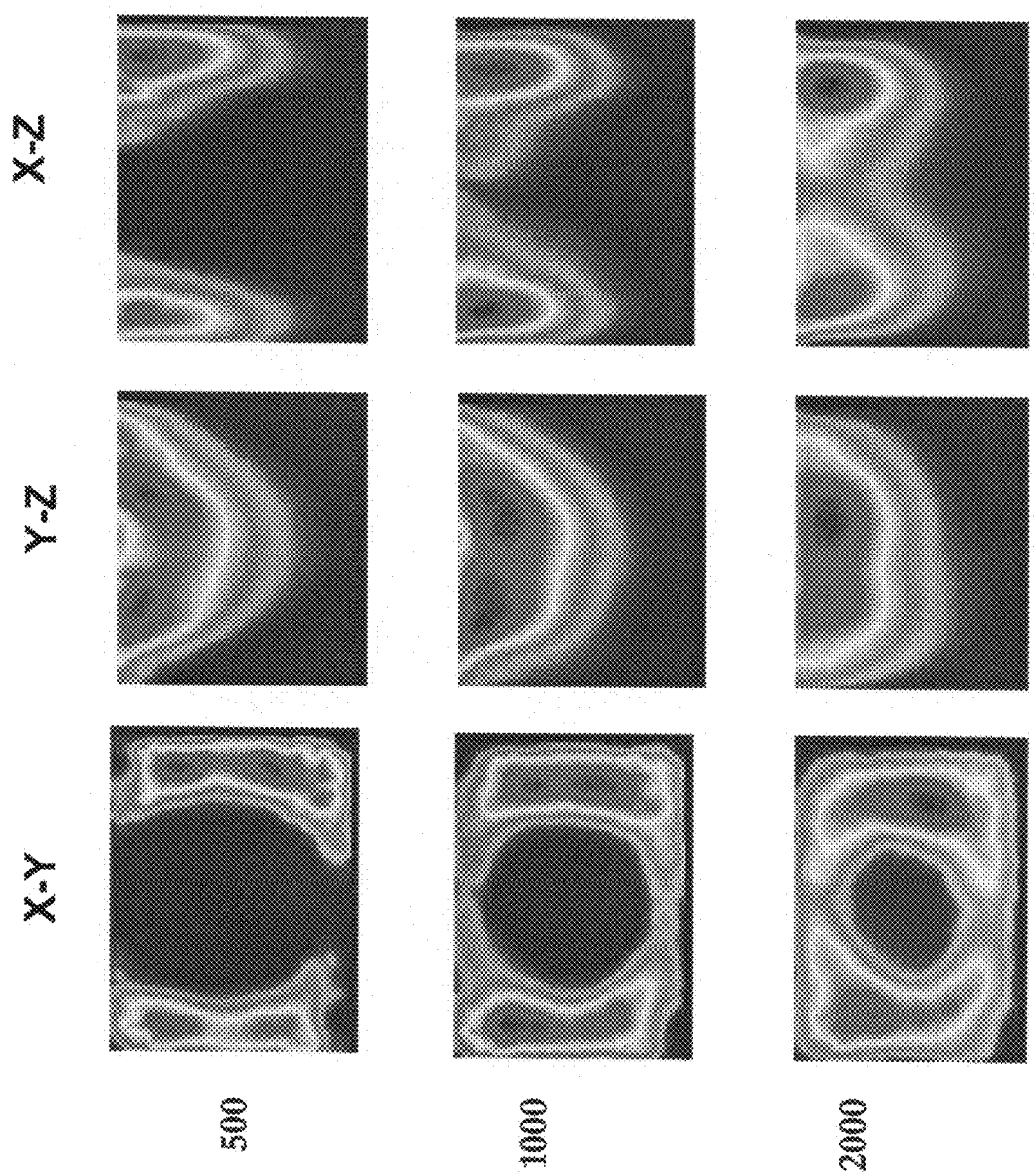

FIG. 30 shows the detector coverage of a volume for selected sets containing 500, 1000, and 2000 views. The coverage is shown from the XY, YZ, and XZ aspects of the volume. It is seen from the figure that for a small number of views, the views are clustered around the exterior of the volume. As the number of views increases, an increasingly uniform distribution of views is achieved.

Figure 31:
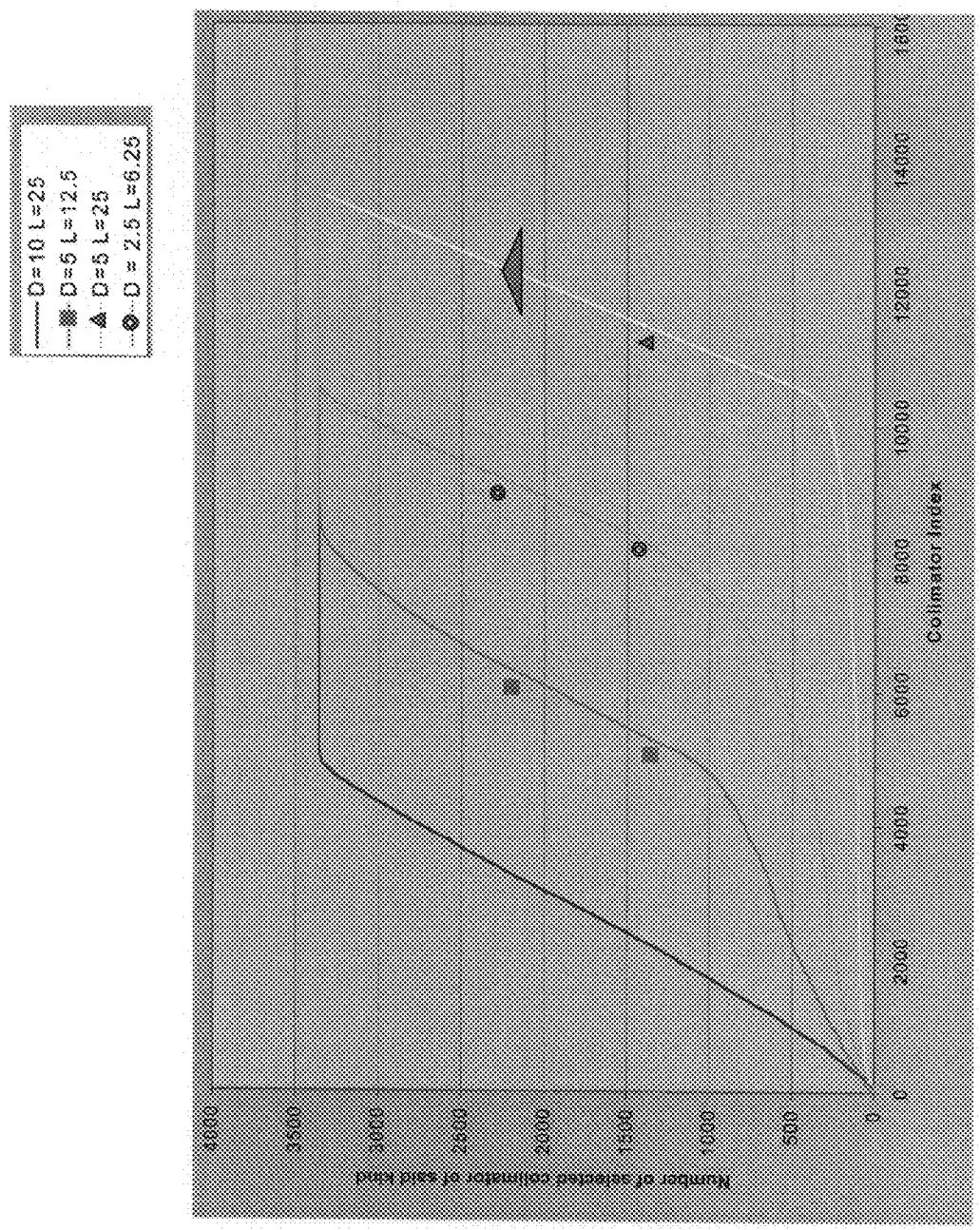
Figure 32:
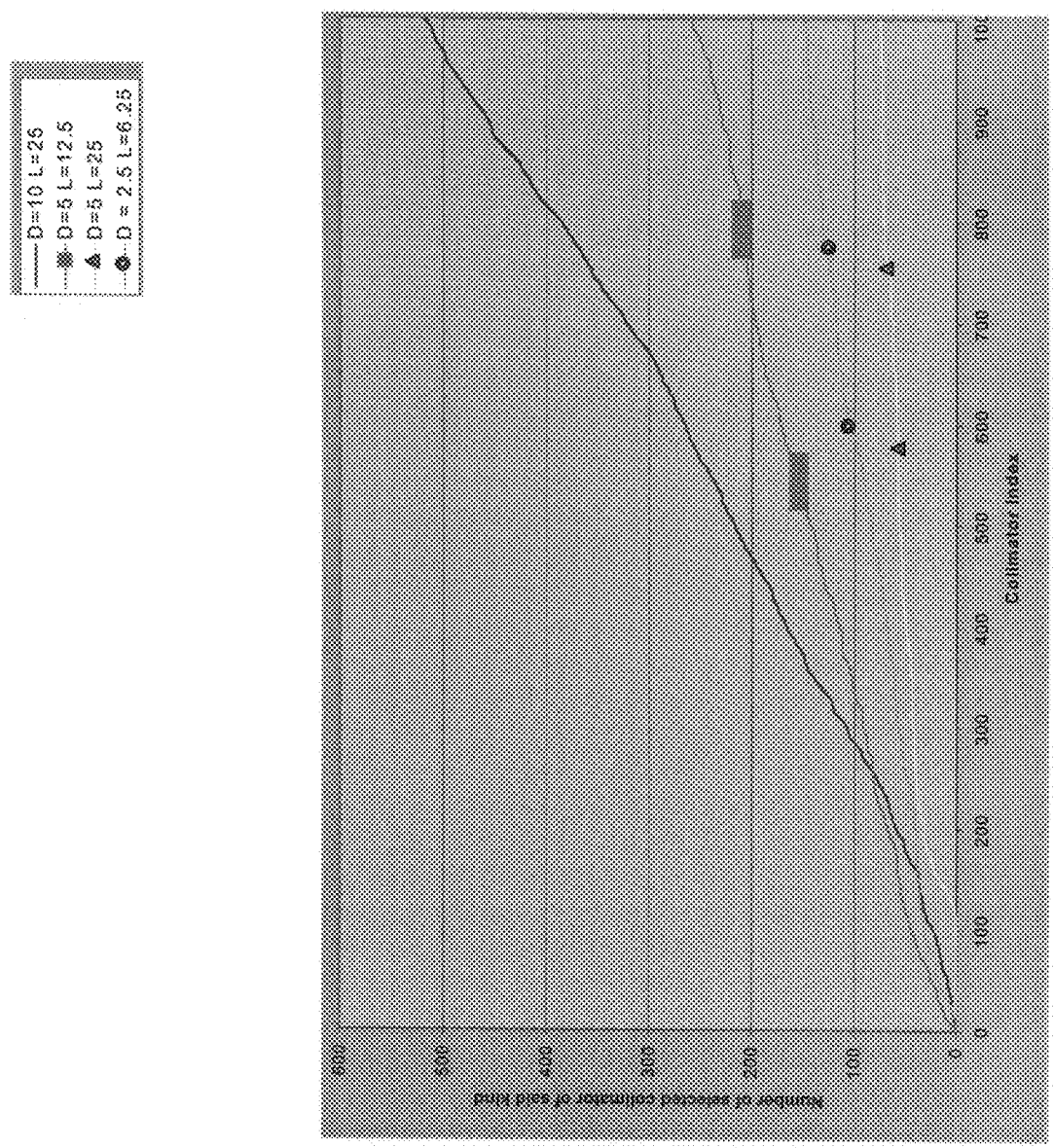

FIGS. 31-32 show the number of detectors selected for each of the four detector types, as the total number of selected views is increased. The selected set is constrained to have no more than 3400 views of a single detector type. It can be seen that the detectors are selected in order of size, as the total number of selected views increases. It is only after the number of the large detector views nears 3400 that the number of medium detector views begins to increase significantly, and so forth. The Fisher information measure is thus seen to select for larger-sized detectors, in order to ensure high-reliability reconstructions from the collected data.

FIG. 33 illustrates view set selection results for the reliability criterion, based on minimizing the inverse mean of the Fisher information measure. In accordance with the Cramer-Rao lower bound, the inverse of the Fisher Information is a lower bound for the variance of the intensity I.

FIG. 33 shows the behavior of the Fisher inverse mean for the three detector types, large (D=10, L=25), medium (D=5, L=12.5), and small (D=2.5, L=6.25). The number of collimators is normalized for the collimator size, so that an effective detector number of 1600 is achieved with 100 large detectors, 400 medium detectors, or with 1600 small detectors. The Fisher inverse mean of the medium and small detectors is relatively close, with the large detector having a greater mean value. Since our aim is to minimize the score, it is seen that the smaller detectors are more efficient in providing a low-variance estimation.

By enabling high-quality reconstruction based on data collected from a limited collection of views, the above described view set selection techniques present a way to resolve the current conflict between the relatively large-pixel detectors needed for measurement speed and data processing considerations, with the small-pixel detectors needed until now to obtain a high-resolution reconstruction. The data obtained using the selected set of views enables a high-resolution reconstruction from a smaller number of measurements. Additionally, reconstructing the intensity distribution from a smaller quantity of collected data simplifies the computational process. The above described embodiments are particularly suitable for medical imaging purposes, where a high-resolution image is needed and it is desired to minimize the difficulties of the patient undergoing the diagnostic testing or treatment.

Radioactive emission imaging, in accordance with the present invention may be performed with a radioactive-emission-measuring detector, such as a room temperature, solid-state CdZnTe (CZT) detector. It may be configured as a single-pixel or a multi-pixel detector, and may be obtained, for example, from eV Products, a division of II-VI Corporation, Saxonburg Pa., 16056, or from IMARAD IMAGING SYSTEMS LTD., of Rehovot, ISRAEL, 76124, www.imarad.com, or from another source. Alternatively, another solid-state detector such as CdTe, HgI, Si, Ge, or the like, or a combination of a scintillation detector (such as NaI(Tl), LSO, GSO, CsI, CaF, or the like) and a photomultiplier, or another detector as known, may be used.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for selecting a set of optimal views of a volume to be imaged by radioactive-emission, after an administration of a radiopharmaceutical, the method comprising:
   providing the volume to be imaged;
   providing a collection of views of the volume to be imaged, each said view is associated with at least one viewing parameter selected from a group consisting of a detector location, a detector orientation, a viewing angle, a detector material, a detector thickness, a collimator length, a septa thickness, a cell size, a detection duration, a time of detection, and a type of the radiopharmaceutical;
   providing a scoring function, by which any set of at least one view from the collection is scorable with a score that rates information obtained from the volume by the set;
   forming sets of views and scoring them, by the scoring function;
   selecting a set of views from the collection, based on the scoring function; and
   instructing a three dimensional (3D) reconstruction of an intensity distribution in at least some of the volume from radioactive-emission measurements of said selected set of views.

2. The method of claim 1, wherein the volume includes a body structure, selected from the group consisting of:
   a human prostate, a human heart, a human brain, a human breast, a human uterus, a human ovary, a human liver, a human kidney, a human stomach, a human colon, a human small intestine, a human oral cavity, a human throat, a human gland, a human lymph node, a human skin, another human body organ, a human limb, a human bone, another part of the human body, a whole human body,
   an animal prostate, an animal heart, an animal brain, an animal teat, an animal uterus, an animal ovary, an animal liver, an animal kidney, an animal stomach, an animal gastrointestinal track, an animal oral cavity, an animal throat, an animal gland, an animal lymph node, an animal skin, another animal body organ, an animal limb, an animal bone, another part of an animal body, a whole animal body,
   a model of a human prostate, a model of human heart, a model of human brain, a model of human breast, a model of human uterus, a model of human ovary, a model of human liver, a model of human kidney, a model of human stomach, a model of human colon, a model of human small intestine, a model of human oral cavity, a model of human throat, a model of human gland, a model of human lymph node, a model of human skin, another human body organ, a model of human limb, a model of human bone, another part of the human body, a model of whole human body,
   a model of animal prostate, a model of animal heart, a model of animal brain, a model of animal teat, a model of animal uterus, a model of animal ovary, a model of animal liver, a model of animal kidney, a model of animal stomach, a model of animal gastrointestinal track, a model of animal oral cavity, a model of animal throat, a model of animal gland, a model of animal lymph node, a model of animal skin, another animal body organ, a model of animal limb, a model of animal bone, another part of a model of animal body, and a model of whole animal body.

3. The method of claim 1, and further including imaging the volume with the selected set of views.

4. The method of claim 1, wherein:
   providing the volume to be imaged further includes providing a model of a body structure to be imaged,
   and further including imaging an in-vivo body structure, which corresponds to the model of the body structure, with the selected set of views.

5. The method of claim 1, wherein each of the views is associated with a collimated solid-state detector pixel.

6. The method of claim 5, wherein each of the views is associated with at least two viewing parameters, selected from the group consisting of: a solid-state-detector-pixel location, a solid-state-detector-pixel orientation, a solid-state-detector-pixel material, a solid-state-detector-pixel thickness, a solid-state-detector-pixel size, a septa thickness, a collimator solid collection angle, measurement duration, time elapsed from the administration of the radiopharmaceutical, the radiopharmaceutical half life, radioactive-emission particle, and radioactive-emission energy.

7. The method of claim 1, further comprising calculating for each of the views a respective detection probability distribution of the volume for each of the views, in accordance with respective viewing parameters and a volume attenuation coefficient.

8. The method of claim 1, wherein the selecting a set of views from the collection includes selecting a set from the group consisting of:
   a minimal-size set, which attains a predefined score, and a highest scoring set, having a predefined number of views.

9. The method of claim 1, wherein the collection of views comprises a quantized continuum of views.

10. The method of claim 1, wherein the scoring function is selected from the group consisting of:
- an information-theoretic entropy measure, for ensuring uniform coverage of the volume,
- a worst-case effectiveness for the given view over the volume, and
- an average effectiveness for the given view over the volume.

11. The method of claim 1, further comprising providing at least one emittance model, wherein an emittance model comprises a representation of a radioactive-emission density distribution of the volume.

12. The method of claim 11, wherein:
- the providing at least one emittance model comprises providing a pair of models of substantially identical volumes, but different radioactive-emission density distributions, wherein the difference between the radioactive-emission density distributionsis defined by at least one delta;
- the scoring function is based on an information theoretic measure of separability;
- the forming the sets of views from the collection of views and scoring them, comprises forming substantially identical sets of views for the pair of models and scoring the sets with respect to the pair; and
- the selecting one of the sets of views, based on its score, comprises selecting based on the score for the pair.

13. The method of claim 11, wherein:
- the providing the at least one emittance model includes providing at least two emittance models, and further wherein the scoring function is selected from the group consisting of:
- a worst-case effectiveness for the given view over the set of emittance models, and an average effectiveness for the given view over the set of emittance models.

14. The method of claim 11, wherein the scoring function comprises an information theoretic measure, selected from the group consisting of:
- an information-theoretic Fisher information measure, for ensuring reliable reconstruction of the radioactive-emission density distribution,
- an information-theoretic likelihood measure, for ensuring separable reconstructions of the at least one emittance model, and
- a combination thereof.

15. The method of claim 11, wherein the providing at least one emittance model includes modeling a radioactive-emission density distribution in at least one modeled body structure.

16. The method of claim 15, wherein the body structure is selected from the group consisting of: selected from the group consisting of a human prostate, a human heart, a human brain, a human breast, a human uterus, a human ovary, a human liver, a human kidney, a human stomach, a human colon, a human small intestine, a human oral cavity, a human throat, a human gland, a human lymph node, a human skin, another human body organ, a human limb, a human bone, another part of the human body, a whole human body, an animal prostate, an animal heart, an animal brain, an animal teat, an animal uterus, an animal ovary, an animal liver, an animal kidney, an animal stomach, an animal gastrointestinal track, an animal oral cavity, an animal throat, an animal gland, an animal lymph node, an animal skin, another animal body organ, an animal limb, an animal bone, another part of an animal body, and a whole animal body.

17. The method of claim 1, wherein said collection of views comprises a collection of radionuclide imaging views.

18. A method for selecting a set of optimal views of a volume to be imaged by radioactive-emission, after an administration of a radiopharmaceutical, the method comprising:
- providing the volume to be imaged;
- providing at least one emittance model;
- providing a collection of views of the volume to be imaged;
- providing a scoring function, by which any set of at least one view from the collection is scorable with a score that rates information obtained from the volume by the set;
- forming sets of views and scoring them, by the scoring function; and
- selecting a set of views from the collection, based on the scoring function;
- wherein an emittance model comprises a representation of a radioactive-emission density distribution of the volume,
- wherein:
  - the providing at least one emittance model comprises providing a plurality of emittance models of substantially identical volumes, but different radioactive-emission density distributions,
  - the forming sets of views from the collection of views and scoring them, comprises forming substantially identical sets of views for all the models and scoring the sets with respect to each model, based on the information theoretic measure of reliability; and
  - the selecting one of the sets of views, based on its score, comprises selecting based on the average score for the plurality of models.

19. A method for selecting a set of optimal views of a volume to be imaged by radioactive-emission, after an administration of a radiopharmaceutical, the method comprising:
- providing the volume to be imaged;
- providing at least one emittance model;
- providing a collection of views of the volume to be imaged;
- providing a scoring function, by which any set of at least one view from the collection is scorable with a score that rates information obtained from the volume by the set;
- forming sets of views and scoring them, by the scoring function; and
- selecting a set of views from the collection, based on the scoring function;
- wherein an emittance model comprises a representation of a radioactive-emission density distribution of the volume, wherein:
  - the providing at least one emittance model comprises providing a plurality of pairs of models of substantially identical volumes, but different radioactive-emission density distributions, wherein the difference between the radioactive-emission density distributions for each pair is defined by at least one delta;
  - the scoring function is based on an information theoretic measure of separability;
  - the forming the sets of views from the collection of views and scoring them, comprises forming substantially identical sets of views for the plurality of pairs of models and scoring the sets with respect to each of the pairs; and
  - the selecting one of the sets of views, based on its score, comprises selecting based on an average score for the plurality of pairs.

20. A method for selecting a set of optimal views of a volume to be imaged by radioactive-emission, after an administration of a radiopharmaceutical, the method comprising:
- providing the volume to be imaged;
- providing at least one emittance model;
- providing a collection of views of the volume to be imaged;

providing a scoring function, by which any set of at least one view from the collection is scorable with a score that rates information obtained from the volume by the set;

forming sets of views and scoring them, by the scoring function; and selecting a set of views from the collection, based on the scoring function;

wherein an emittance model comprises a representation of a radioactive-emission density distribution of the volume, wherein:

the providing the at least one emittance model includes providing a first and a second emittance models of different radiation emission density distributions and a third emittance model of no radiation emission density distribution; and the providing the scoring function comprises providing a scoring function as a combination of uniformity, separability and reliability.

21. A method for selecting a set of optimal views of a volume to be imaged by radioactive-emission, after an administration of a radiopharmaceutical, the method comprising:

providing the volume to be imaged;

providing a collection of views of the volume to be imaged;

providing a scoring function, by which any set of at least one view from the collection is scorable with a score that rates information obtained from the volume by the set;

forming sets of views and scoring them, by the scoring function; and selecting a set of views from the collection, based on the scoring function;

wherein the selecting comprises:

initially establishing a current set of views from the collection of views; and iteratively expanding the current set until a predefined number of views are obtained, wherein a set expansion iteration comprises:

forming a respective expanded set for each view not in the current set, wherein an expanded set comprises the current set and a respective view;

calculating a respective score for each of the expanded sets using the scoring function; and equating the current set equal to a highest-scoring expanded set.

22. The method of claim 21, wherein the initially established current set is an empty set.

23. A non-transitory computer-readable storage medium containing a set of instructions for selecting a set of optimal views of a volume to be imaged by radioactive-emission, after an administration of a radiopharmaceutical, the set of instructions comprising:

a volume provision routine for providing the volume to be imaged;

a view provision routine for providing a collection of views of the volume to be imaged, each said view is associated with at least one viewing parameter selected from a group consisting of a detector location, a detector orientation, a viewing angle, a detector material, a detector thickness, a collimator length, a septa thickness, a cell size, a detection duration, a time of detection, and a type of the radiopharmaceutical;

a scoring function provision routine for providing a scoring function, by which any set of at least one view from the collection is scorable with a score that rates information obtained from the volume by the set;

a set formation routine, for forming sets of views and scoring them, by the scoring function; and a set selection routine selecting a set from the collection, based on the scoring function;

wherein said set is used for instructing a three dimensional (3D) reconstruction of an intensity distribution in at least some of the volume from radioactive-emission measurements of said selected set of views.

24. A computer system, configured for selecting a set of optimal views of a volume to be imaged by radioactive-emission, after an administration of a radiopharmaceutical, comprising:

a volume provision routine for providing the volume to be imaged;

a view provision routine for providing a collection of views of the volume to be imaged, each said view is associated with at least one viewing parameter selected from a group consisting of a detector location, a detector orientation, a viewing angle, a detector material, a detector thickness, a collimator length, a septa thickness, a cell size, a detection duration, a time of detection, and a type of the radiopharmaceutical;

a scoring function provision routine for providing a scoring function, by which any set of at least one view from the collection is scorable with a score that rates information obtained from the volume by the set;

a set formation routine, for forming sets of views and scoring them, by the scoring function; and a set selection routine selecting a set from the collection, based on the scoring function;

wherein said set is used for instructing a three dimensional (3D) reconstruction of an intensity distribution in at least some of the volume from radioactive-emission measurements of said selected set of views.

* * * * *